(12) United States Patent
Genin et al.

(10) Patent No.: US 8,153,624 B2
(45) Date of Patent: Apr. 10, 2012

(54) COMPOUNDS AND METHODS FOR MODULATING FXR

(75) Inventors: Michael James Genin, Zionsville, IN (US); Francisco Javier Agejas-Chicharro, Madrid (ES); Ana Belen Bueno Melendo, Madrid (ES); Peter Rudolph Manninen, Brownsburg, IN (US); Alan M. Warshawsky, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 217 days.

(21) Appl. No.: 12/600,879

(22) PCT Filed: Jul. 11, 2008

(86) PCT No.: PCT/US2008/069719
§ 371 (c)(1),
(2), (4) Date: Nov. 19, 2009

(87) PCT Pub. No.: WO2009/012125
PCT Pub. Date: Jan. 22, 2009

(65) Prior Publication Data
US 2010/0152166 A1    Jun. 17, 2010

Related U.S. Application Data

(60) Provisional application No. 60/949,974, filed on Jul. 16, 2007.

(51) Int. Cl.
*A61K 31/55*    (2006.01)
*C07D 405/00*    (2006.01)

(52) U.S. Cl. .................. 514/217.03; 514/378; 540/596; 548/240

(58) Field of Classification Search .................. 540/596; 548/240; 514/378, 217.03
See application file for complete search history.

(56) References Cited

U.S. PATENT DOCUMENTS

| 5,990,139 | A | 11/1999 | Yano et al. | |
| 6,967,212 | B2 * | 11/2005 | Cheng et al. | 514/365 |
| 7,105,556 | B2 | 9/2006 | Cheng et al. | |

FOREIGN PATENT DOCUMENTS

| WO | 00/37077 | 6/2000 |
| WO | 03/015771 | 2/2003 |
| WO | 2004/004655 | 1/2004 |
| WO | 2004/048349 | 6/2004 |
| WO | 2007/092751 | 8/2007 |
| WO | 2007/140174 | 12/2007 |
| WO | 2007/140183 | 12/2007 |

* cited by examiner

*Primary Examiner* — Rei-tsang Shiao
(74) *Attorney, Agent, or Firm* — Elizabeth Dingess-Hammond

(57) ABSTRACT

Compounds of formula (I): formula (I) wherein variables are as defined herein and their pharmaceutical compositions and methods of use are disclosed as useful for treating dyslipidemia and diseases related to dyslipidemia.

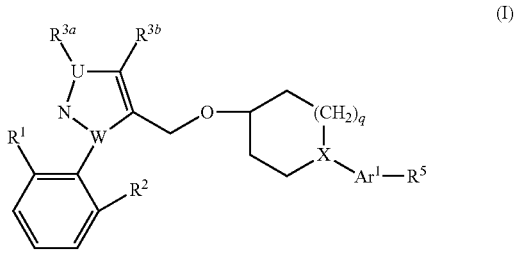

18 Claims, No Drawings

COMPOUNDS AND METHODS FOR MODULATING FXR

This is a 371 (national filing) of PCT/US2008/069719, filed Jul. 11, 2008, which claims priority to U.S. Ser. No. 60/949,974, filed Jul. 16, 2007.

FIELD OF THE INVENTION

The current invention relates to the fields of medicinal chemistry, pharmacology, and medicine. Specifically, the invention relates to novel compounds useful for the treatment dyslipidemia and diseases related to dyslipidemia.

Dyslipidemia and diseases related to dyslipidemia e.g. atherosclerosis, coronary artery disease, stroke, etc., are major causes of death, morbidity, and economic loss. Plasma lipids, especially cholesterol fractions, are recognized as having a significant role in cardiovascular health. Favorable modulation of plasma lipids such as triglycerides, HDL cholesterol, and LDL cholesterol is desirable.

Numerous efforts are underway to provide safe and efficacious molecular entities for the treatment of diseases related to dyslipidemia. For example, patent application WO 2004/048349 A1 discloses compounds purportedly useful as farnesoid X receptor (FXR) agonists. PCT international application WO2007/092751 A3 discloses isoxazole compounds useful for modulating FXR. PCT International application WO 2007/140174 A2 discloses aryltriazole derivatives as FXR modulators and their preparation, pharmaceutical compositions, and use in the treatment of dyslipidemia and related diseases.

FXR agonists are ligands for a nuclear receptor that regulates the transcription of genes that control triglyceride, cholesterol, and carbohydrate metabolism. The above efforts and others not withstanding, there remains a need to discover and develop compounds that are believed to be potent and efficacious (based on in-vitro and in-vivo models) agonists of FXR. Such compounds would be useful for the treatment of disorders characterized by or resulting from an undesirable lipid profile including dyslipidemia and related diseases e.g., atherosclerosis.

The present invention provides a compound of formula I

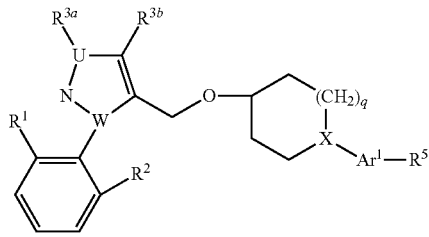

wherein:
q is 1 or 2, provided that when X is C, q is 1;
U is O, N or C; provided that when U is O or N, $R^{3a}$ is absent; and provided that when U is N or C, the UN bond is a double bond; and provided that when W is C, the WN bond is a double bond;
W is C or N;
X is C or N;
$R^1$ is chloro, fluoro, or trifluoromethoxy;
$R^2$ is hydrogen chloro, fluoro, or trifluoromethoxy;
$R^{3a}$ is hydrogen, or absent;
$R^{3b}$ is trifluoromethyl, cyclopropyl or isopropyl; $Ar^1$ is selected from the group consisting of 6-indolyl, 6-benzothienyl, 4-naphthyl, 4-phenyl, and 2-pyridinyl, each optionally substituted with one or two groups independently selected from the group consisting of methyl, ethyl, and phenyl; and $R^5$ is COOH; or a pharmaceutically acceptable salt, enantiomer, diastereomer or mixture thereof.

The compounds of the present invention are agonists of FXRs. The compounds of present invention are useful for beneficially altering lipid profiles including but not limited to lowering total cholesterol levels, lowering LDL cholesterol levels, lowering VLDL cholesterol levels, raising HDL cholesterol levels, and/or lowering triglyceride levels. Thus, the present invention provides a method for treating FXR mediated conditions such as dyslipidemia and diseases related to dyslipidemia comprising administering a therapeutically effective amount of a compound of the present invention to a patient in need thereof.

The present invention also provides a method for treating atherosclerosis comprising administering a therapeutically effective amount of a compound of the present invention to a patient in need thereof.

The present invention also provides a pharmaceutical composition comprising a compound of the present invention and a pharmaceutically acceptable carrier.

The present invention also relates to compounds of the present invention for use in therapy, in particular for use in treating dyslipidemia and related diseases. The present invention also relates to compounds of the present invention for use in treating atherosclerosis.

The present invention also relates to the use of a compound of the present invention in the manufacture of a medicament for the treatment of dyslipidemia or related diseases. The present invention also relates to the use of a compound of the present invention in the manufacture of a medicament for the treatment of atherosclerosis.

The term "dyslipidemia" as used herein refers to an abnormality in, or abnormal amounts of lipids and lipoproteins in the blood and the disease states resulting, caused by, exacerbated by, or adjunct to such abnormality (see *Dorland's Illustrated Medical Dictionary, 29th edition*, W.B Saunders publishing Company, New York, N.Y.). Disease states encompassed within the definition of dyslipidemia as used herein include hyperlipidemia, hypertriglyceremia, low plasma HDL, high plasma LDL, high plasma VLDL, liver cholestosis, and hypercholesterolemia.

The phrase "diseases related to dyslipidemia" as used herein refers to diseases including but not limited to atherosclerosis, thrombosis, coronary artery disease, stroke, and hypertension. Diseases related to dyslipidemia also include metabolic diseases such as obesity, diabetes, insulin resistance, and complications thereof. Complications of diabetes include but are not limited diabetic retinopathy.

As used herein, the term "therapeutically effective amount" means an amount of a compound of the invention that is part of an approved therapeutic regimen, or is determined by a qualified prescriber to be sufficient taken as directed, for treating a condition herein described.

Compounds of the invention may possess one or more chiral centers, and thus, may exist in optically active forms. All such optically active forms or stereoisomers are within the ambit of the present invention. If a particular stereoisomer is desired, it can be prepared by methods well known in the art.

Preferably $R^1$ is chloro or trifluoromethoxy.

Preferably, $R^2$ is chloro or H.

Preferably $R^{3b}$ is cyclopropyl or isopropyl.

A preferred $Ar^1$ group is an optionally substituted 4-phenyl, 2-pyridinyl, 6-benzothienyl or 6-indolyl. More preferred $Ar^1$ is an optionally substituted 4-phenyl, 6-indolyl, or 6-benzothienyl. Most preferred $Ar^1$ is optionally substituted 4-phenyl or 6-indolyl. Preferably $Ar^1$ is optionally substituted with a group selected from the group consisting of methyl, ethyl and phenyl. A more preferred optional substituent is methyl.

Also preferred is a compound of formula I wherein: $R^1$ is chloro or trifluoromethoxy; $R^2$ is hydrogen or chloro; $R^{3a}$ is hydrogen or absent; $R^{3b}$ is cyclopropyl or isopropyl and $Ar^1$ group is 4-phenyl, 2-pyridinyl, 6-indolyl, or 6-benzothienyl each optionally substituted with a group selected from methyl or trifluoromethyl or phenyl.

Also preferred is a compound of formula I wherein q is 1; $R^1$ is chloro or trifluoromethoxy; $R^2$ is hydrogen or chloro; $R^{3b}$ is cyclopropyl and $Ar^1$ group is 4-phenyl, 2-pyridinyl, or 6-indolyl, each optionally substituted with methyl. Also preferred is a compound of formula I wherein q is 2; $R^1$ is chloro or trifluoromethoxy; $R^2$ is hydrogen or chloro; $R^{3b}$ is cyclopropyl; X is N and $Ar^1$ group is 4-phenyl, 2-pyridinyl, or 6-indolyl, each optionally substituted with methyl.

Also preferred is a compound of formula I wherein U is oxygen, and W is carbon forming an isoxazole ring; $R^1$ is chloro or trifluoromethoxy; $R^2$ is hydrogen or chloro; $R^{3a}$ is absent and $R^{3b}$ is cyclopropyl and $Ar^1$ group is 4-phenyl, 2-pyridinyl, 6-indolyl or 6-benzothienyl each optionally substituted with methyl.

Also preferred is a compound of formula I wherein: U and W are both nitrogen forming a triazole ring; $R^1$ is chloro or trifluoromethoxy; $R^2$ is hydrogen or chloro; $R^{3a}$ is absent and $R^{3b}$ is cyclopropyl or isopropyl and $Ar^1$ group is 4-phenyl, 6-indolyl or 6-benzothienyl, each optionally substituted with methyl or phenyl.

Also preferred is a compound of formula I wherein: U is carbon, W is nitrogen forming a pyrazole ring; $R^1$ is chloro or trifluoromethoxy; $R^2$ is hydrogen or chloro; $R^{3a}$ is hydrogen and $R^{3b}$ is cyclopropyl, or isopropyl and $Ar^1$ group is 4-phenyl, 6-indolyl or 6-benzothienyl, each optionally substituted with methyl or phenyl.

Also preferred is a compound of formula I wherein q is 1; U is oxygen, and W is carbon forming an isoxazole ring; $R^1$ is chloro or trifluoromethoxy; $R^2$ is hydrogen or chloro; $R^{3a}$ is absent and $R^{3b}$ is cyclopropyl; X is C and $Ar^1$ group is 4-phenyl, 2-pyridinyl, 6-indolyl or 6-benzothienyl each optionally substituted with methyl.

Also preferred is a compound of formula I wherein: q is 1; U and W are both nitrogen forming a triazole ring; $R^1$ is chloro or trifluoromethoxy; $R^2$ is hydrogen or chloro; $R^{3a}$ is absent and $R^{3b}$ is cyclopropyl or isopropyl; X is C and $Ar^1$ group is 4-phenyl, 6-indolyl or 6-benzothienyl, each optionally substituted with methyl or phenyl.

Also preferred is a compound of formula I wherein q is 1; U is carbon, W is nitrogen forming a pyrazole ring; $R^1$ is chloro or trifluoromethoxy; $R^2$ is hydrogen or chloro; $R^{3a}$ is hydrogen and $R^{3b}$ is cyclopropyl, or isopropyl; X is C and $Ar^1$ group is 4-phenyl, 6-indolyl or 6-benzothienyl, each optionally substituted with methyl or phenyl.

Also preferred is a compound of formula I wherein U is oxygen, and W is carbon forming an isoxazole ring; $R^1$ is chloro or trifluoromethoxy; $R^2$ is hydrogen or chloro; $R^{3a}$ is absent and $R^{3b}$ is cyclopropyl; X is N and $Ar^1$ group is 4-phenyl, 2-pyridinyl, 6-indolyl or 6-benzothienyl each optionally substituted with methyl.

Also preferred is a compound of formula I wherein: U and W are both nitrogen forming a triazole ring; $R^1$ is chloro or trifluoromethoxy; $R^2$ is hydrogen or chloro; $R^{3a}$ is hydrogen and $R^{3b}$ is cyclopropyl or isopropyl; X is N and $Ar^1$ group is 4-phenyl, 6-indolyl or 6-benzothienyl, each optionally substituted with methyl or phenyl.

Also preferred is a compound of formula I wherein: U is carbon, W is nitrogen forming a pyrazole ring; $R^1$ is chloro or trifluoromethoxy; $R^2$ is hydrogen or chloro; $R^{3a}$ is hydrogen and $R^{3b}$ is cyclopropyl, or isopropyl; X is N and $Ar^1$ group is 4-phenyl, 6-indolyl or 6-benzothienyl, each optionally substituted with methyl or phenyl.

The present invention also provides a compound of formula Ia

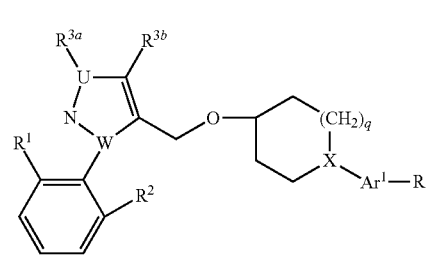

wherein:

q is 1 or 2, provided that when X is C, q is 1;

U is O, N or C; provided that when U is O or N, $R^{3a}$ is absent; and provided that when U is N or C, the UN bond is a double bond; provided that U and W are not simultaneously C; and provided that when W is C, the WN bond is a double bond; and wherein UN and WN are not simultaneously double bonds;

W is C or N;

X is C or N;

$R^1$ is chloro, fluoro, or trifluoromethoxy;

$R^2$ is hydrogen chloro, fluoro, or trifluoromethoxy;

$R^{3a}$ is hydrogen, or absent;

$R^{3b}$ is trifluoromethyl, cyclopropyl or isopropyl;

$Ar^1$ is selected from the group consisting of indolyl, benzothienyl, naphthyl, phenyl, benzoisothiazolyl, indazolyl, and pyridinyl, each optionally substituted with a group selected from the group consisting of methyl, ethyl, and phenyl; and $R^5$ is —COOH; or a pharmaceutically acceptable salt, or enantiomer thereof.

Preferred is a compound of formula I or Ia wherein:

U is O and W is C forming an isoxazole ring:

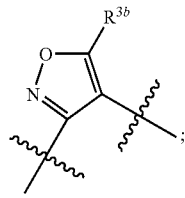

U and W are both N forming a triazole ring:

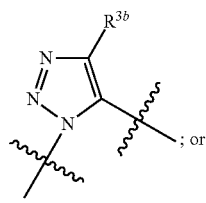

; or or

U is C and W is N forming a pyrazole ring:

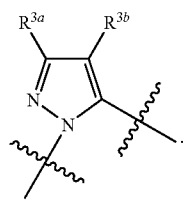

.

The present invention further provides a compound of formula II

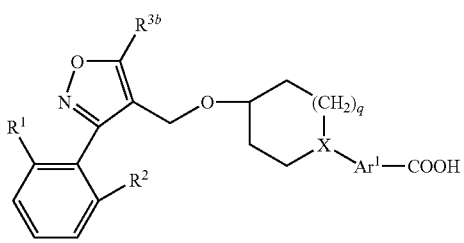

II wherein:
q is 1 or 2;
$R^1$ is chloro, fluoro, or trifluoromethoxy;
$R^2$ is hydrogen chloro, fluoro, or trifluoromethoxy;
$R^{3b}$ is trifluoromethyl, cyclopropyl or isopropyl;
X is C or N, provided that when X is C, q is 1;
$Ar^1$ is selected from the group consisting of indolyl, benzothienyl, naphthyl, phenyl, benzoisothiazolyl, indazolyl, and pyridinyl, each optionally substituted methyl or phenyl;
or a pharmaceutically acceptable salt or enantiomer thereof.

A preferred compound of the invention is a compound of formula I, Ia or II wherein $R^1$ is chloro or trifluoromethoxy and $R^2$ is hydrogen or chloro. Preferably $R^1$ and $R^2$ are both Chloro or $R^1$ is trifluoromethoxy and $R^2$ is hydrogen.

A preferred compound of the invention is a compound of formula I, Ia or II wherein $R^{3b}$ is cyclopropyl or isopropyl. Preferably $R^{3b}$ is cyclopropyl.

A preferred compound of the invention is a compound of formula Ia or II wherein $Ar^1$ is 6-benzoisothiazolyl, 5-benzothienyl, 6-benzothienyl, 6-indazolyl, 5-indolyl or 6-indolyl, 4-phenyl and 2-pyridinyl, each optionally substituted with methyl or phenyl. Preferably $Ar^1$ is 6-benzoisothiazolyl, 5-benzothienyl, 6-benzothienyl, 6-indazolyl, 5-indolyl, 6-indolyl, or 4-phenyl, each optionally substituted with methyl. Most preferably $Ar^1$ group is 5-benzothienyl, 6-benzothienyl, 5-indolyl, 6-indolyl or 4-phenyl, each optionally substituted with methyl.

A preferred compound of the invention is a compound of formula I, Ia or II wherein q is 1 and X is N.

A preferred compound of the invention is a compound of formula I, Ia or II wherein q is 1 and X is C.

A preferred compound of the invention is a compound of formula I, Ia or II wherein q is 2 and X is N.

The compounds of the invention (formula I, Ia or II) may be prepared by the combination of a variety of stepwise procedures known in the art including those described below. Compounds of formula II are prepared according to the schemes below when U=O, $R^{3a}$ is absent, and W is C; or wherein an isoxazole ring is specifically being prepared. The products of each step in the schemes below can be recovered by conventional methods including extraction, evaporation, precipitation, chromatography, filtration, trituration, crystallization, and the like. In the scheme below all substituents, unless otherwise indicated, are as previously defined and suitable reagents are well known and appreciated in the art.

Scheme 1

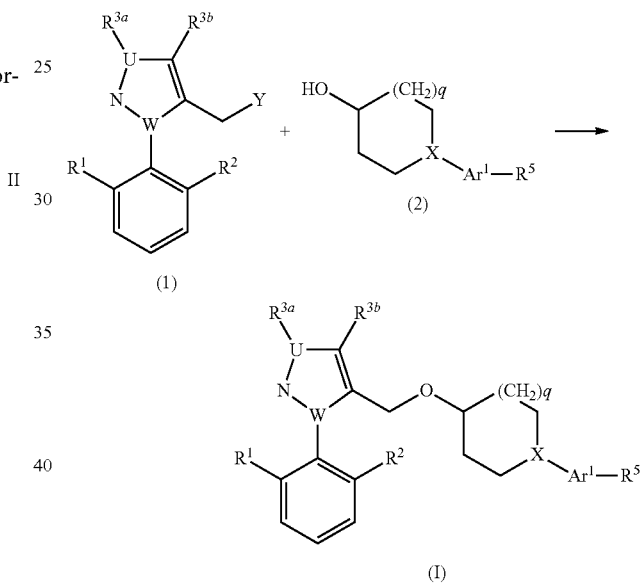

q = 1 or 2

Scheme 1 depicts the reaction of an appropriate compound of formula (1) with an appropriate compound of formula (2) to give a compound of formula I or II where X is N.

Thus, an appropriate compound of formula (1) in which $R^1$, $R^2$, $R^{3a}$, $R^{3b}$, q, and $R^5$ are defined for formula I and Y is a leaving group and an appropriate compound of formula (2) is one in which $R^5$, and $Ar^1$ are as defined in formula (I) or a group which gives rise to $R^5$ as defined in formula (I), for example, by formation of an ester, amide, sulfonamide, or acid are reacted to form the compound of formula (I) with appropriate protections and/or deprotections or other processing steps known to one of skill in the art or disclosed herein. Suitable leaving groups are well-known in the art and include halides, particularly chloro, bromo, and iodo; and sulfonate esters, such as brosyl, tosyl, methanesulfonyl, and trifluoromethane sulfonyl.

For example, a compound of formula (1) is reacted with a compound of formula (2) in a suitable solvent, such as acetonitrile, dimethylformamide, dimethylsulfoxide, tetrahydrofuran, pyridine, methylethyl ketone and the like. As will be readily appreciated an excess of a suitable base such as sodium hydride, potassium carbonate, potassium t-butoxide, sodium carbonate, cesium carbonate, sodium bicarbonate, triethylamine, diisopropylethylamine is usually used in the reaction. Such reactions generally are carried out at temperatures from about room temperature to about the reflux temperature of the chosen solvent and typically use from about 1 to 2 equivalents of the compound of formula (2). In addition, up to about 2 equivalents of a crown ether, 18-crown-6 for example, may be added to facilitate the reaction and a microwave is preferred as heating apparatus when $R^{3b}$=iPr. Compounds wherein $R^5$ is an ester can be converted to compounds of formula (I) wherein $R^5$ is an acid via methods well known to one of ordinary skill in the art. For example, hydrolysis of simple alkyl esters in suitable solvents such as THF, acetonitrile, methanol, ethanol, water mixtures thereof at temperatures from about 25-100° C. with suitable bases including for example, NaOH, LiOH, and KOH. In a modification of this hydrolysis method a microwave apparatus may be used as an energy/heat source, especially when the ester is sterically hindered. For example a laboratory microwave utilizing the lowest power setting at about 125° C. for about 20 minutes in solvent mixtures described above is useful. When $R^5$ is a t-butyl ester the corresponding acid can be formed under acidic conditions well known to those skilled in the art.

In an optional step, a pharmaceutically acceptable salt of a compound of formula (I) or (II) is formed. The formation of pharmaceutically acceptable salts is well known and appreciated in the art. See, e.g., P. Stahl, et al., Handbook of Pharmaceutical Salts: Properties, Selection and Use, (VCHA/Wiley-VCH, 2002; S. M. Berge, et al., "Pharmaceutical Salts," *Journal of Pharmaceutical Sciences*, Vol. 66, No. 1, January 1977.

As will be readily appreciated compounds of formula (1) and (2) can be readily prepared by methods that are well-known and established in the art including methods and procedures similar to those described herein. For example, isoxazole compounds of formula (1) wherein U=O and W=C are prepared by the reaction of optionally substituted benzaldehydes with hydroxylamine in the presence of a suitable base such as triethylamine followed by chlorination with a suitable chlorinating agent, such as N-Chloro succinimide, to afford chloroximes (see for example *J. Med. Chem.* 2000, 43 (16), 2971-2974). Reaction of the chloroximes and an appropriate beta-ketoester under basic conditions with a suitable base, such as triethylamine or sodium methoxide, affords the penultimate isoxazole esters. The isoxazole esters may be reduced to the alcohol compounds of formula (1) with well known methods (e.g. DIBAL-H, LAH) and subsequently converted to a leaving group such as for example, a halide leaving group.

Triazole compounds of formula (1) wherein U=W=N are prepared by the reaction of optionally substituted phenyl azide with an acetylene ester followed by reduction to a protected hydroxy acetylene and optionally conversion to a leaving group.

Pyrazole compounds of formula (1) wherein U=CH and W=N are prepared by the reaction of optionally substituted phenyl hydrazine with a 1,3-diketoester (or an equivalent thereof) followed by reduction and optionally conversion to a leaving group. Compounds of formula (2) are prepared by carbon-nitrogen bond formation/coupling reactions. For example, reaction of an appropriate piperidine derivative with a fluorobenzene under nucleophilic aromatic substitution conditions in suitable solvents such as acetonitrile using a base such as potassium carbonate at temperatures ranging from room temperature to the reflux temperature of the solvent affords a compound of formula 2 wherein X is N; q is 1; and $Ar^1$ is phenyl. Alternatively, appropriate piperidines can be reacted with aryl halides under palladium mediated coupling conditions in solvents such as dioxane at temperatures ranging from room temperature to 120° C. to yield compounds of formula (2). Alternatively, appropriate piperidines can be reacted with aryl halides under copper mediated coupling conditions in solvents such as dimethylsulfoxide at temperatures ranging from 85° C. to 120° C. to yield compounds of formula (2). Also, it is recognized that the steps required to prepare a compound of formula (I) can be carried out in any order including, for example, reaction of a partial compound of formula (2) with a compound of formula (1), such that the later carried out carbon-nitrogen bond formation/coupling reaction provide a compound of formula I. More specifically, a compound of formula (3) can be reacted with a compound of formula (1) as described above to afford compounds of formula (4) which, following deprotection, can be converted to compounds of formula (I) via carbon-nitrogen bond forming reactions with compounds of formula (5) (Scheme 2). Compounds of formula (5) may be purchased or prepared from purchased intermediates. For example, the 6-bromoindole-3-carboxylic acid may be purchased and converted to the methyl or t-butyl ester derivative. The 6-bromoindole-3-carboxylic acid, methyl ester derivative may be employed directly in the coupling reaction with the amine as described herein. The 6-bromoindole-3-carboxylic acid, t-butyl ester derivative may be used in the C—N coupling reaction described herein or preferably, it may be converted to the iodo derivative using for example, NaI and CuI in the presence of a suitable base and solvent using procedures known to one of skill in the art. Alternatively, the methyl ester derivative of 6-bromoindole-3-carboxylic acid may be used as the bromo. A person skilled in the art will recognize that different protecting groups and or different leaving groups may be better suited to particular $Ar^1$ substrates.

Also, one of skill in the art is aware that there are many methods for carbon-nitrogen bond forming reactions including, for example, using copper (I) iodide and a suitable organic base, using a palladium catalyst such as $Pd_2(dba)_3$, in the presence of ligands such as S-Phos, X-Phos, or BINAP, using an inorganic base such as cesium carbonate, and a suitable solvent such as xylene to generate compounds of formula (I).

Scheme 2

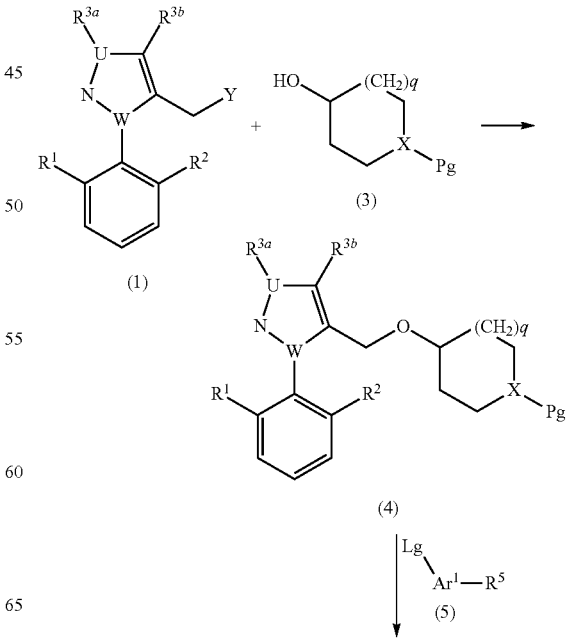

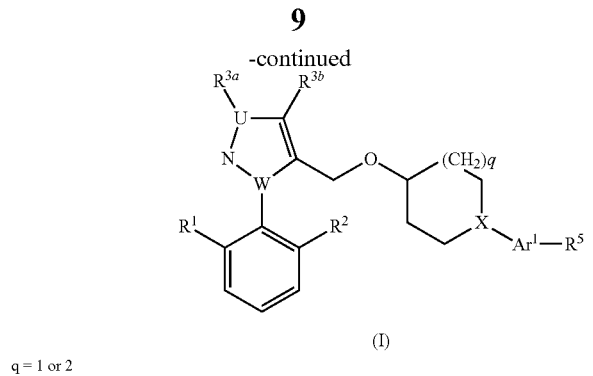

(I)

q = 1 or 2

Compounds of formula 3 wherein q is 2 are generally prepared from the commercially available azepan-4-one or protected derivative thereof. The azepan-4-one is protected for example, as the t-butylcarbamate by reaction with di-t-butyldicarbonate to form the Boc-protected derivative. The protected intermediate is then reduced to the alcohol under conditions well known in the art to afford the compound of formula 3 wherein q is 2. One of skill in the art is able to access compounds of formula 3 following procedures disclosed herein and/or available in applicable reference sources.

Scheme 3 depicts the reaction of an appropriate compound of formula (1) with an appropriate compound of formula (6) to give compounds of formula (I) where X=CH.

Scheme 3

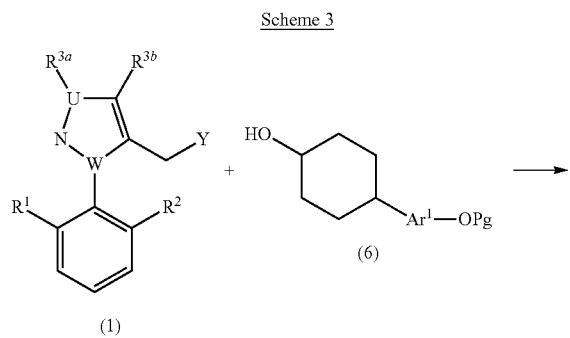

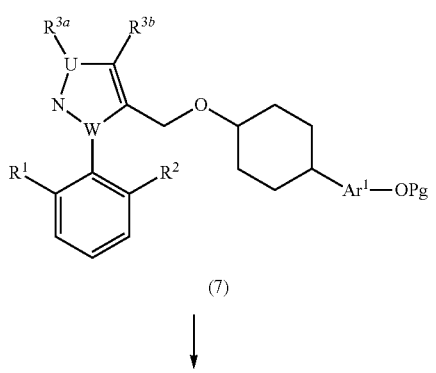

(I)

Thus, an appropriate compound of formula (1) in which $R^1$, $R^2$, $R^{3a}$, $R^{3b}$, q, and $R^5$ are defined for formula (I) and Y is a leaving group and an appropriate compound of formula (6) is one in which $R^5$, X is CH and $Ar^1$ are as defined in formula (I) or a group which gives rise to $R^5$ as defined in formula (I), for example, by formation of an ester or acid are reacted to form the compound of formula (I) with appropriate protections and/or deprotections or other processing steps known to one of skill in the art or disclosed herein. Suitable leaving groups are well-known in the art and include halides, particularly chloro, bromo, and iodo; and sulfonate esters, such as brosyl, tosyl, methanesulfonyl, and trifluoroethanesulfonyl.

For example, a compound of formula (1) is reacted with a compound of formula (6) in a suitable solvent, such as acetonitrile, dimethylformamide, dimethylsulfoxide, tetrahydrofuran, pyridine, methylethyl ketone and the like. As will be readily appreciated, an excess of a suitable base is usually used in the reaction, including sodium hydride, potassium carbonate, potassium t-butoxide, sodium carbonate, cesium carbonate, sodium bicarbonate, triethylamine, diisopropylethylamine. Such reactions generally are carried out at temperatures of about room temperature to about the reflux temperature of the chosen solvent and typically use from about 1 to 2 equivalents of the compound of formula (1).

Additionally, compounds of formula (7) are converted to compounds of formula (I) wherein $R^5$ is an ester. Thus, deprotection of compounds of formula (7) to yield intermediate phenolic compounds followed by reaction with trifluoromethane sulfonic anhydride affords intermediate triflates. Such triflations are typically carried out in dichloromethane with pyridine as base at temperatures from −20° C. to RT. The triflates can then be reacted with carbon monoxide in the presence of palladium acetate and 1,4-bis(diphenylphosphino)butane to give the carbonylated products of formula (I) wherein $R^5$ is an ester.

Additionally, penultimate compounds of formula (I) wherein $R^5$ is an ester can be converted to compounds of formula (I) wherein $R^5$ is an acid or compounds of formula (II) as described above.

In an optional step, a pharmaceutically acceptable salt of a compound of formula (I) is formed. The formation of salts is well known and appreciated in the art.

As will be readily understood compounds of formula (6) can be prepared by methods that are well-known and established in the art including methods and procedures similar to those described herein. Compounds of formula (6) are prepared by carbon-carbon bond formation/coupling reactions. For example, an appropriately substituted cyclohexanone alcohol can be converted to the vinyl triflate under well known conditions and subsequently converted to a vinylboronate. The boronate can then be reacted with arylbromides for example under Suzuki conditions to afford the requisite arylcyclohexenes that can be reduced with hydrogen and catalytic palladium on carbon to afford compounds of formula (6). Also, it is recognized that the steps required to prepare a compound of formula (I) can be carried out in any order including, for example, reaction of a compound of formula (8) with a compound of formula (1). More specifically, a compound of formula (8) can be reacted with a compound of formula (1) as described above to afford compounds of formula (I) where X=CH (Scheme 4). Compounds of formula (8) can be prepared in a similar manner to compounds of formula (6) above.

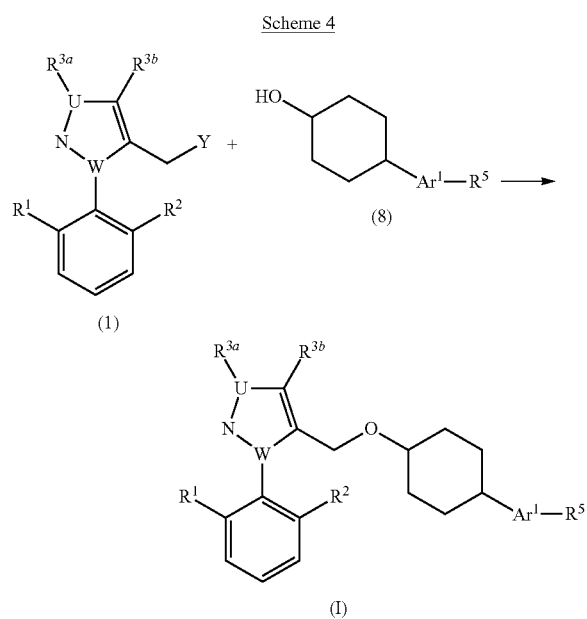

As will be readily understood the steps to prepare the compounds of the invention are dependent upon the particular compound being synthesized, the starting compound, and the relative lability of the substituted moieties. Also contemplated are various protection and deprotection steps as may be required or beneficial for carrying out the reactions above. The selection and use of suitable protecting groups is well known and appreciated in the art (see for example, *Protecting Groups in Organic Synthesis*, Theodora Greene (Wiley-Interscience)).

Certain compounds of the invention exist as solid amorphous or crystalline forms. A compound of the invention may also exist in multiple crystalline forms wherein one or more of the crystalline forms are preferred over others on account of having more desirable properties such as, for example, improved solubility, improved bioavailability and/or improved stability. All such crystalline forms are within the ambit of the present invention Assay The following assay protocols and results demonstrate the utility, in vitro, and in vivo efficacy of the compounds and/or methods of the current invention and are provided for the purpose of illustration and not meant to be limiting in any way.

The following abbreviations used herein are defined as follows. "LDL" is: Low Density Lipoprotein; "HDL" is High Density Lipoprotein; "VLDL" is Very Low Density Lipoprotein; "LDLR−/−" is Low Density Lipoprotein receptor deficient; "DMEM" is Dulbecco's Modified Eagle's Medium; "GAPDH" is glyceraldehyde-3-phosphate dehydrogenase; "NaCMC" is sodium carboxymethylcellulose; "SLS" is sodium lauryl sulfate; "FPLC" is fast protein liquid chromatography; "PBS" is phosphate buffered saline; "VLDL-C" is Very Low Density Lipoprotein-Cholesterol; "HDL-C" is High Density Lipoprotein-Cholesterol; "CMV" is cytomegalovirus. "RT" or "rt" indicates room temperature.

Human FXR/FXR-Response Element Luciferase Reporter Cotransfection Assay

Compounds of the present invention are tested using the Human FXR/FXR-Response Element Luciferase Reporter Cotransfection Assay. The assay is performed essentially as described in *J. Biological Chem.* 2006, 281 (52), 39831-39838, except that 10 μg total DNA per million cells is used. One of skill in the art is able to perform this assay without undue experimentation.

Exemplified compounds of the invention are found to be potent using this assay exhibiting $EC_{50}s$ in the range of about 75 to about 2590 nM. For example, the compound of Example 7 showed an $EC_{50}$ of 220 nM.

FXR-SRC-1 Cofactor Recruitment Assay

Compounds are evaluated by an FXR-SRC-1 Cofactor Recruitment assay using the Alpha (Amplified Luminescent Proximity Homogeneous Assay) Screen technology according to the manufacturer instructions (Perkin Elmer Corporation, Norwalk, Conn., USA) at various concentrations. Mix purified 6-HIS-tagged human FXR ligand-binding domain (amino acids 242-472), purified GST-tagged human SRC-1 nuclear receptor-interacting domain (amino acids 220-394), Nickel Chelate donor beads (Perkin Elmer Corporation) and Anti-GST antibody acceptor beads (Perkin Elmer Corporation) together and aliquot 12 μL per well into 384 well plates. Add compounds in 3 μL per well for a total assay volume of 15 μL and incubate at room temperature in the dark for 4 hours. After incubation, compounds that bind FXR and induce the interaction between the FXR and SRC-1 (available from Invitrogen Corporation Carlsbad, Calif., USA) would bring the two bead types into proximity generating luminescence that is quantified. Calculate $EC_{50}$ values. Exemplified compounds of the invention are found to be effective in the SRC-1 FXR interaction assay with $EC_{50}s$ of about 38-5200 nM. For example, the compound of Example 7 exhibited an $EC_{50}$ of about 325 nM.

LDLR−/− Serum Lipid Modulation

Acclimate animals for two weeks prior to study initiation. Maintain mice on a 12:12 hour light-dark cycle at 21° C. Provide deionized water ad libitum and maintain for two weeks on 'western diet' TD 88137 Diet (42% fat, 0.15% cholesterol, Harlan Teklad, Madison, Wis., USA) ad libitum. Optimize groups of five ten-week-old male LDLR−/− mice based on serum triglyceride and cholesterol levels. Dose groups once daily by oral gavage with various doses of the test compound dissolved in 5% EtOH/5% polyethylene glycol 660 12-hydroxystearate (Solutol® HS 15 (available from Univar, UK, and BASF AG, Germany) in NaCMC (1%), SLS (0.5%), antifoam (0.05%), polyvinylpyrrolidone (0.085%) for seven days. Collect blood by cardiac puncture after asphyxiation in a $CO_2$ chamber. Measure serum triglycerides, glucose, and total cholesterol using standard clinical chemistry instrumentation and reagents. Assay pooled serum samples by FPLC analysis for lipoprotein cholesterol fraction values (VLDL, LDL, and HDL) by separation on a size exclusion column with in-line determination of cholesterol. Separate lipoprotein fractions by FPLC, and quantify cholesterol with an in-line detection system. Apply, 35 μL plasma samples/50 µL pooled sample to a Superose 6 HR 10/30 size exclusion column (Amersham Pharmacia Biotech, Piscataway, N.J., USA) and elute with PBS, pH 7.4 (diluted 1:10), containing 5 mM EDTA, at 0.5 mL/min. Cholesterol reagent (available from Roche Diagnostics, Indianapolis, Ind., USA) at 0.16 mL/min is mixed with the column effluent through a T connection; the mixture is then passed through a 15 m×0.5 mm knitted tubing reactor (Aura Industries, New York, N.Y., USA) immersed in a 37° C. water bath. The colored product produced in the presence of cholesterol is monitored in the flow stream at 505 nm, and the analog voltage from the monitor is converted to a digital signal for collection and analysis. The change in voltage corresponding to change in cholesterol concentration is plotted vs. time, and the area under the curve corresponding to the elution of VLDL-C and HDL-C is calculated using Turbo Chrome® version 4.12F12 software (PerkinElmer Corporation). In this assay, compounds of the invention tested reduce total cholesterol by up to about 87% and triglycerides by up to about 86% when dosed at 10 mg/kg. More specifically, the compound of Example 9 lowers total cholesterol by about 76% and triglycerides by about 75% when dosed at 10 mg/kg.

The specific dose of a compound administered according to this invention will, of course, be determined by the particular circumstances surrounding the case including, for example, the compound administered, the route of administration, the state of being of the patient, and the pathological condition being treated.

The compounds of the present invention are preferably formulated as pharmaceutical compositions administered by a variety of routes. Most preferably, such compositions are for oral administration. Pharmaceutical compositions and processes for preparing same are well known in the art. See, e.g., Remington: The Science and Practice of Pharmacy (A. Gennaro, et al., eds., 20$^{th}$ ed., Lippincott, Williams and Wilkins Publishers, 2003).

The present invention is further illustrated by the examples and preparations disclosed herein. These examples and preparations are illustrative only and are not intended to limit the invention in any way. The terms used in the examples and preparations have their normal meanings unless otherwise designated. All chromatography is performed using silica gel, unless otherwise indicated.

The following abbreviations used herein are defined according to Aldrichimica Acta, Vol 17, No. 1, 1984. Other abbreviations are defined as follows. "MeOH" is methanol; "EtOH" is ethanol; "EtOAc" is ethyl acetate; "hex" is hexane; "DCM" is dichloromethane; "DMEA" is dimethylethylamine; "MTBE" is methyl tertiary-butylether, "Pd$_2$(dba)$_3$" is tris(dibenzylideneacetone)dipalladium(0); "X-Phos" is 2-dicyclohexylphosphino-2',4',6'-triisopropylbiphenyl; "BINAP" is 2,2'-bis(diphenylphosphino)-1,1'binaphthyl; "S-Phos" is 2-dicyclohexyophosphino-2',6'-dimethoxybiphenyl; "NBS" is N-bromosuccinimide; "THF" is tetrahydrofuran; "OAc" is acetate.

All compounds are named using ChemDraw Ultra 7.0 and 10.0 available from CambridgeSoft Corporation, Cambridge, Mass.

Intermediate Preparation 1

[3-(2,6-Dichloro-phenyl)-5-isopropyl-isoxazol-4-yl]-methanol

The title compound is prepared essentially as described in J. Med. Chem. 2000, 43 (16), 2971-2974.

Intermediate Preparation 2

2,6-Dichloro-benzaldehyde oxime 2,6-Dichloro-benzaldehyde (7.0 g, 40 mmol) and hydroxylamine hydrochloride (2.16 g, 44 mmol) are added to 10 mL of water and 30 mL of methanol. Sodium hydroxide (4.0 g, 100 mmol) is dissolved in 8 mL of water slowly. The sodium hydroxide solution is added to the benzaldehyde solution. The reaction is stirred overnight. The reaction mixture is partitioned between ethyl acetate and water. The organic layer is washed with brine and dried over solid sodium sulfate. The organic layer is filtered and the solvent is removed under reduced pressure to yield the title compound.

The following compound is prepared essentially as described in the preparation of 2,6-dichloro-benzaldehyde oxime from the appropriate starting material.

Intermediate Preparation 2A

2-Trifluoromethoxy-benzaldehyde oxime

Intermediate Preparation 3

2,5 Dichlorobenzaldehyde-chloro-oxime

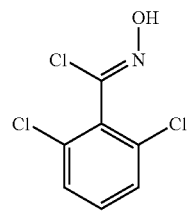

2,6-Dichloro-benzaldehyde oxime (7.6 g, 40 mmol) is dissolved in 56 mL of DMF and N-chlorosuccinimide (5.9 g, 44.0 mmol) is added followed by a catalytic amount of HCl gas. The reaction mixture is stirred overnight. The reaction mixture is partitioned between ether and water. The layers are separated and the ether layer is washed with brine and is dried over sodium sulfate. The ether layer is filtered and the solvent is removed under reduced pressure to yield the crude product. The crude product is purified via chromatography using a gradient of 10% ethyl acetate in hexanes to 15% ethyl acetate in hexanes to yield the title compound. $^1$H-NMR (400 MHz, CDCl$_3$) δ 8.76 (broad, 1H), 7.38-7.26 (m, 3H)

The following compound is prepared essentially as described in the preparation of 2,5 dichlorobenzaldehyde-chloro-oxime from the appropriate starting material.

Intermediate Preparation 3A: 2-Trifluoromethoxy-benzaldehyde chloro-oxime, $^1$H-NMR (400 MHz, CDCl$_3$): δ 8.09 (s, 1H), 7.58 (d, 1H), 7.48 (t, 1H), 7.36-7.31 (m, 2H)

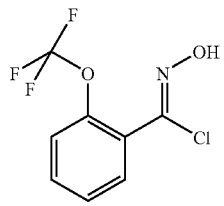

Intermediate Preparation 4

2-Azido-1,3-dichloro-benzene

To a 0° C. solution of 2,6-dichloroaniline (2.00 g) in ethyl acetate (40 mL) is added concentrated hydrochloric acid (12 mL). The reaction is stirred for 10 minutes. To this solution is added a solution of sodium nitrite (2.55 g) in water (7.5 mL) over 3 minutes. Upon completion of the addition, the reaction is stirred for an additional 30 minutes. A solution of sodium azide (2.41 g) in water (8 mL) is added over 5 minutes. After 30 minutes, pH 7 buffer (50 mL) is added and the reaction is transferred to a separatory funnel. The layers are separated and the aqueous layer is extracted with ethyl acetate. The organic layers are combined and washed with brine, dried over sodium sulfate, filtered, and concentrated under reduced pressure to give the title compound (2.11 g). $^1$H NMR (400 MHz, CDCl$_3$) δ 7.3-7.27 (d, 2H), 7.07-7.02 (t, 1H).

The following compound is prepared essentially as described in the preparation of 2-azido-1,3-dichloro-benzene using appropriate starting material.

Intermediate Preparation 4A

1-Azido-2-trifluoromethoxy-benzene

Intermediate Preparation 5

4-Methyl-pent-2-ynoic acid ethyl ester

To a solution of 3-methylbut-1-yne (6.32 g), cooled in a dry-ice/acetone bath, in tetrahydrofuran (200 mL) is added 1.6 M N-butyl lithium solution (63.8 mL). After 1 h, ethyl chloroformate (9.33 mL) is added and the reaction mixture is stirred for an additional 1.5 h. The reaction mixture is allowed to warm to room temperature and is quenched with saturated ammonium chloride solution. The reaction is extracted two times with ethyl acetate. The organic layers are combined, washed with brine, dried over sodium sulfate, filtered, and concentrated under reduced pressure to give the title compound (11.5 g). $^1$H NMR (400 MHz, CDCl$_3$) δ 3.75 (s, 3H), 2.8-2.65 (m, 1H), 1.25-1.23 (d, 6H).

The following compound is prepared essentially as described according to the preparation of 4-methyl-pent-2-ynoic acid ethyl ester using the appropriate starting material.

Intermediate Preparation 5A

Cyclopropyl-propynoic acid methyl ester

Intermediate Preparation 6

4-Methyl-2-oxo-pentanoic acid methyl ester

To a solution of 4-methyl-2-oxo-pentanoic acid (3.4 g, 26 mmol) in methanol (12 mL) and 2,2-dimethoxypropane (48 mL) is added chlorotrimethylsilane (0.38 mL). The reaction mixture is stirred at ambient temperature overnight. The reaction mixture is concentrated under reduced pressure to give the title compound as an oil, (3.8 g, quant.). $^1$H NMR (400 MHz, CDCl$_3$): δ 3.86 (s, 3H), 2.72 (d, 2H), 2.16 (m, 1H), 0.96 (d, 6H).

Intermediate Preparation 7

2-Cyclopropylmethyl-[1,3]dithiane-2-carboxylic acid ethyl ester

To a flamed dried flask is added dry toluene (80 mL) and sodium hydride (60%, 33.5 mmol, 1.34 g). The reaction is cooled in a ice bath and a solution of ethyl 1,3 dithiane carboxylate (52 mmol, 10 g) and bromomethyl cyclopropane (62.4 mmol, 8.42 g) in DMF (24 mL) are added dropwise over 10 minutes. The ice bath is removed and the reaction is stirred for 18 h. Water is added (50 mL) and the organic layer is separated. The organic layer is washed with brine, dried (Na$_2$SO$_4$), and concentrated to a yellow oil (12 g, 92%). LC-ES/MS: 247.0 (M+1).

Intermediate Preparation 8

3-Cyclopropyl-2-oxo-propionic acid ethyl ester

To a 0° C. suspension of NBS (439 mmol, 79 g) in a mixture of acetonitrile (400 mL) and water (100 mL) is added a solution of 2-cyclopropylmethyl-[1,3]dithiane-2-carboxylic acid ethyl ester (73.2 mmol, 18.05 g) in acetonitrile (50 mL) over 15 minutes. The reaction is warmed and stirred at room temperature. After 45 minutes, 500 mL of 1:1 hexane/DCM is added. The layers are separated. The organic layer is washed with saturated Na$_2$SO$_3$ (2×225 mL) and brine (2×225 mL), dried with Na$_2$SO$_4$, filtered, and concentrated under reduced pressure to a residue. The residue is diluted in CCl$_4$ and filtered. The filtrate is concentrated to give the title compound (7 g, 61%). LC-ES/MS: 157.0 (M+1).

Intermediate Preparation 9

3-Cyclopropyl-4-dimethylamino-2-oxo-but-3-enoic acid ethyl ester

A mixture of 3-cyclopropyl-2-oxo-propionic acid ethyl ester (6.4 mmol, 1.0 g) and dimethylformamide dimethylacetal (12.8 mmol, 2.0 mL) are combined and stirred at room temperature for 18 hours. The reaction is concentrated under reduced pressure to yield the title compound (1.38 g, 100%). LC-MS: 212.0 (M+1).

Intermediate Preparation 10

5-Cyclopropyl-3-(2,6-dichloro-phenyl)-isoxazole-4-carboxylic acid methyl ester

3-Cyclopropyl-2-oxo-propionic acid methyl ester (0.55 g, 3.9 mmol) is combined with triethylamine (0.393 g, 3.9 mmol) and is stirred for five minutes. 2,5-Dichlorobenzaldehyde-chloro-oxime (0.88 g, 3.9 mmol) is added and the reaction is stirred overnight. The solvent is removed under reduced pressure and is purified via flash chromatography using a gradient of 1% ethyl acetate in hexanes to 10% ethyl acetate in hexanes to yield the title compound (0.80 g, 66%). $^1$H-NMR (400 MHz, CDCl$_3$) δ 7.37 (d, 2H), 7.31 (t, 1H), 3.66 (s, 3H), 2.88 (m, 1H), 1.38 (m, 2H), 1.25 (m, 2H)

The following compound is prepared essentially as described in the preparation of 5-cyclopropyl-3-(2,6-dichloro-phenyl)-isoxazole-4-carboxylic acid methyl ester from the appropriate starting material Intermediate Preparation 10A: 5-Cyclopropyl-3-(2-trifluoromethoxy-phenyl)-isoxazole-4-carboxylic acid methyl ester, ES/MS m/z: 328.0 (M+1)

Intermediate Preparation 11

3-(2,6-Dichloro-phenyl)-5-isopropyl-3H-[1,2,3]triazole-4-carboxylic acid ethyl ester A solution of 2-azido-1,3-dichloro-benzene (1.0 g) and 4-methyl-pent-2-ynoic acid ethyl ester (1.8 g) in toluene (5 mL) is heated to 120° C. overnight. Two regioisomers are observed in a range of 1:1 to 3:1 in favor of the desired product. The reaction is concentrated under reduced pressure and the residue is purified by flash chromatography, eluting with 5% ethyl acetate in hexanes. $^1$H NMR (400 MHz, CDCl$_3$) δ 7.48 (d, 2H), 7.42 (t, 1H), 4.22 (q, 2H), 3.64 (m, 1H), 1.46 (d, 6H), 1.15 (t, 3H).

The following compound is prepared essentially as described in the preparation of 3-(2,6-dichloro-phenyl)-5-isopropyl-3H-[1,2,3]triazole-4-carboxylic acid ethyl ester from the appropriate starting material Intermediate Preparation 11A 5-Cyclopropyl-3-(2,6-dichloro-phenyl)-3H-[1,2,3]triazole-4-carboxylic acid methyl ester Intermediate Preparation 12

3-(2,6-Dichloro-phenyl)-5-trifluoromethyl-3H-[1,2,3]triazole-4-carboxylic acid ethyl ester A mixture of 2-azido-1,3-dichloro-benzene (25.0 g, 132.9 mmol) and 4,4,4-trifluoro-but-2-ynoic acid ethyl ester (26.5 g, 159.6 mmol) in toluene (30 mL) are heated at 80° C. for 18 h. A large exotherm is observed at 25 minutes. The reaction is removed from heat until exotherm subsides. Two regioisomers are observed in a range of 1:1 to 3:1 in favor of the desired product. The reaction mixture is concentrated under reduced pressure to 51 g of crude material and purified via column chromatography using a gradient of 35-60% DCM in Hexanes to yield the title compound (28 g, 59%). ES/MS m/z 353.0 (M+1).

Intermediate Preparation 13

2-(2,6-Dichloro-phenyl)-4-isopropyl-2H-pyrazole-3-carboxylic acid methyl ester

To a solution of 4-methyl-2-oxo-pentanoic acid methyl ester (3.8 g, 26 mmol) in N,N-dimethylformamide dimethyl acetal (7 mL, 52 mmol) is added p-toluenesulfonic acid monohydrate (30 mg). The mixture is stirred at 80° C. overnight. The reaction mixture is concentrated under reduced pressure to give 3-isopropyl-4-dimethylamino-2-oxo-but-3-enoic acid ethyl ester as an orange oil. To a solution of 3-isopropyl-4-dimethylamino-2-oxo-but-3-enoic acid ethyl ester and 2,6-dichlorophenylhydrazine hydrochloride (2.8 g, 13 mmol) in EtOH (40 mL) is added concentrated HCl (0.5 mL). The mixture is stirred at ambient temperature for 2 h followed by refluxing overnight. The reaction mixture is concentrated and the residue is partitioned between EtOAc and 1N HCl. The organic phase is dried (Na$_2$SO$_4$) and concentrated to a residue. The residue is purified by column chromatography (0-15% EtOAc in hexanes) to give the title compound as an oil (2.2 g, 52%). $^1$H NMR (CDCl$_3$): δ 7.76 (s, 1H), 7.43 (d, 2H), 7.34 (dd, 1H), 3.75 (s, 3H), 3.48 (m, 1H), 1.32 (d, 6H).

Intermediate Preparation 14

4-Cyclopropyl-2-(2,6-dichloro-phenyl)-2H-Pyrazole-3-carboxylic acid ethyl ester

To a solution of 3-cyclopropyl-4-dimethylamino-2-oxo-but-3-enoic acid ethyl ester (6.5 mmol, 1.4 g) in ethanol (25 mL) is added 2,6-dichlorophenyl hydrazine hydrochloride (7.2 mmol, 1.5 g) followed by concentrated HCl (100 µL). The reaction is stirred for 4 h at room temperature followed by heating at 85° C. for 18 h. The reaction mixture is adsorbed onto silica gel and purified using a gradient of 0-20% EtOAc/Hexanes to yield the title compound (0.8 g, 34%). LC-ES/MS m/e 325.0 (M+1).

Intermediate Preparation 15

(5-Cyclopropyl-3-(2,6-dichloro-phenyl)-isoxazol-4-yl)-methanol

5-Cyclopropyl-3-(2,6-dichloro-phenyl)-isoxazole-4-carboxylic acid methyl ester (0.80 g, 2.6 mmol) is dissolved in 8 mL of THF and is cooled in an ice bath. To the solution is added 1M DIBAL solution in toluene (5.66 mL) and the reaction is stirred one hour. Additional 1M DIBAL solution in toluene (5.66 mL) is added and the reaction is stirred for an additional hour. Upon completion, the reaction is quenched with methanol and acidified with aqueous HCl solution (1M). The reaction mixture is extracted with ethyl acetate and washed with brine. The organic layer is dried over sodium sulfate, filtered, and concentrated under reduced pressure to yield the title compound (0.68 g, 93%). MS m/z: 284.0 (M$^+$+1)

The following compounds are prepared essentially as described in the preparation of (5-cyclopropyl-3-(2,6-dichloro-phenyl)-isoxazol-4-yl)-methanol from the appropriate starting material Intermediate Preparation 15A: (5-Cyclopropyl-3-(2-trifluormethoxy-phenyl)-isoxazol-4-yl)-methanol, $^1$H NMR (400M Hz, CDCl$_3$) δ 7.56-7.49 (2H), 7.38 (t, 2H), 4.60 (s, 2H), 2.15 (m, 1H), 1.23 (m, 2H), 1.14 (m, 2H);

Intermediate Preparation 15B: (5-isopropyl-3-(2-trifluormethoxy-phenyl)-isoxazol-4-yl)-methanol, $^1$H NMR (400M Hz, CDCl$_3$) δ 7.56-7.49 (2H), 7.38 (t, 2H), 4.60 (s, 2H), 2.15 (m, 1H), 1.23 (m, 2H), 1.14 (m, 2H);

Intermediate Preparation 15C: [3-(2,6-Dichloro-phenyl)-5-isopropyl-3H-[1,2,3]triazol-4-yl]-methanol, ES/MS m/z 284 (M+0), 286 (M+2); mp: 154-155° C.;

Intermediate Preparation 15D: [5-Cyclopropyl-3-(2,6-dichloro-phenyl)-3H-[1,2,3]triazol-4-yl]-methanol, ES/MS m/z: 284.0 (M+0), 286.0 (M+2);

Intermediate Preparation 15E: [3-(2,6-Dichloro-phenyl)-5-trifluoromethyl-3H-[1,2,3]triazol-4-yl]methanol, ES/MS m/z 312.0 (M+1);

Intermediate Preparation 15F: [2-(2,6-Dichloro-phenyl)-4-isopropyl-2H-pyrazol-3-yl]-methanol, $^1$H NMR (400 MHz, CDCl$_3$): δ 7.67 (s, 1H), 7.44 (d, 2H), 7.34 (dd, 1H), 4.45 (s, 2H), 3.00 (m, 1H), 1.32 (d, 6H).

Intermediate Preparation 16

[4-Cyclopropyl-2-(2,6-dichloro-phenyl)-2H-pyrazol-3-yl]-methanol

To a 0° C. mixture of LAH powder in THF (20 mL) is added a solution of 4-cyclopropyl-2-(2,6-dichloro-phenyl)-2H-pyrazole-3-carboxylic acid ethyl ester (2.4 mmol, 0.8 g) in THF (10 mL). The reaction is stirred for 2 h at 0° C. The reaction is quenched with a sequence of water (0.26 mL), 5N NaOH (0.26 mL) and water (0.78 mL). The reaction mixture is stirred for 1 h at 0° C. The reaction mixture is filtered and the filtrate is adsorbed onto silica gel and purified using a gradient of 30-50% EtOAc/Hexanes to yield the title compound (0.36 g, 53%). LC-ES/MS m/e 283.0 (M+1).

Intermediate Preparation 17

4-Bromomethyl-3-(2,6-dichloro-phenyl)-5-isopropyl-isoxazole

To a solution of [3-(2,6-dichloro-phenyl)-5-isopropyl-isoxazol-4-yl]-methanol (1.14 g, 4 mmol) in THF (20 mL) is added $PBr_3$ (0.76 mL, 8 mmol). The reaction mixture is stirred at reflux for 30 minutes. The reaction mixture is diluted with EtOAc and washed with 0.2 N HCl. The organic layer is separated, dried ($MgSO_4$), filtered, and concentrated under reduced pressure to give the title compound as an oil.

Intermediate Preparation 18

4-Bromomethyl-5-cyclopropyl-3-(2,6-dichloro-phenyl)-isoxazole

To a 0° C. solution of (5-cyclopropyl-3-(2,6-dichloro-phenyl)-isoxazol-4-yl)-methanol (0.124 g, 0.44 mmol) in dichloromethane (4 mL) is added phosphorous tribromide (0.261 g, 0.963 mmol). The ice bath is removed after 20 minutes and the reaction is allowed to stir for an additional twenty minutes at room temperature. The reaction is quenched with pH 7 buffer and is extracted with dichloromethane several times. The organic layers are combined, washed with brine, and dried over sodium sulfate. The reaction is filtered and concentrated under reduced pressure to yield the title compound (0.124 g, 82%). $^1$H-NMR (400 MHz $CDCl_3$) δ 7.45-7.33 (m, 3H), 4.20 (s, 2H), 2.09 (m, 1H), 1.27 (m, 2H), 1.16 (m, 2H)

Intermediate Preparation 19

4-Bromomethyl-5-cyclopropyl-3-(2-trifluoromethoxy-phenyl)-isoxazole

To a solution of (5-cyclopropyl-3-(2-trifluormethoxy-phenyl)-isoxazol-4-yl)-methanol (2.19 g, 7.32 mmol) in anhydrous methylene chloride (50 mL) at 0° C. is added $PBr_3$ (0.83 mL, 8.7 mmol) and the mixture is stirred for 3 hours. The mixture is then poured into 100 mL of ice water and extracted with DCM (2×). The combined DCM layers are washed with brine, dried ($MgSO_4$) and concentrated under reduced pressure to provide crude residue. The residue is purified via flash chromatography (120 g silica) eluting with a gradient of 0 to 60% ethyl acetate in heptane to provide the title compound (2.1 g, 79%) as an oil.

Intermediate Preparation 19a

5-Bromomethyl-1-(2,6-dichlorophenyl)-4-isopropyl-1H-pyrazole

To a solution of (1-(2,6-dichlorophenyl)-4-isopropyl-1H-pyrazol-5-yl)methanol (4.0 g, 0.014 mol) in $CH_2Cl_2$ (50 ml) is added phosphorus tribromide (5.69 g, 0.021 mol) at 0° C. Stir the mixture for 3 h at room temperature. Dilute with water and extract with ethyl acetate. Concentrate under reduced pressure, to give crude product, which is purified by column chromatography over silica gel eluting with 7:3 hexane/ethyl acetate to give 0.50 g (10%) of the title compound. ES/MS m/e ($^{81}$Br) 348.93 [M+H]$^+$.

Intermediate Preparation 20

4-Bromomethyl-5-isopropyl-3-(2-trifluoromethoxy-phenyl)-isoxazole

To a solution of [5-isopropyl-3-(2-trifluoromethoxy-phenyl)-isoxazol-4-yl]-methanol (3.0 g, 10.0 mmol) in methylene chloride (20 mL) is added triphenyl phosphine (4.0 g, 15.6 mmol) followed by N-bromosuccinimide (2.8 g, 15.6 mmol). The reaction is stirred for 2 hours at room temperature. The reaction is concentrated under reduced pressure and the residue is purified via flash chromatography using a gradient of 20-40% EtOAc in hexanes.

The following compounds are prepared essentially as described in the preparation of 4-bromomethyl-5-isopropyl-3-(2-trifluoromethoxy-phenyl)-isoxazole using the appropriate starting material.

Intermediate Preparation 20A: 5-Bromomethyl-1-(2,6-dichloro-phenyl)-4-isopropyl-1H-[1,2,3]triazole;

Intermediate Preparation 20B: 5-Bromomethyl-4-cyclopropyl-1-(2,6-dichloro-phenyl)-1H-[1,2,3]triazole;

Intermediate Preparation 20C: 5-Bromomethyl-1-(2,6-dichloro-phenyl)-4-trifluoromethyl-1H-[1,2,3]triazole, ES/MS m/z 373.0 (M+1);

Intermediate Preparation 20D: 5-Bromomethyl-1-(2,6-dichloro-phenyl)-4-isopropyl-1H-pyrazole;

Intermediate Preparation 20E: 5-Bromomethyl-4-cyclopropyl-1-(2,6-dichloro-phenyl)-1H-pyrazole.

Intermediate Preparation 20F

5-Bromomethyl-1-(2,6-dichlorophenyl)-4-isopropyl-1H-[1,2,3]triazole

To a solution of (1-(2,6-dichlorophenyl)-4-isopropyl-1H-1,2,3-triazol-5-yl)methanol (3.0 g, 0.01048 mol) and $CBr_4$ in $CH_2Cl_2$ (15 ml) is added a solution of triphenylphosphine (3.50 g, 0.01334 mol) in $CH_2Cl_2$ (10 ml) at 0° C. Stir the solution for 4 h at room temperature and concentrate in vacuo to give crude product. Purify by column chromatography over silica gel eluting with 7:3 hexane/ethyl acetate to give 3.0 g (82%) of the title compound. ES/MS m/e ($^{79}$Br/$^{81}$Br) 348/350 [M+H]$^+$.

Intermediate Preparation 21

2-Bromo-4-fluoro-benzoic acid methyl ester

To a solution of thionyl chloride (2.6 mL, 35.7 mmol) in methanol (500 mL) at 0° C. is added 4-fluoro-2-bromo benzoic acid (5.18 g, 23.6 mmol). The mixture is heated to reflux for 19 h. The mixture is concentrated and purified via flash chromatography on silica (120 g) using a gradient of 0 to 80% ethyl acetate in heptane to provide the title compound (2.06 g, 37%) as an oil. MS m/z 233.0 (M+1)

The following compounds are prepared essentially as described in the preparation of 2-bromo-4-fluoro-benzoic acid methyl ester using the appropriate starting material.

Intermediate Preparation 21A: 4-Fluoro-naphthalene-1-carboxylic acid methyl ester, $^1$H NMR (400 MHz, CDCl$_3$) δ 9.00 (d, 1H), 8.17 (m, 2H), 7.60 (m, 2H), 7.12 (m, 1H), 3.98 (s, 3H);

Intermediate Preparation 21B: 4-Fluoro-2-methyl-benzoic acid methyl ester, $^1$H NMR (400 MHz, CDCl$_3$) δ 7.92 (m, 1H), 6.90 (m, 2H), 3.84 (s, 3H), 2.59 (s, 3H).

Intermediate Preparation 22

2-Bromo-4-(4-hydroxy-piperidin-1-yl)-benzoic acid methyl ester

A mixture of 2-bromo-4-fluoro-benzoic acid methyl ester (2.06 g, 8.84 mmol), 4-hydroxy piperidine (1.86 g, 18.4 mmol), and potassium carbonate (1.33 g, 9.62 mmol) in acetonitrile (25 mL) is heated to 90° C. for 17 h. The mixture is concentrated and partitioned between ethyl acetate and water. The solvent layers are separated and the aqueous layer is extracted with ethyl acetate (3×). The combined ethyl acetate layers are dried (MgSO$_4$), filtered, and concentrated under reduced pressure. The residue is purified on silica (120 g) using a gradient of 0% to 90% ethyl acetate in heptane to provide the title compound (2.10 g, 76%) LC-ES/MS m/z 314.0 (M+1)

The following compounds are prepared essentially as described in the preparation of 2-bromo-4-(4-hydroxy-piperidin-1-yl)-benzoic acid methyl ester using the appropriate starting material.

Intermediate Preparation 22A: 4-(4-Hydroxy-piperidin-1-yl)-benzoic acid ethyl ester, LC-ES/MS m/z 250.2 (M+1);

Intermediate Preparation 22B: 4-(4-Hydroxy-piperidin-1-yl)-benzoic acid methyl ester, LC-ES/MS m/z 236.2 (M+1);

Intermediate Preparation 22C: 4-(4-Hydroxy-piperidin-1-yl)-naphthalene-1-carboxylic acid, LC-ES/MS m/z 286.0 (M+1);

Intermediate Preparation 22D: 4-(4-Hydroxy-piperidin-1-yl)-2-methyl-benzoic acid methyl ester, LC-ES/MS m/z 250.2 (M+1).

Intermediate Preparation 23

5-(4-Hydroxy-piperidin-1-yl)-biphenyl-2-carboxylic acid methyl ester

A mixture of 2-bromo-4-(4-hydroxy-piperidin-1-yl)-benzoic acid methyl ester (1.2 g, 3.82 mmol), phenylboronic acid (800 mg; 6.56 mmol), potassium phosphate, tribasic, monohydrate (1.3 g, 10.7 mmol), and tetrakis(triphenylphosphine)palladium (500 mg, 0.433 mmol) in 1,2-dimethoxyethane (25 mL) and water (1 mL) is heated to 90° C. under a nitrogen atmosphere for 24 h. The mixture is concentrated and partitioned between ethyl acetate and water. The solvent layers are separated and the aqueous layer is extracted with ethyl acetate (3×). The combined ethyl acetate layers are dried (MgSO$_4$), filtered, and concentrated under reduced pressure. The residue is purified on silica (120 g) eluting with a gradient of 0% to 100% ethyl acetate in heptane to provide the desired product (1.09 g, 92%) as a gummy residue. LC-ES/MS m/z 312.0 (M+1)

Intermediate Preparation 24

4-(4-Hydroxy-piperidin-1-yl)-3-methyl-benzoic acid methyl ester

A mixture of 4-hydroxypiperidine (2.65 g, 25.4 mmol), methyl 4-bromo-3-methylbenzoate (5.00 g, 21.8 mmol), (R)-(+)-2,2'-bis(diphenylphosphino)-1,1'-binaphthyl (1.37 g, 2.17 mmol), palladium acetate (0.247 g, 1.10 mmol), cesium carbonate (21.5 g, 65.3 mmol) in 1,4-dioxane (100 mL) is heated in a 350 mL pressure vessel for 18 h at 80° C. under nitrogen and then at 120° C. for 4 h. The mixture is filtered and concentrated under reduced pressure. The residue is purified on silica (120 g) using a gradient of 0 to 90% ethyl acetate in heptane to provide the title compound (2.4 g, 44%). LC-ES/MS m/z 250.2 (M+1)

Intermediate Preparation 25

6-(4-Hydroxy-piperidin-1-yl)-1-methyl-1H-indole-3-carboxylic acid methyl ester

A re-sealable tube is charged with 6-bromo-1-methyl-1H-indole-3-carboxylic acid methyl ester (850 mg, 1.00 equiv, 3.17 mmol), 4-hydroxypiperidine (491 mg, 1.5 equiv, 4.76 mmol), copper(I) iodide (60.379 mg, 0.1 equiv, 0.32 mmole), proline (73 mg, 0.2 equiv, 0.64 mmol) and potassium carbonate (885 mg, 2 equiv, 6.34 mmol) and purged with nitrogen. Anhydrous dimethyl sulfoxide (2 mL) is added. The tube is closed and the mixture is stirred at 110° C. for 22 h. The mixture is allowed to reach room temperature and aqueous saturated NH$_4$Cl is added. The mixture is extracted with EtOAc (2×). The organic layers are combined, washed with water, dried over anhydrous sodium sulfate, filtered and concentrated under reduced pressure. The residue is purified via chromatography (40 g silica) eluting with a gradient of 20% to 100% ethyl acetate/hexane to provide the title compound (540 mg, 59%) as a white solid. ES/MS m/z 289.0 (M+1)

The following list of compounds is prepared essentially as described in the preparation of 6-(4-hydroxy-piperidin-1-yl)-1-methyl-1H-indole-3-carboxylic acid methyl ester using the appropriate starting material.

Intermediate Preparation 25A: 6-(4-Hydroxy-piperidin-1-yl)-benzo[b]thiophene-3-carboxylic acid ethyl ester, ES/MS m/z 306.0 (M+1);

Intermediate Preparation 25B: 4-(4-Hydroxy-azepan-1-yl)-benzoic acid ethyl ester, ES/MS m/z 264.0 (M+1).

Intermediate Preparation 26

4-Hydroxy-3,4,5,6-tetrahydro-2H-[1,2']bipyridinyl-5'-carboxylic acid methyl ester To a solution of methyl 6-chloronicotinate (890 mg, 1.00 equiv; 5.03 mmol) in dry DMF (30 mL) is added 4-hydroxypiperidine (1.5 equiv; 7.55 mmol; 778.95 mg) and triethylamine (1.05 mL; 1.5 equiv; 7.55 mmol). The system is flushed with N$_2$ and heated at 80° C. for 4.5 h. The reaction is allowed to reach room temperature and is diluted with water/EtOAc. The aqueous layer is extracted with ethyl acetate (3×). The organic layer is washed with brine, dried over MgSO$_4$, filtered, and concentrated under reduced pressure. The crude residue is purified via chromatography eluting with hexane/EtOAc 2:1 to 1:2 to yield an orange solid. The solid is triturated with hexane/EtOAc 4:1 and filtered to provide the title compound (1.023 g, 86%) as a white solid. ES/MS m/z 237.0 (M+1)

Intermediate Preparation 27

4-Oxo-azepane-1-carboxylic acid tert-butyl ester

To a solution of azepan-4-one (9.57 g, 64 mmol) in 1,4-dioxane (70 mL) is added di-t-butyldicarbonate (15.8 g, 70.4 mmol). The mixture is stirred at room temperature and a slurry of sodium carbonate (4.11 g, 38.4 mmol) in 40 mL of water is added. The mixture is heated to 80° C. for 2 h. The mixture is concentrated and extracted with ethyl acetate (3×). The combined ethyl acetate layers are dried ($Na_2SO_4$) and concentrated under reduced pressure. The residue is purified on silica using a gradient of ethyl acetate in hexanes (25 to 50%) to provide the title compound (13.6 g, 99.7%).

Intermediate Preparation 28

4-Hydroxy-azepane-1-carboxylic acid tert-butyl ester

To a solution of 4-oxo-azepane-1-carboxylic acid tert-butyl ester (13.6 g, 63.8 mmol) in methanol (10 mL) and tetrahydrofuran (30 mL) at 0° C. is added lithium borohydride (1.40 g, 63.8 mmol). The mixture is stirred at 0° C. for 60 minutes. Hydrochloric acid (1.0 M, 40 mL) is added. The mixture is concentrated under reduced pressure and extracted with ethyl acetate (2×). The combined ethyl acetate layers are dried ($Na_2SO_4$) and concentrated to a residue. The residue is purified on silica using a gradient of ethyl acetate in hexanes (40 to 80%) to yield the title compound (13.6 g, 99.1%).

Intermediate Preparation 29

4-[5-Cyclopropyl-3-(2,6-dichloro-phenyl)-isoxazol-4-ylmethoxy]-azepane-1-carboxylic acid tert-butyl ester To a solution of 4-hydroxy-azepane-1-carboxylic acid tert-butyl ester (1.88 g, 8.73 mmol) in anhydrous THF (15 mL) at 0° C. is added 18-crown-6 (2.3 g, 8.70 mmol) and tert-butyl alcohol, potassium derivative (8.8 mL, 1.0 M, 8.80 mmol). The mixture is stirred at room temperature for 20 minutes following which 4-bromomethyl-5-cyclopropyl-3-(2,6-dichloro-phenyl)-isoxazole (1.8 g, 5.19 mmol) in THF is added over 2 minutes. The mixture is stirred for 2 h and water (10 mL) is added. The mixture is concentrated under reduced pressure and extracted with ethyl acetate (3×). The combined ethyl acetate layers are dried ($MgSO_4$), concentrated, and purified via flash chromatography (120 g silica) eluting with a gradient of ethyl acetate in heptane (0 to 60%) to provide the title compound (420 mg, 17%).

The following compounds are made essentially as described in preparation 29.

Intermediate Preparation 29A: tert-Butyl 4-((5-cyclopropyl-3-(2-(trifluoromethoxy)phenyl)isoxazol-4-yl)methoxy) azepane-1-carboxylate, For this compound, the reaction mixture is stirred for 12 h after adding all reagents. ES/MS m/z 497.24 (M+1).

Intermediate Preparation 29B: tert-Butyl 4-((1-(2,6-dichlorophenyl)-4-isopropyl-1H-1,2,3-triazol-5-yl)methoxy)azepane-1-carboxylate. For this compound heat the mixture to 40° C. in a microwave for one hour after adding all reagents. ES/MS m/z 483.12 (M+1).

Intermediate Preparation 29C: tert-Butyl 4-((1-(2,6-dichlorophenyl)-4-isopropyl-1H-pyrazol-5-yl)methoxy) azepane-1-carboxylate. For this compound heat the mixture to 40° C. in a microwave for one hour after adding all reagents. ES/MS m/z 482.17 (M+1).

Intermediate Preparation 30

4-[3-(2,6-Dichloro-phenyl)-5-ethyl-isoxazol-4-ylmethoxy]-azepanium; chloride Cold 4M aq. hydrogen chloride in dioxane is added to 4-[5-cyclopropyl-3-(2,6-dichloro-phenyl)-isoxazol-4-ylmethoxy]-azepane-1-carboxylic acid tert-butyl ester (370 mg, 0.769 mmol) and the mixture is stirred at room temperature for 1 h. The mixture is concentrated under reduced pressure to provide the title compound (350 mg, 109%). ES/MS m/z 381.0 (M+1, free base).

Intermediate Preparation 30A

4-((Azepan-4-yloxy)methyl)-5-cyclopropyl-3-(2,6-dichlorophenyl)isoxazole

To a solution of 4-[5-cyclopropyl-3-(2,6-dichloro-phenyl)-isoxazol-4-ylmethoxy]-azepane-1-carboxylic acid tert-butyl ester (2.0 g, 0.00416 mol) in $CH_2Cl_2$ (20 ml) is added trifluoroacetic acid (1.42 g, 0.01248 mol) at 0° C. under $N_2$ atmosphere. Stir the mixture for 3 h at room temperature. Concentrate the reaction mixture in vacuo to give crude product. Purify by column chromatography over alumina (neutral) eluting with 8:2 dichloromethane/methanol to give the title compound 1.4 g (88%). ES/MS m/z 381.1 (M+1).

The following compounds are made essentially as described in the preparation of intermediate Preparation 30a.

Intermediate Preparation 30B: 4-((Azepan-4-yloxy)methyl)-5-cyclopropyl-3-(2-(trifluoromethoxy)phenyl)isoxazole, ES/MS m/z 397.20 (M+1).

Intermediate Preparation 30C: 4-((1-(2,6-Dichlorophenyl)-4-isopropyl-1H-1,2,3-triazol-5-yl)methoxy)azepane, ES/MS m/z 383.14 (M+1).

Intermediate Preparation 30D: 4-((1-(2,6-Dichlorophenyl)-4-isopropyl-1H-pyrazol-5-yl)methoxy)azepane, ES/MS m/z 382.13 (M+1).

Intermediate Preparation 31

Trans-4-[4-(4-Methoxy-benzyloxy)-phenyl]-cyclohexanol

To a suspension of p-(trans-4-hydroxycyclohexyl)phenol (67.62 mmol, 13.00 g) in acetone (400 mL) is added 1-bromomethyl-4-methoxybenzene (74.38 mmol, 10.57 mL) and potassium carbonate (81.14 mmol, 11.33 g). The mixture is stirred for 64 h at room temperature and filtered. The filtrate is concentrated and recrystallized from $CH_2Cl_2$ (100 mL) to give the title compound (15.1 g, 71%) as a white solid. $^1H$ NMR (400 MHz, $CDCl_3$): 1.34-1.49 (m, 4H), 1.87-1.90 (m, 2H), 2.02-2.07 (m, 2H), 2.38-2.45 (m, 1H), 3.61-3.68 (m, 1H), 3.79 (s, 3H), 4.93 (s, 2H), 6.88 (d, 2H, J=8.8 Hz), 6.89 (d, 2H, J=8.8 Hz), 7.09 (d, 2H, J=8.8 Hz), 7.32 (d, 2H, J=8.8 Hz).

Intermediate Preparation 32

Trifluoro-methanesulfonic acid 4-(tert-butyl-dimethyl-silanyloxy)-cyclohex-1-enyl ester To a solution of 4-(tert-butyl-dimethyl-silanyloxy)-cyclohexanone (2.63 g, 11.5 mmol) and N-phenylbis(trifluoromethanesulphonimide) (6.26 g, 17.3 mmol) in THF (50 mL) at −78° C. is added lithium bis(trimethylsilyl)amide (16.1 mL, 1.0 M) dropwise over 10 minutes. The mixture is stirred and allowed to warm to room temperature over 60 minutes. The reaction is quenched with brine (25 mL) and concentrated under reduced pressure. The residue is extracted with EtOAc (2×50 mL). The combined organic layers are dried over $Na_2SO_4$, filtered, and concentrated. The crude product is purified by flash chromatography eluting with 10% EtOAc/Hexanes to afford the title compound (3.82 g, 92%). MS m/z 361.0 (M+1).

Intermediate Preparation 33

2-[4-(tert-Butyl-dimethyl-silanyloxy)-cyclohex-1-enyl]-4,4,5,5-tetramethyl-[1,3,2]dioxaborolane A flask containing a solution of trifluoro-methanesulfonic acid 4-(tert-butyl-dimethyl-silanyloxy)-cyclohex-1-enyl ester (3.82 g, 10.6 mmol) and bis(pinacolato)diboron (3.02 g; 11.7 mmol) in 1,4-dioxane (50 mL) is evacuated and refilled with $N_2$ three times. (1,1'-bis(diphenylphosphino)ferrocene) palladium(II) chloride (177 mg), 1,1'-bis(diphenylphosphino)ferrocene (606 mg), and potassium acetate (2.101 g) are added. The mixture is stirred for 18 h at 85° C. The mixture is cooled to room temperature, filtered through a pad of diatomaceous earth, and concentrated under reduced pressure. The residue is purified by silica gel chromatography eluting with a gradient of 5-10% EtOAc/Hexanes to give the title compound (2.21 g, 61.6%). $^1H$ NMR (400 MHz, $CDCl_3$): δ 6.40 (t, 1H), 4.12-4.07 (m, 1H), 2.35-2.27 (m, 2H), 2.14-2.02 (m, 2H), 1.79-1.74 (m, 1H), 1.53-1.44 (m, 1H), 1.22 (s, 12H), 0.86 (s, 9H), 0.03 (s, 3H), 0.02 (s, 3H).

Intermediate Preparation 34

6-[4-(tert-Butyl-dimethyl-silanyloxy)-cyclohex-1-enyl]-1-methyl-1H-indole-3-carboxylic acid methyl ester A flask containing a solution of 2-[4-(tert-butyl-dimethyl-silanyloxy)-cyclohex-1-enyl]-4,4,5,5-tetramethyl-[1,3,2]dioxaborolane (1.40 g, 4.14 mmol) and 6-bromo-1-methyl-1H-indole-3-carboxylic acid methyl ester (1.22 g, 4.55 mmol) in toluene (50 mL) is evacuated and filled with $N_2$ three times. Potassium phosphate (1.79 g, 8.27 mmol), $Pd(OAc)_2$ (46 mg), and 2-dicyclohexylphosphino-2',6'-dimethoxy-1,1'-biphenyl (S-Phos, 50 mg) are added. The mixture is stirred at 100° C. for 16 h and cooled to room temperature. The mixture is filtered through a pad of diatomaceous earth, and the filtrate is concentrated under reduced pressure. The residue is purified by silica gel chromatography eluting with 25% EtOAc/Hexanes to provide the title compound (0.71 g, 43%). MS m/z 400.3 (M+1).

Intermediate Preparation 35

6-(4-Hydroxy-cyclohex-1-enyl)-1-methyl-1H-indole-3-carboxylic acid methyl ester

A solution of 6-[4-(tert-butyl-dimethyl-silanyloxy)-cyclohex-1-enyl]-1-methyl-1H-indole-3-carboxylic acid methyl ester (0.710 g, 1.78 mmol) in THF (10 mL) is treated with $Bu_4NF$ (2.22 mL, 1.0 M in THF). The mixture is stirred at room temperature for 5 h and concentrated under reduced pressure. The residue is purified by silica gel chromatography eluting with a gradient of 25-80% EtOAc/Hexanes to provide the 6-(4-hydroxy-cyclohex-1-enyl)-1-methyl-1H-indole-3-carboxylic acid methyl ester (0.320 g, 63%). MS m/z 286.3 (M+1).

Intermediate Preparation 36

6-(4-Hydroxy-cyclohexyl)-1-methyl-1H-indole-3-carboxylic acid methyl ester

A solution of 6-(4-hydroxy-cyclohex-1-enyl)-1-methyl-1H-indole-3-carboxylic acid methyl ester (0.251 g, 0.880 mmol) in tetrahydrofuran (10 mL) is added to a slurry of palladium (0.200 g, 5% in carbon) in THF (2 mL). The mixture is stirred under an atmosphere of hydrogen (balloon) at room temperature for 12 h. The mixture is filtered through a pad of diatomaceous earth and concentrated under reduced pressure to yield the title compound (0.202 g, 80%). MS m/z 288.3 (M+1)

Intermediate Preparation 37

Trans-5-Cyclopropyl-3-(2,6-dichloro-phenyl)-4-{4-[4-(4-methoxy-benzyloxy)-phenyl]-cyclohexyloxymethyl}-isoxazole 4-[4-(4-Methoxy-benzyloxy)-phenyl]-cyclohexanol (2.24 mmol, 700.00 mg) and 18-crown-6 (2.69 mmol, 710.70 mg) in tetrahydrofuran (10 mL) is treated with tert-butyl alcohol, potassium derivative (2.69 mmol, 2.69 mL; 1M in THF). The mixture is stirred for 30 minutes and 4-bromomethyl-5-cyclopropyl-3-(2,6-dichloro-phenyl)-isoxazole (3.36 mmol, 1.17 g) is added. The mixture is stirred at room temperature for 5 minutes and heated to 40° C. for 1.5 h. Silica gel is added and the reaction mixture is concentrated under reduced pressure. The crude mixture is purified by silica gel flash chromatography eluting with a gradient of 10-60% EtOAc in hexanes. A second chromatography is performed on silica gel eluting with 0.5% EtOAc in DCM to yield the title compound (960 mg, 74%). MS m/z 577.9 (M+1).

The following compound is prepared essentially as described in the preparation of trans-5-cyclopropyl-3-(2,6-dichloro-phenyl)-4-{4-[4-(4-methoxy-benzyloxy)-phenyl]-cyclohexyloxymethyl}-isoxazole using the appropriate starting material.

Intermediate Preparation 37A: 5-Cyclopropyl-4-{4-[4-(4-methoxy-benzyloxy)-phenyl]-cyclohexyloxymethyl}-3-(2-trifluoromethoxy-phenyl)-isoxazole, ES/MS m/z 594.0 (M+1)

Intermediate Preparation 38

Trans-4-{4-[5-Cyclopropyl-3-(2,6-dichloro-phenyl)-isoxazol-4-ylmethoxy]-cyclohexyl}-phenol Trans-5-cyclopropyl-3-(2,6-dichloro-phenyl)-4-{4-[4-(4-methoxy-benzyloxy)-phenyl]-cyclohexyloxymethyl}isoxazole (1.33 mmol, 770.00 mg) in dichloromethane (17 mL) is treated at room temperature with methoxybenzene (13.3 mmol, 1.45 mL) and trifluoroacetic acid (8.5 mL). The solution is stirred for 2 h and concentrated under reduced pressure. The residue is co-evaporated with $CCl_4$ (2×) and triturated with hexanes. The crude product is supported on silica gel and purified by flash chromatography (120 g silica) eluting with a gradient of 20-50% EtOAc in hexane to give the title compound (544 mg, 89%) as a white solid. MS m/z 458.0 (M+1).

The following compound is prepared essentially as described in the preparation of trans-4-{4-[5-cyclopropyl-3-(2,6-dichloro-phenyl)-isoxazol-4-ylmethoxy]-cyclohexyl}-phenol using the appropriate starting material.

Intermediate Preparation 38A: 4-{4-[5-Cyclopropyl-3-(2-trifluoromethoxy-phenyl)-isoxazol-4-ylmethoxy]-cyclohexyl}-phenol, ES/MS m/z 474.3 (M+1).

Intermediate Preparation 39

Trans-Trifluoro-methanesulfonic acid 4-{4-[5-cyclopropyl-3-(2,6-dichloro-phenyl)-isoxazol-4-yl-methoxy]-cyclohexyl}-phenyl ester Trans-4-{4-[5-cyclopropyl-3-(2,6-dichloro-phenyl)-isoxazol-4-ylmethoxy]-cyclohexyl}phenol (1.16 mmol, 534.00 mg) is dissolved in dichloromethane (15 mL) and pyridine (5.82 mmol, 471.02 µL). The solution is cooled in an ice bath and trifluoromethanesulfonic anhydride (1.46 mmol, 245.43 µL) is added. The mixture is stirred for 1.5 h and concentrated under reduced pressure. The residue is diluted with EtOAc (75 mL) and washed sequentially with 1N NaOH (25 mL), brine (15 mL), 10% aqueous citric acid (2×30 mL), and brine (25 mL). The organic layer is dried ($Na_2SO_4$), filtered, and concentrated under reduced pressure. The crude mixture is purified by flash chromatography (120 g silica) eluting with a gradient of 15-40% EtOAc/hexane to give the title compound (616 mg, 90%) as a colorless oil. MS m/z 589.8 (M+1).

The following compound is prepared essentially as described in the preparation of trans-trifluoro-methanesulfonic acid 4-{4-[5-cyclopropyl-3-(2,6-dichloro-phenyl)-isoxazol-4-ylmethoxy]-cyclohexyl}-phenyl ester using the appropriate starting material.

Intermediate Preparation 39A: Trifluoro-methanesulfonic acid 4-{4-[5-cyclopropyl-3-(2-trifluoromethoxy-phenyl)-isoxazol-4-ylmethoxy]-cyclohexyl}-phenyl ester, $^1$H NMR (400 MHz, $CDCl_3$): δ 7.58-7.55 (dd, 1H, J=1.8 Hz, 8 Hz), 7.49-7.46 (dd, 1H, J=1.8 Hz, 8 Hz), 7.38-7.34 (m, 2H), 7.21-7.19 (d, 2H, J=8.8 Hz), 7.15-7.13 (d, 2H, J=8.8 Hz), 4.38 (s, 2H), 3.24-3.19 (m, 1H), 2.49-2.44 (m, 1H), 2.17-2.10 (m, 1H), 1.99-1.96 (m, 2H), 1.87-1.84 (m, 2H), 1.41-1.20 (m, 6H), 1.10-1.07 (m, 2H).

Intermediate Preparation 40

6-Bromo-1H-indole-3-carboxylic acid methyl ester

To a solution of 6-bromoindole-3-carboxylic acid (960 mg, 4.00 mmol) in methanol (9.5 mL) is added (trimethylsilyl) diazomethane (2.0 M solution in hexanes, about 9 mL) over two minutes at room temperature. The yellow mixture is concentrated under reduced pressure. The residue is re-dissolved in methanol and concentrated under reduced pressure. This process is repeated several times to give the title compound as a solid (100%). ES/MS m/e 256.0 (M+2).

Intermediate Preparation 40A-1

Methyl 6-bromobenzo[d]isothiazole-3-carboxylate

To a solution of 6-bromobenzo[d]isothiazole-3-carboxylic acid (1.0 g, 3.89 mmol) in methanol (15 mL), thionyl chloride (0.92 g, 7.74 mmol) is added slowly at room temperature and the solution is stirred at 80° C. for 14 h. Cool the mixture to room temperature and concentrate to give 1.0 g (95%) of the title compound as a light brown solid. $^1$H NMR (400 MHz, MeOD) δ 4.04 (s, 3H), 7.73 (dd, J=8.8, 1.6 Hz, 1H), 8.41 (s, 1H), 8.61 (d, J=8.8 Hz, 1H).

The following compounds are made essentially as described in the preparation of Intermediate Preparation 40A-1, methyl 6-bromobenzo[d]isothiazole-3-carboxylate.

| Prep No. | Name | 1H NMR (400 MHz) |
|---|---|---|
| 40B | Methyl 4-bromo-2-methylbenzoate | ($CDCl_3$) δ 2.57 (s, 3H), 3.88 (s, 3H), 7.37 (dd, J = 8.0, 1.6 Hz, 1H)), 7.41 (d, J = 1.6 Hz, 1H), 7.78 (d, J = 8.4 Hz, 1H) |
| 40C | Methyl 5-bromo-1-methyl-1H-indole-2-carboxylate | (MeOD) δ 3.31 (s, 3H), 3.92 (s, 3H), 7.12 (s, 1H), 7.33-7.38 (m, 2H), 7.80 (s, 1H) |
| 40D | Methyl 6-bromo-1-methyl-1H-indole-2-carboxylate | (MeOD) δ 3.31 (s, 3H), 3.92 (s, 3H), 7.15 (s, 1H), 7.19 (dd, J = 8.4, 1.2 Hz, 1H), 7.56 (d, J = 8.8 Hz, 1H), 7.62 (s, 1H) |

Intermediate Preparation 41

6-Bromo-1-methyl-1H-indole-3-carboxylic acid methyl ester

To a mixture of 6-bromo-1H-indole-3-carboxylic acid methyl ester (100 mg, 0.394 mmol), potassium carbonate (163 mg, 1.18 mmol) in DMF is added iodomethane (30 µL, 0.47 mmol). The reaction mixture is stirred for 1.5 h. Additional iodomethane (10 µL) is added and the reaction is stirred for 30 minutes. The reaction mixture is diluted with dichloromethane and filtered. The filtrate is concentrated under high vacuum, diluted with ethyl acetate, and concentrated to give the title compound (105 mg, 99%). ES/MS m/e 270.0 (M+2).

Intermediate Preparation 41A-1

Ethyl 5-bromo-1-methyl-1H-indole-2-carboxylate

In dimethylformamide (5 mL), combine ethyl 5-bromo-1H-indole-2-carboxylate (1.00 g, 13.7 mmole), potassium carbonate (1.4 g, 10 mmole), and methyl iodide (280 µL, 4.50 mmole). Heat the mixture to 50° C. for 18 hours. Cool to room temperature and partition between EtOAc and water. Extract with EtOAc (3×), wash with brine (3×), dry ($MgSO_4$) and concentrate to provide crude material. The crude material is purified on 120 g silica gel with 0 to 50% EtOAc in heptane to give 850 mg (81%) of the title compound. ES/MS m/e ($^{81}$Br) 284.0 $(M+H)^+$.

Intermediate Preparation 41B

Methyl 6-bromo-1-methyl-1H-indazole-3-carboxylate

To a mixture of methyl 6-bromo-1H-indazole-3-carboxylate (0.50 g, 1.96 mmol) and potassium carbonate (1.28 g, 9.29 mmol) in acetonitrile (15 mL) is added methyl iodide (1.31 g, 9.29 mmol) at room temperature. The reaction mixture is stirred at room temperature for 15 h. Remove the solvent under vacuum, dilute with water, and extract with ethyl acetate (3×10 mL). The combined organics are dried over sodium sulfate and concentrated under reduced pressure. The crude is purified by flash chromatography eluting with 8:2 hexane/ethyl acetate to give 0.35 g (70%) of the title compound as an off white solid. $^1$H NMR (400 MHz, CDCl$_3$) δ 4.03 (s, 3H), 4.14 (s, 3H), 7.42 (dd, J=8.4, 1.2 Hz, 1H), 7.66 (s, 1H), 8.08 (d, J=8.8 Hz, 1H).

The following compound is prepared essentially as described in the preparation of Intermediate Preparation 41B, Methyl 6-bromo-1-methyl-1H-indazole-3-carboxylate. Intermediate Preparation 41C: Methyl 5-bromo-1-methyl-1H-indole-2-carboxylate, (400 MHz, CDCl$_3$) δ 3.91 (s, 3H), 4.06 (s, 3H), 7.21 (d, J=0.8 Hz, 1H), 7.27 (s, 1H), 7.42 (dd, J=8.8, 1.6 Hz, 1H), 7.80 (d, J=1.6 Hz, 1H).

Intermediate Preparation 42

6-Bromo-benzo[b]thiophene-3-carboxylic acid

The title compound is prepared essentially as described in J. Med. Chem. 2003, 46, 2446-2455.

Preparation 43

6-Bromo-benzo[b]thiophene-3-carboxylic acid ethyl ester

Approach 1

A solution of 6-Bromo-benzo[b]thiophene-3-carboxylic acid (65 g, 252.8 mmole) and sulfuric acid (0.10 equiv; 25.3 mmol, 1.35 mL; 2.48 g) in ethanol (1.0 L) is heated at 65° C. for 3 days. The solution is cooled to room temperature. The resulting light brown precipitate is filtered. The filter cake is washed with methanol to afford the title compound (32 g, 44%).

Approach 2

Oxalyl chloride (717.2 g, 5.65 mol, 3.5 eq) is added to a 0-5° C. suspension of dichloromethane (3.44 L) and aluminum chloride (753.4 g, 5.65 mol, 3.5 eq). The resulting suspension is stirred for 30-60 minutes at 0-5° C. and cooled −20 to −25° C. A solution of 6-bromobenzo[b]thiophene (344 g, 1.614 mol, 1 eq) in dichloromethane (1.72 L) is added over 1 h while maintaining the temperature at −20 to −25° C. The reaction mixture is stirred for 30 minutes at −20 to −25° C. and warmed to 18 to 20° C. using a warm water bath. The reaction mixture is stirred for 1.5 h at this temperature. The reaction mixture is filtered and the filter cake is washed with dichloromethane (3×300 mL). The combined filtrate is concentrated to yield a thick black oil in the flask (600 g). This residue is dissolved in dichloromethane (1 L) and added to ethanol (3.5 L) at −10 to 0° C. in portions at such rate to maintain temperature at 10 to 20° C. Once the addition is complete, the reaction mixture is partially concentrated to remove the dichloromethane only and then the vacuum is released. The reaction mixture is heated to 60-70° C. and stirred at this temperature for 1 h. Upon completion of the reaction, the solution is decanted from the resulting tars. The tars are discarded. The ethanol solution is evaporated to a residue. The residue is diluted with EtOAc (2 L).

At this point, the current reaction mixture is combined with reaction mixture from another batch of the reaction for further work up (started with 330 g of 6-Bromobenzo[b]thiophene, 1.549 mol). The combined reaction mixture is poured into a stirred mixture of EtOAc (1 L) and brine solution (10 L). The layers are separated and the organic layer is washed with brine solution (2 L). The combined aqueous layer is extracted with EtOAc (4 L). The organic layer is washed with brine solution (1 L). The combined organic layers are dried over magnesium sulfate and charcoal, filtered, and concentrated under reduced pressure. The resulting oil is further concentrated in a vacuum oven for 15 h at room temperature to afford waxy solids after drying (750 g). The solids are suspended in heptane (5 L) with stirring and the suspension is heated to 70° C. Magnesium sulfate (300 g) is added and the resulting suspension is stirred for 10 minutes at 70° C. The suspension is filtered. The solids are suspended in heptane (5 L) and heated to 70° C. The suspension is stirred for 10-20 minutes at this temperature and filtered. The filter cake is washed with heptane (1 L). The heptane filtrates are collected and concentrated under reduced pressure to give light brown solids (550 g). The solids are dissolved in heptane (4 L) at 60° C. The resulting solution is cooled to 35 to 50° C. The solution is evenly loaded onto two plugs of silica gel (1.5 kg each) eluting with 0.5% EtOAc in heptane. The pure product fractions are combined and concentrated under reduced pressure. The impure product fractions are combined, concentrated, and purified as described above. The total purified product is isolated (500 g) and crystallized from heptane (1.2 L). The solids are collected by filtration, washed with cold heptane (200 mL, −20° C.), and dried in a vacuum oven at room temperature for 15 h to afford the title compound (460 g, 51%). GC analysis 98.8%; $^1$H NMR (DMSO-d6, 500 MHz): δ 8.65 (s, 1H), 8.36 (d, 1H, J=1.5), 8.33 (d, 1H, J=8.5), 7.63 (dd, 1H, J=2, 8.5), 4.33 (q, 2H, J=7), 1.33 (t, 3H, J=6.5).

EXAMPLES

Example 1

5-{4-[5-Cyclopropyl-3-(2,6-dichloro-phenyl)-isoxazol-4-ylmethoxy]-piperidin-1-yl}-biphenyl-2-carboxylic acid

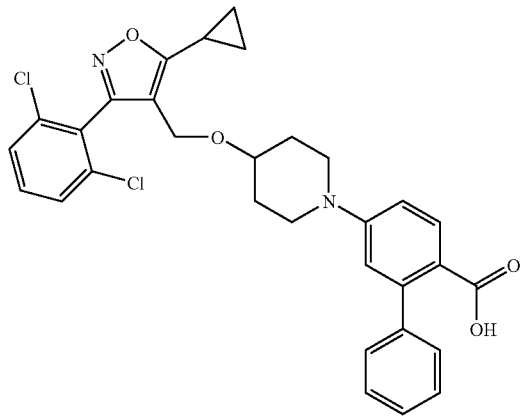

Step 1

5-{4-[5-Cyclopropyl-3-(2,6-dichloro-phenyl)-isoxazol-4-ylmethoxy]-piperidin-1-yl}-biphenyl-2-carboxylic acid methyl ester

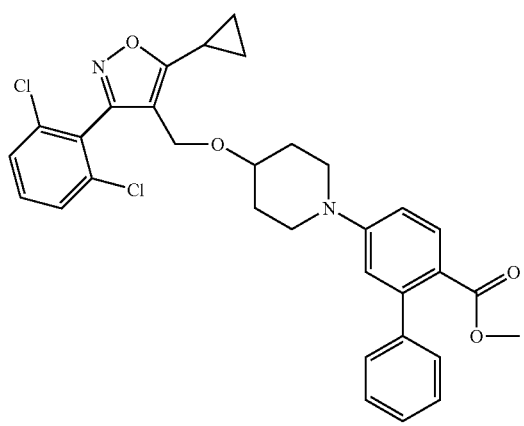

A mixture of 5-(4-hydroxy-piperidin-1-yl)-biphenyl-2-carboxylic acid methyl ester (318 mg, 1.02 mmol), 4-bromomethyl-5-cyclopropyl-3-(2,6-dichloro-phenyl)-isoxazole (375 mg, 1.08 mmol), and sodium hydride (52 mg, 1.30 mmol) in dimethylformamide (4 mL) is stirred at room temperature for 2.5 h. The mixture is partitioned between saturated aqueous ammonium chloride and ethyl acetate. The layers are separated and the aqueous layer is extracted with ethyl acetate (3×). The ethyl acetate layers are washed with brine (3×), dried (MgSO$_4$), and concentrated under reduced pressure. The crude material is purified on silica (40 g) eluting with a gradient of ethyl acetate in heptane (0-60%) to provide the title compound (245 mg, 42%) as a glassy film. LC-ES/MS m/z 579.2 (M+1).

Step 2

5-{4-[5-Cyclopropyl-3-(2,6-dichloro-phenyl)-isoxazol-4-ylmethoxy]-piperidin-1-yl}-biphenyl-2-carboxylic acid A mixture of 5-{4-[5-cyclopropyl-3-(2,6-dichloro-phenyl)-isoxazol-4-ylmethoxy]-piperidin-1-yl}-biphenyl-2-carboxylic acid methyl ester (240 mg, 416 μmoles) in THF (4 mL), MeOH (4 mL) and 5.0 M NaOH (2.0 mL) is heated at 70° C. for 4 h. The mixture is cooled to room temperature and 5 M HCl (2.0 mL) is added. The mixture is concentrated to dryness. A small amount of MeOH is added and the product is precipitated by adding water. The title compound (200 mg, 85%) is collected by vacuum filtration. LC-ES/MS m/z 564.0 (M+1).

The compounds listed in table 1 are prepared essentially as described in the preparation of 5-{4-[5-cyclopropyl-3-(2,6-dichloro-phenyl)-isoxazol-4-ylmethoxy]-piperidin-1-yl}-biphenyl-2-carboxylic acid using the appropriate starting material.

TABLE 1

| Ex No | Name | Data |
| --- | --- | --- |
| 2 | 5-{4-[5-Cyclopropyl-3-(2-trifluoromethoxy-phenyl)-isoxazol-4-ylmethoxy]-piperidin-1-yl}-biphenyl-2-carboxylic acid | LC-ES/MS m/z 579.2 (M + 1) |
| 3 | 5-{4-[3-(2,6-Dichloro-phenyl)-5-isopropyl-isoxazol-4-ylmethoxy]-piperidin-1-yl}-biphenyl-2-carboxylic acid | LC-ES/MS m/z 567.0 (M + 1) |
| 4 | 4-{4-[3-(2,6-Dichloro-phenyl)-5-isopropyl-isoxazol-4-ylmethoxy]-piperidin-1-yl}-naphthalene-1-carboxylic acid | LC-ES/MS m/z 540.0 (M + 1) |
| 5 | 4-{4-[5-Cyclopropyl-3-(2,6-dichloro-phenyl)-isoxazol-4-ylmethoxy]-piperidin-1-yl}-3-methyl-benzoic acid | LC-ES/MS m/z 503.0 (M + 1) |
| 6 | 4-{4-[5-Isopropyl-3-(2-trifluoromethoxy-phenyl)-isoxazol-4-ylmethoxy]-piperidin-1-yl}-benzoic acid | LC-ES/MS m/z 505.0 (M + 1) |
| 7 | 4-{4-[5-Cyclopropyl-3-(2,6-dichloro-phenyl)-isoxazol-4-ylmethoxy]-piperidin-1-yl}-benzoic acid | LC-ES/MS m/z 488.0 (M + 1) |
| 8 | 4-{4-[5-Cyclopropyl-3-(2-trifluoromethoxy-phenyl)-isoxazol-4-ylmethoxy]-piperidin-1-yl}-2-methyl-benzoic acid | LC-ES/MS m/z 517.2 (M + 1) |
| 9 | 4-{4-[5-Cyclopropyl-3-(2,6-dichloro-phenyl)-isoxazol-4-ylmethoxy]-piperidin-1-yl}-2-methyl-benzoic acid | LC-ES/MS m/z 501.0 (M + 1) |
| 10 | 4-{4-[3-(2,6-Dichloro-phenyl)-5-isopropyl-isoxazol-4-ylmethoxy]-piperidin-1-yl}-2-methyl-benzoic acid | LC-ES/MS m/z 504.0 (M + 1) |
| 11 | 4-{4-[3-(2,6-Dichloro-phenyl)-5-isopropyl-isoxazol-4-ylmethoxy]-piperidin-1-yl}-benzoic acid | LC-ES/MS m/z 490.0 (M + 1) |
| 12 | 4-{4-[5-Cyclopropyl-3-(2,6-dichloro-phenyl)-3H-[1,2,3]triazol-4-ylmethoxy]-piperidin-1-yl}-benzoic acid | LC-ES/MS m/z 489.0 (M + 1) |
| 13 | 4-{4-[3-(2,6-Dichloro-phenyl)-5-isopropyl-3H-[1,2,3]triazol-4-ylmethoxy]-piperidin-1-yl}-benzoic acid | LC-ES/MS m/z 490.0 (M + 1) |
| 14 | 4-{4-[3-(2,6-Dichloro-phenyl)-5-trifluoromethyl-3H-[1,2,3]triazol-4-ylmethoxy]-piperidin-1-yl}-benzoic acid* | ES/MS m/z 513.0 (M − 1) |
| 15 | 4-{4-[2-(2,6-Dichloro-phenyl)-4-isopropyl-2H-pyrazol-3-ylmethoxy]-piperidin-1-yl}-benzoic acid | LC-ES/MS m/e 489.3 (M + 1) |
| 16 | 4-{4-[4-Cyclopropyl-2-(2,6-dichloro-phenyl)-2H-pyrazol-3-ylmethoxy]-piperidin-1-yl}-benzoic acid | LC-ES/MS m/e 487.0 (M + 1) |

*Example 14 involves the use of LiOH in place of NaOH for hydrolysis in step 2.

Example 17

6-{4-[3-(2,6-Dichloro-phenyl)-5-isopropyl-isoxazol-4-ylmethoxy]-piperidin-1-yl}-1-methyl-1H-indole-3-carboxylic acid

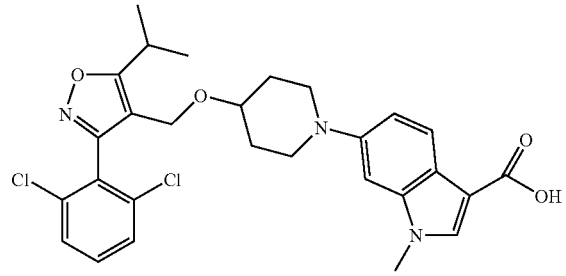

Step 1

6-{4-[3-(2,6-Dichloro-phenyl)-5-isopropyl-isoxazol-4-ylmethoxy]-piperidin-1-yl}-1-methyl-1H-indole-3-carboxylic acid methyl ester

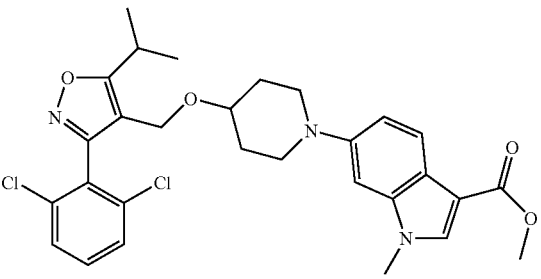

Sodium hydride (60%, 93 mg, 1.2 equiv, 2.3 mmole) is added at room temperature under nitrogen atmosphere to a solution of 6-(4-hydroxy-piperidin-1-yl)-1-methyl-1H-indole-3-carboxylic acid methyl ester (557 mg, 1.00 equiv, 1.93 mmole), tetra-n-butylammonium iodide (73 mg, 0.1 equiv, 193 μmoles) and 4-bromomethyl-3-(2,6-dichloro-phenyl)-5-isopropyl-isoxazole (674 mg, 1 equiv, 1.93 mmole) in anhydrous tetrahydrofuran (6 mL). The reaction mixture is stirred for 6 h. Aqueous saturated NH₄Cl is added and the resulting aqueous solution is extracted with ethyl acetate. The organic layers are combined, dried over anhydrous sodium sulfate, filtered, and concentrated under reduced pressure. The residue is purified via flash chromatography (40 g silica) eluting with a gradient of ethyl acetate:hexane (10% to 100%) to provide the title compound as a white solid (205 mg, 19%). ES/MS m/z 556.0 (M+1)

Step 2

6-{4-[3-(2,6-Dichloro-phenyl)-5-isopropyl-isoxazol-4-ylmethoxy]-piperidin-1-yl}-1-methyl-1H-indole-3-carboxylic acid A solution of 2N lithium hydroxide (0.9 mL, 5 equiv, 1.8 mmole) is added to a solution of 6-{4-[3-(2,6-dichloro-phenyl)-5-isopropyl-isoxazol-4-ylmethoxy]-piperidin-1-yl}-1-methyl-1H-indole-3-carboxylic acid methyl ester (200 mg, 1.00 equiv, 0.36 mmole) in 1,4-dioxane (4 mL). The mixture is stirred at 90° C. for 24 h. The organic solvent is removed, HCl (1M) is added to adjust the pH to 3-4, and the resulting aqueous solution is extracted with dichloromethane. The organic layers are combined, dried over anhydrous sodium sulfate, filtered, and concentrated under reduced pressure. The residue is purified via flash chromatography (12 g silica) eluting with a gradient of ethyl acetate in hexane (10% to 100%) to provide the title compound as a pale brown solid (168 mg, 86%). ES/MS m/z 542.0 (M+1).

The compounds listed in table 2 are prepared essentially as described in the preparation of 6-{4-[3-(2,6-dichloro-phenyl)-5-isopropyl-isoxazol-4-ylmethoxy]-piperidin-1-yl}-1-methyl-1H-indole-3-carboxylic acid using the appropriate starting material.

TABLE 2

| Ex No | Name | Data |
| --- | --- | --- |
| 18 | 6-{4-[3-(2,6-Dichloro-phenyl)-5-isopropyl-isoxazol-4-ylmethoxy]-piperidin-1-yl}-benzo[b]thiophene-3-carboxylic acid | ES/MS m/z 545.0 (M + 1) |
| 19 | 6-{4-[5-Cyclopropyl-3-(2-trifluoromethoxy-phenyl)-isoxazol-4-ylmethoxy]-piperidin-1-yl}-1-methyl-1H-indole-3-carboxylic acid | ES/MS m/z 556.0 (M + 1) |
| 20 | 6-{4-[5-Cyclopropyl-3-(2,6-dichloro-phenyl)-isoxazol-4-ylmethoxy]-piperidin-1-yl}-benzo[b]thiophene-3-carboxylic acid | ES/MS m/z 543.0 (M + 1) |
| 21 | 4-[5-Cyclopropyl-3-(2,6-dichloro-phenyl)-isoxazol-4-ylmethoxy]-3,4,5,6-tetrahydro-2H-[1,2']bipyridinyl-5'-carboxylic acid, | ES/MS m/z 488.0 (M + 1) |
| 22 | 4-{4-[3-(2,6-Dichloro-phenyl)-5-isopropyl-isoxazol-4-ylmethoxy]-piperidin-1-yl}-3-methyl-benzoic acid | ES/MS m/z 503.0 (M + 1) |

Example 23

6-{4-[5-Cyclopropyl-3-(2,6-dichloro-phenyl)-isoxazol-4-ylmethoxy]-piperidin-1-yl}-1-methyl-1H-indole-3-carboxylic acid

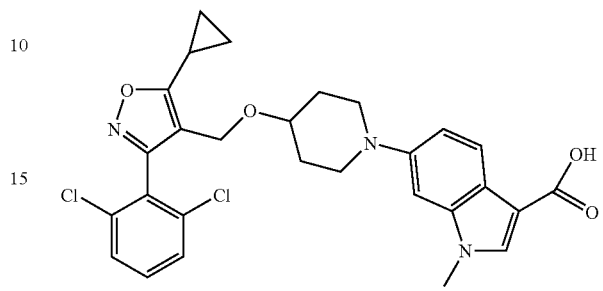

Step 1

6-{4-[5-Cyclopropyl-3-(2,6-dichloro-phenyl)-isoxazol-4-ylmethoxy]-piperidin-1-yl}-1-methyl-1H-indole-3-carboxylic acid methyl ester

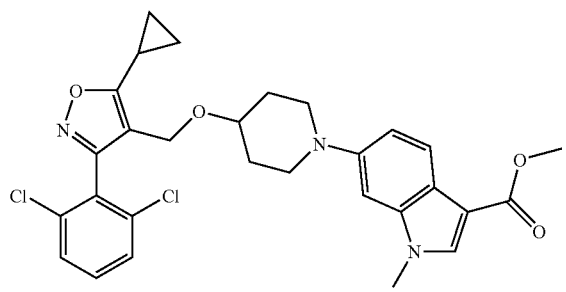

Tetrahydrofuran (4 mL) is added at room temperature to a mixture of 18-crown-6 (306 mg, 1.14 mmole), tert-butyl alcohol, potassium derivative (134 mg, 1.14 mmole) and 6-(4-hydroxy-piperidin-1-yl)-1-methyl-1H-indole-3-carboxylic acid methyl ester (300 mg, 1.040 mmole). The mixture is stirred for 15 minutes and then 4-bromomethyl-5-cyclopropyl-3-(2,6-dichloro-phenyl)-isoxazole (361 mg, 1.04 mmole) is added. After 1.5 h, a saturated solution of NH₄Cl is added and extracted with ethyl acetate. The organic layers are combined, dried over anhydrous sodium sulfate, filtered and the solvent is removed under reduced pressure. The residue is purified via flash chromatography (12 g silica) eluting with a gradient of hexane:ethyl acetate from 20% to 100% to provide the title compound (196 mg, 34%) as a white solid. ES/MS m/z 554.0 (M+1)

Step 2

6-{4-[5-Cyclopropyl-3-(2,6-dichloro-phenyl)-isoxazol-4-ylmethoxy]-piperidin-1-yl}-1-methyl-1H-indole-3-carboxylic acid A solution of 2M lithium hydroxide (1.2 mL, 2.46 mmol) is added to a solution of 6-{4-[5-cyclopropyl-3-(2,6-dichloro-phenyl)-isoxazol-4-ylmethoxy]-piperidin-1-yl}-1-methyl-1H-indole-3-carboxylic acid methyl ester (195 mg, 351.7

μmoles) in 1,4-dioxane (5 mL) and the mixture is stirred at 80° C. overnight. The organic solvent is removed and HCl (1M) is added until the solution reaches pH 3-4. The solid is filtered and washed with water and acetonitrile to provide the title compound (165 mg, 87%) as a white solid. ES/MS m/z 540.0 (M+1).

Example 24

4-{4-[5-Cyclopropyl-3-(2,6-dichloro-phenyl)-isoxazol-4-ylmethoxy]-azepan-1-yl}-benzoic acid, isomer A

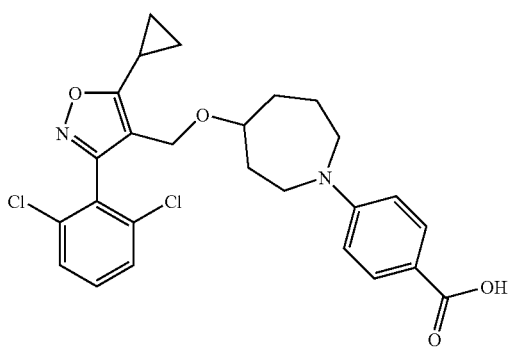

Step 1

4-{4-[5-Cyclopropyl-3-(2,6-dichloro-phenyl)-isoxazol-4-ylmethoxy]-azepan-1-yl}-benzoic acid ethyl ester

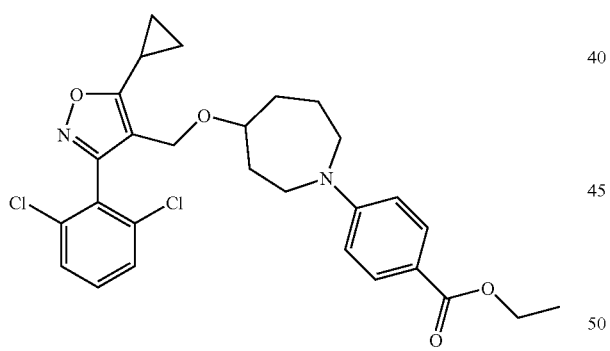

Anhydrous tetrahydrofuran (5 mL) is added at room temperature to a mixture of 4-(4-hydroxy-azepan-1-yl)-benzoic acid ethyl ester (364 mg, 1.38 mmol), 18-crown-6 (407 mg, 1.52 mmol) and tert-butyl alcohol, potassium derivative (178 mg, 1.52 mmol). The mixture is stirred for 5 minutes and then 4-bromomethyl-5-cyclopropyl-3-(2,6-dichloro-phenyl)-isoxazole (480 mg, 1.38 mmol) is added. After 1.5 h, the solvent is removed and water is added. The aqueous phase is extracted with ethyl acetate. The organic layers are combined, dried over anhydrous sodium sulfate, filtered, and the solvent is removed under reduced pressure. The residue is purified via flash chromatography (40 g silica) eluting with a gradient of ethyl acetate/hexane (0% to 30%) to provide the title compound as a colorless waxy solid (203 mg, 28%). ES/MS m/z 529.0 (M+1).

HPLC Chiral separation: Chiralpak AD (250×4.6 mm, 10 um): 6:4 Hex/IPA (0.2% DMEA) (flow rate: 12 mL/minute)
60 mg of isomer A is obtained
75 mg of isomer B is obtained Step 2

4-{4-[5-Cyclopropyl-3-(2,6-dichloro-phenyl)-isoxazol-4-ylmethoxy]-azepan-1-yl}-benzoic acid

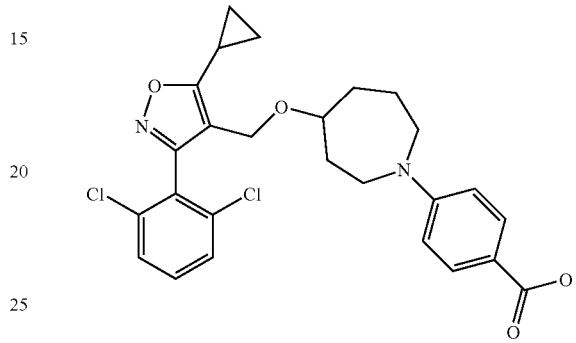

A solution 2M of lithium hydroxide (283 μL, 566 μmoles) is added to a solution of 4-{4-[5-cyclopropyl-3-(2,6-dichloro-phenyl)-isoxazol-4-ylmethoxy]-azepan-1-yl}-benzoic acid ethyl ester (isomer A, 60 mg, 113 μmoles) in 1,4-dioxane (2 mL) and the mixture is stirred at 90° C. overnight. The organic solvent is removed and HCl (1M) is added until the solution reaches pH 3-4. The solid is filtered and purified via flash chromatography (12 g silica) eluting with a gradient of dichloromethane:ethyl acetate from 10% to 20% to provide the title compound (50 mg, 88%) as a white solid. ES/MS m/z 501.0 (M+1).

Example 25

4-{4-[5-Cyclopropyl-3-(2,6-dichloro-phenyl)-isoxazol-4-ylmethoxy]-azepan-1-yl}-benzoic acid, isomer B

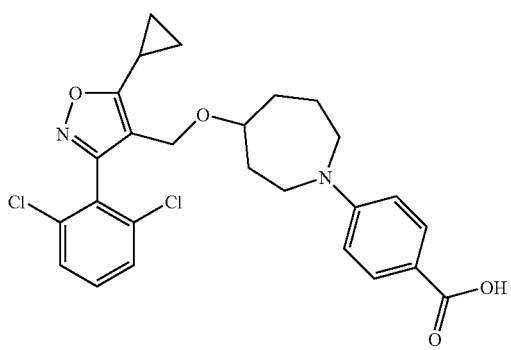

The title compound is prepared essentially as described in Step 2 of the preparation of 4-{4-[5-cyclopropyl-3-(2,6-dichloro-phenyl)-isoxazol-4-ylmethoxy]-azepan-1-yl}-benzoic acid, isomer A, using Isomer β isolated from Step 1 of 4-{4-[5-cyclopropyl-3-(2,6-dichloro-phenyl)-isoxazol-4-yl-methoxy]-azepan-1-yl}-benzoic acid. ES/MS m/z 501.0 (M+1)

Example 26

6-{4-[5-Cyclopropyl-3-(2,6-dichloro-phenyl)-isoxazol-4-ylmethoxy]-azepan-1-yl}-1-methyl-1H-indole-3-carboxylic acid

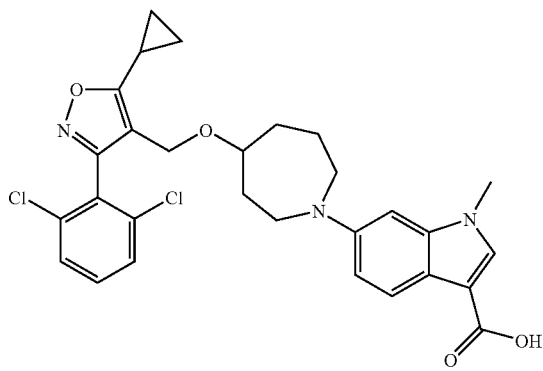

Step 1

6-{4-[5-Cyclopropyl-3-(2,6-dichloro-phenyl)-isoxazol-4-ylmethoxy]-azepan-1-yl}-1-methyl-1H-indole-3-carboxylic acid methyl ester

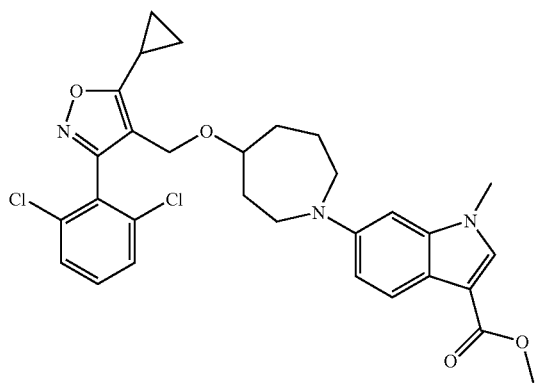

A mixture of 4-[5-cyclopropyl-3-(2,6-dichloro-phenyl)-isoxazol-4-ylmethoxy]-azepane hydrochloride (298 mg, 0.713 mmol), 6-bromo-1-methyl-1H-indole-3-carboxylic acid methyl ester (195 mg, 0.727 mmol), copper (I) iodide (40 mg, 0.208 mmol), DL-proline (60 mg, 0.516 mmol), and potassium carbonate (385 mg, 2.79 mmol) in dimethyl sulfoxide (3 mL) is heated to 100° C. for 18 h under nitrogen atmosphere. Saturated aqueous ammonium chloride is added and the mixture is extracted with ethyl acetate (3×). The combined ethyl acetate layers are washed with water (2×), brine (3×), dried (MgSO$_4$), and concentrated under reduced pressure. The residue is purified via flash chromatography (40 g silica) using a gradient of ethyl acetate in heptane (0 to 70%) to provided the title compound (47 mg, 12%). LC-ES/MS m/z 569.0 (M+1).

Step 2

6-{4-[5-Cyclopropyl-3-(2,6-dichloro-phenyl)-isoxazol-4-ylmethoxy]-azepan-1-yl}-1-methyl-1H-indole-3-carboxylic acid Following the procedure essentially as described in Example 1, Step 2 for 5-{4-[5-cyclopropyl-3-(2,6-dichloro-phenyl)-isoxazol-4-ylmethoxy]-piperidin-1-yl}-biphenyl-2-carboxylic acid, 6-{4-[5-cyclopropyl-3-(2,6-dichloro-phenyl)-isoxazol-4-ylmethoxy]-azepan-1-yl}-1-methyl-1H-indole-3-carboxylic acid methyl ester (47 mg, 0.083 mmol) provided 28 mg (61%) of the title compound. LC-ES/MS m/z 554.0 (M+1).

Example 27, listed in TABLE 3, is prepared essentially as described in the preparation of Example 26, 6-{4-[5-cyclopropyl-3-(2,6-dichloro-phenyl)-isoxazol-4-ylmethoxy]-azepan-1-yl}-1-methyl-1H-indole-3-carboxylic acid using the appropriate starting materials. For Examples 27A-27D in TABLE 3, follow the procedure essentially as described in Example 26, Step 1, except the reactions are completed in a sealed tube with heating to 110° C. For Examples 27C-27D, Step 2, substitute approximately 10 eq LiOH for NaOH sufficient to drive reaction to completion and add water in equal (vol/vol) amount to tetrahydrofuran and methanol. Stir the reaction mixture overnight at room temperature, neutralize to pH 6 with 1 N HCl, and concentrate to dryness. Dilute the material with water, extract with ethyl acetate, dry with Na$_2$SO$_4$ and concentrate to give the title compounds.

TABLE 3

| Ex No | Name | Data |
| --- | --- | --- |
| 27 | 6-{4-[5-Cyclopropyl-3-(2,6-dichloro-phenyl)-isoxazol-4-ylmethoxy]-azepan-1-yl}-benzo[b]thiophene-3-carboxylic acid | ES/MS (M + 1) 557 |
| 27A | 5-(4-((5-Cyclopropyl-3-(2,6-dichlorophenyl)isoxazol-4-yl)methoxy)piperidin-1-yl)-1-methyl-1H-indole-2-carboxylic acid | ES/MS (M + 1) 541 |
| 27B | 5-(4-((5-Cyclopropyl-3-(2,6-dichlorophenyl)isoxazol-4-yl)methoxy)piperidin-1-yl)benzo[b]thiophene-2-carboxylic acid | ES/MS (M + 1) 544 |
| 27C | 6-(4-((5-Cyclopropyl-3-(2,6-dichlorophenyl)isoxazol-4-yl)methoxy)piperidin-1-yl)benzo[d]isothiazole-3-carboxylic acid | ES/MS (M + 1) 544 |
| 27D | 6-(4-((5-Cyclopropyl-3-(2,6-dichlorophenyl)isoxazol-4-yl)methoxy)piperidin-1-yl)-1-methyl-1H-indazole-3-carboxylic acid | ES/MS (M + 1) 543 |

Example 28

Trans-4-{4-[5-Cyclopropyl-3-(2,6-dichloro-phenyl)-isoxazol-4-ylmethoxy]-cyclohexyl}-benzoic acid

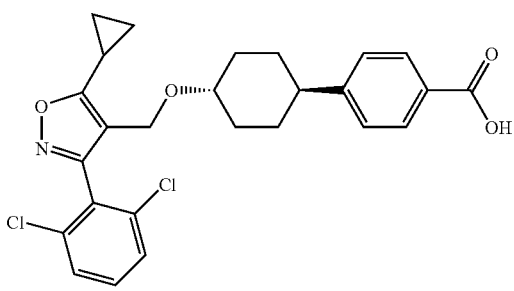

Step 1

Trans-4-{4-[5-Cyclopropyl-3-(2,6-dichloro-phenyl)-isoxazol-4-ylmethoxy]-cyclohexyl}-benzoic acid methyl ester

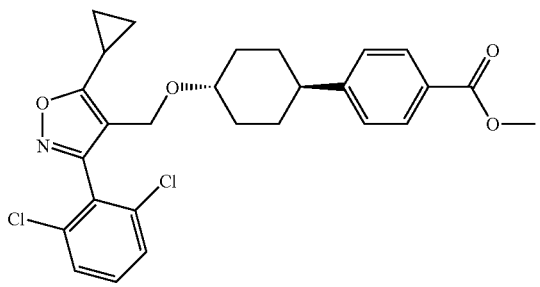

Trans-trifluoro-methanesulfonic acid 4-{4-[5-cyclopropyl-3-(2,6-dichloro-phenyl)-isoxazol-4-ylmethoxy]-cyclohexyl}-phenyl ester (1.03 mmol, 606.00 mg), methanol (10 mL), acetonitrile (15 mL), triethylamine (5.17 mmol, 720.00 μL), Pd(OAc)2 (52.56 μmoles; 11.80 mg), and 1,4-bis(diphenylphosphino)butane (61.90 μmoles; 26.40 mg) are combined and heated to 100° C. under CO gas (100 psi) for 4 h. The reaction mixture is cooled, filtered, and concentrated under reduced pressure. The crude mixture is purified by radial chromatography (4 mm plate) eluting with a gradient of hexanes/EtOAc (85:15 to 80:20) to give the title compound (422 mg, 82%) as a white solid. MS m/z 501.8 (M+1).

Step 2

Trans-4-{4-[5-Cyclopropyl-3-(2,6-dichloro-phenyl)-isoxazol-4-ylmethoxy]-cyclohexyl}-benzoic acid Trans-4-{4-[5-cyclopropyl-3-(2,6-dichloro-phenyl)-isoxazol-4-ylmethoxy]-cyclohexyl}-benzoic acid methyl ester (823.31 μmoles; 412.00 mg) is dissolved in tetrahydrofuran (8 mL) and methanol (10 mL). 2N aqueous NaOH (2.5 mL, 5 mmol) is added and the mixture is heated to 52° C. for 2 h. The reaction mixture is cooled and concentrated under reduced pressure. The residue is diluted with water (10 mL) and acidified with 5N HCl (1 mL). The solid is collected by filtration, washed with water, and dried in vacuo to give the title compound (313 mg, 78%) as a white solid. MS m/z 487.8 (M+1).

Example 29

4-{4-[5-Cyclopropyl-3-(2-trifluoromethoxy-phenyl)-isoxazol-4-ylmethoxy]-cyclohexyl}-benzoic acid

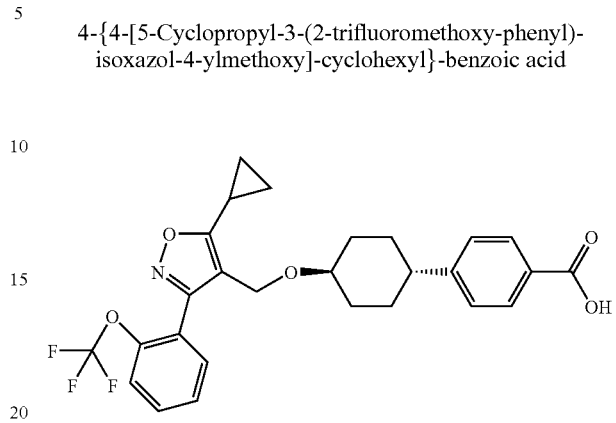

The title compound is prepared essentially according to the preparation of trans-4-{4-[5-Cyclopropyl-3-(2,6-dichloro-phenyl)-isoxazol-4-ylmethoxy]-cyclohexyl}-benzoic acid using the appropriate starting material. ES/MS m/z 502.0 (M+1)

Example 30

Cis-6-{4-[5-Cyclopropyl-3-(2-trifluoromethoxy-phenyl)-isoxazol-4-ylmethoxy]-cyclohexyl}-1-methyl-1H-indole-3-carboxylic acid

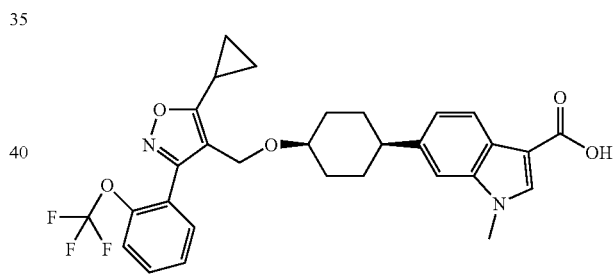

Step 1

Cis-6-{4-[5-Cyclopropyl-3-(2-trifluoromethoxy-phenyl)-isoxazol-4-ylmethoxy]-cyclohexyl}-1-methyl-1H-indole-3-carboxylic acid methyl ester

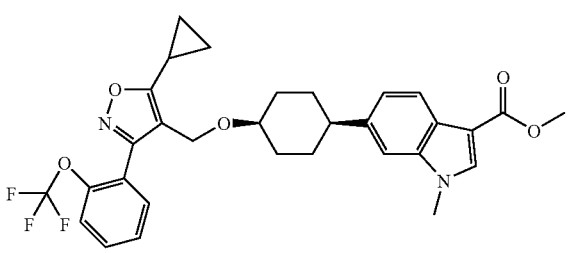

The title compound as a cis/trans mixture is prepared essentially as described in the preparation of trans-5-cyclopropyl-3-(2,6-dichloro-phenyl)-4-{4-[4-(4-methoxy-benzyloxy)-phenyl]-cyclohexyloxymethyl}-isoxazole starting from 1,6-(4-hydroxy-cyclohexyl)-1-methyl-1H-indole-3-carboxylic acid methyl ester (202 mg, 0.703 mmol) and 4-bromomethyl-5-cyclopropyl-3-(2-trifluoromethoxy-phenyl)-isoxazole (382 mg, 1.05 mmol). The isomers are separated by silica gel chromatography eluting with a gradient of 25-40% EtOAc/Hexanes to provide the cis isomer [62 mg, 15.5%; MS m/z 569.0 (M+1)] and trans isomer [52 mg, 13%; MS m/z 569.0 (M+1)].

Step 2

Cis-6-{4-[5-Cyclopropyl-3-(2-trifluoromethoxy-phenyl)-isoxazol-4-ylmethoxy]-cyclohexyl}-1-methyl-1H-indole-3-carboxylic acid The title compound (42 mg, 69%) is prepared essentially as described in Step 2 of trans-4-{4-[5-Cyclopropyl-3-(2,6-dichloro-phenyl)-isoxazol-4-ylmethoxy]-cyclohexyl}-benzoic acid using cis-6-(4-hydroxy-cyclohexyl)-1-methyl-1H-indole-3-carboxylic acid methyl ester (62 mg, 0.11 mmol) isolated in Step 1 above. MS m/z 555.2 (M+1)

Example 31

Trans-6-{4-[5-Cyclopropyl-3-(2-trifluoromethoxy-phenyl)-isoxazol-4-ylmethoxy]-cyclohexyl}-1-methyl-1H-indole-3-carboxylic acid

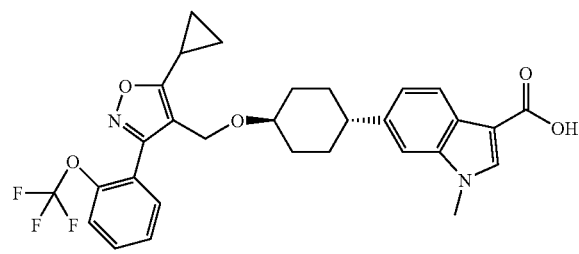

The title compound (32 mg, 63%) is prepared essentially as described in Step 2 of cis-6-{4-[5-cyclopropyl-3-(2-trifluoromethoxy-phenyl)-isoxazol-4-ylmethoxy]-cyclohexyl}-1-methyl-1H-indole-3-carboxylic acid using the trans isomer isolated in Step 1 of the preparation of cis-6-{4-[5-cyclopropyl-3-(2-trifluoromethoxy-phenyl)-isoxazol-4-ylmethoxy]-cyclohexyl}-1-methyl-1H-indole-3-carboxylic acid methyl ester. ES/MS m/z 555.2 (M+1).

Example 32

6-{4-[5-Cyclopropyl-3-(2,6-dichloro-phenyl)-isoxazol-4-ylmethoxy]-piperidin-1-yl}-1-methyl-1H-indole-3-carboxylic acid

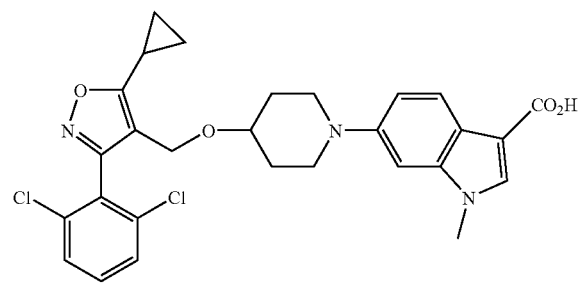

Step 1

2,6-Dichloro-benzaldehyde oxime

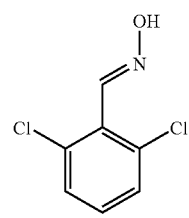

Sodium hydroxide 3N (3.14 L, 9.43 mol) is added dropwise to a stirred suspension of hydroxylamine hydrochloride (675.55 g, 9.43 mol) in 0.5 L of water at 0° C. To this mixture is added dropwise a suspension of 2,6-dichlorobenzaldehyde (1500 g, 8.57 mol) in 7.5 L of ethanol and the reaction is heated at 90° C. overnight. The mixture is cooled to room temperature and then, concentrated to dryness. The solid is triturated in a mixture of $H_2O$/EtOH, 10:1 (4.4 L), filtered and dried under high vacuum at 45° C. overnight. 1621.78 g of title compound (99% yield) is obtained as a white solid. MS (m/e): 190 (M+1)

Alternate procedure: Add triethylamine (23.1 g, 229 mmol) dropwise to a solution of 2,6-dichloro-benzaldehyde (20.0 g, 114 mmol) and hydroxylamine hydrochloride (10.3 g, 149 mmol) in dichloromethane (200 mL). Stir the reaction mixture for 8 h. Add water (200 mL). Separate the phases and extract the aqueous phase with dichloromethane (100 mL). Wash the combined organic phases with water (100 mL). Concentrate the combined organic phases to provide 28.8 g (94%) of the title compound.

Step 2

2,6-Dichloro-benzaldehyde chloro-oxime

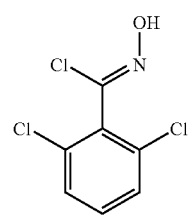

N-Chlorosuccinimide (1162 g, 8.53 mol) in DMF (4.5 L) is added dropwise over a solution of 2,6-dichloro-benzaldehyde oxime (1621.78 g, 8.53 mol) in DMF (5.3 L) heated at 40° C. (addition is complete in about 6 hours). The mixture is stirred for 1 h at that temperature. The reaction is cooled at room temperature, poured onto $H_2O$ (30 L) at 0° C., and extracted with MTBE (36 L) and the aqueous phase was discarded. The organic layer is washed with brine, dried over $Na_2SO_4$, filtered and evaporated to dryness (at 30° C.). The crude, as a solid-oil, is triturated in 1 L of hexane and the solid formed is filtered and dried under vacuum to obtain the desired compound (1440.9 g, 75% yield). MS (m/e): 224 (M+1).

Alternate Procedure: Add a solution of N-chlorosuccinimide (8.4 g, 62.8 mmol) in DMF (33 mL) to a 42° C. solution of 2,6-dichloro-benzaldehyde oxime (217 g, 1.14 mol) in DMF (700 mL). Stir for 30 minutes and then add a solution of N-chlorosuccinimide (159 g, 1.19 mol) in DMF (617 mL) while maintaining the temperature between 40° C. and 45° C. Stir for 1 hour. Cool to room temperature and stir for 2 h. The resulting solution of the title compound is used directly Step 3.

Step 3

5-Cyclopropyl-3-(2,6-dichloro-phenyl)-isoxazole-4-carboxylic acid methyl ester

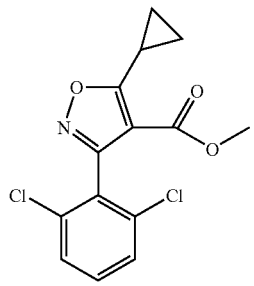

Triethylamine (1.82 L, 12.84 mol) is added to 3-cyclopropyl-3-oxo-propionic acid methyl ester (913 g, 6.42 mol) and the mixture is stirred at room temperature for 30 minutes. Then, the mixture is cooled to about 10° C. and a suspension of 2,6-dichloro-benzaldehyde chloro-oxime (1440.9 g, 6.42 mol) in EtOH (3.2 L) is added slowly (the internal temperature does not exceed 24° C.). After the addition, the reaction is stirred overnight at room temperature. The reaction is diluted with EtOAc (5.3 L) and washed with water (1.7 L). The layers are separated and the aqueous layer is extracted with EtOAc (3 L). The combined organics are washed with brine, dried over $Na_2SO_4$ (anhyd), filtered and concentrated to about 10% of its total volume. The precipitate formed is filtered, triturated with ether (2 L) and dried under vacuum to obtain title compound as a (1275.36 g, 64% yield) as a white solid. MS (m/e): 312 (M+1).

Alternate Procedure:

Add triethylamine (20.2 g, 0.2 mol) to 3-cyclopropyl-2-oxo-propionic acid methyl ester (18.5 g, 0.13 mol) and stir at room temperature for 30 minutes. Add the resulting solution to ¹/₁₀ of the previously prepared DMF solution of 2,5 dichlorobenzaldehyde-chloro-oxime (Alternate procedure Step 2) between 10° C. and 20° C. Warm to 25° C. to 30° C. and stir for 20 h. Add water (285 mL). Stir for 1 h and filter to afford 30.2 g (56%) of the title compound.

Step 4

[5-Cyclopropyl-3-(2,6-dichloro-phenyl)-isoxazol-4-yl]-methanol

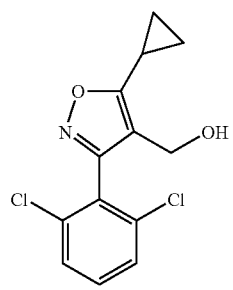

Diisobutylaluminium hydride 1M/toluene (4.62 L, 4.62 mol) is added dropwise to a stirred solution of 5-Cyclopropyl-3-(2,6-dichloro-phenyl)-isoxazole-4-carboxylic acid methyl ester (687.14 g, 2.20 mol) in THF (4.4 L) at 0° C. The reaction is stirred at room temperature for 2 hours. Methanol (150 mL) is added over the mixture at 0° C. and stirred for 10 min. Then, water (2.2 L) and EtOAc (4.3 L) is added. The precipitate formed is filtered through celite and all the solvents are removed in vacuum. The solid is triturated in 1 L of hexane and dried under vacuum filtration to obtain title compound (534.7 g, 85% yield) as a white solid. MS (m/e): 312 (M+1). Alternate procedure: Cool a solution of 5-cyclopropyl-3-(2, 6-dichloro-phenyl)-isoxazole-4-carboxylic acid methyl ester (62.4 g, 200 mmol) in dichloromethane (400 mL) to 0° C. Add diisobutylaluminum hydride (440 mL, 1.0 M, 440 mmol) while maintaining the temperature between –5° C. and 0° C. Stir the resulting mixture for 30 min. Warm to 15° C. to 25° C. and stir for 3 h. Add the reaction solution to 2.0 M HCl (800 mL) at ~8° C. to 10° C. Stir for 30 minutes Separate the phases and extract the aqueous phase with dichloromethane (200 mL). Wash the combined organic phases with water (3×100 mL). Concentrate the organic phase to 180 mL total volume. Add heptane (350 mL). Filter the resulting solid to afford 51.5 g (90%) of the title compound.

Step 5

4-Bromomethyl-5-cyclopropyl-3-(2,6-dichloro-phenyl)-isoxazole

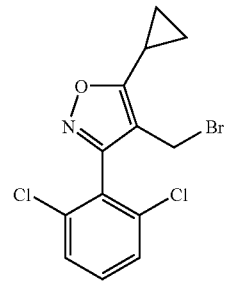

To a solution of 30 g (105.58 mmol) of [5-cyclopropyl-3-(2,6-dichloro-phenyl)-isoxazol-4-yl]-methanol in 210 mL of dichloromethane is added 41.96 g (158 mmol) of triphenylphosphine. The resulting mixture is cooled in an ice bath (about 0-10° C.) and added in portions to carbon tetrabromide (53 g, 158.37 mmol). The reaction is stirred at room temperature for 2 h. The solvent is evaporated to obtain an orange oil which is purified on silica gel column chromatography using Hexanes to hex/EtOAc 8:2 as eluent, to obtain 33 g of the title compound as a white solid (90%). MS (m/e): 346 (M+1).

Alternate procedure: Cool a solution of (5-cyclopropyl-3-(2, 6-dichloro-phenyl)-isoxazol-4-yl)-methanol (100 g, 0.35 mol) in dichloromethane (1200 mL) to –10° C. Add phosphorous tribromide (105 g, 0.39 mol) dropwise while maintaining the internal temperature between –5° C. and 0° C. Stir at –5° C. to 0° C. for 30 min. Allow to warm to between 20° C. and 25° C. and stir at 20° C. to 35° C. for 2 h. Cool the reaction mixture to 0° C. to 5° C. Add an aqueous solution of sodium bicarbonate (775 mL) dropwise. Separate the phases. Extract the aqueous phase with dichloromethane (2×350 mL). Wash the combined organic phases with water (3×500 mL). Concentrate the organic phase to afford 115 g (94%) of the title compound as a solid.

Step 6

4-[5-Cyclopropyl-3-(2,6-dichloro-phenyl)-isoxazol-4-ylmethoxy]-piperidine-1-carboxylic acid tert-butyl ester

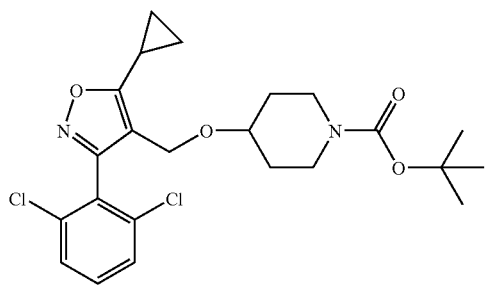

To a solution of 13.05 g (64.83 mmol) of 4-hydroxy-piperidine-1-carboxylic acid tert-butyl ester in THF (120 mL) is added at 0° C. (ice bath) 18-crown-6 (19.6 g, 73.48 mmol) and potassium tertiary butoxide (8.68 g, 73.48 mmol). The resulting mixture is stirred for 20 min at room temperature, and added dropwise to a solution of 4-bromomethyl-5-cyclopropyl-3-(2,6-dichloro-phenyl)-isoxazole (15 g, 43.22 mmol) in 75 mL of THF. The resulting mixture was stirred at room temperature for 14 h. To the reaction mixture is added water (500 mL), and it is extracted with EtOAc (3×200 mL). The organics are washed with brine (2×250 mL), dried (Na$_2$SO$_4$), filtered and concentrated to afford a crude which is purified by flash chromatography eluting with Hexanes/EtOAc 8:2, to obtain the title compound as a pale yellow oil (16 g (79%)). MS (m/e): 467 (M+1)

Step 7

4-[5-Cyclopropyl-3-(2,6-dichloro-phenyl)-isoxazol-4-ylmethoxy]-piperidine

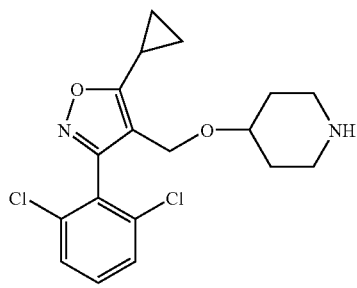

In a cooled (ice bath) 500 mL flask under nitrogen, is added a solution of 4-[5-cyclopropyl-3-(2,6-dichloro-phenyl)-isoxazol-4-ylmethoxy]-piperidine-1-carboxylic acid tert-butyl ester (16 g, 34.3 mmol) in dichloromethane (80 mL). This is followed by dropwise addition of trifluoroacetic acid (80 mL) (added over 30 minutes). The reaction is stirred at room temperature for 90 min. The solvent is removed under vacuum, EtOAc is added (400 mL), and the mixture is washed with 2 N NaOH (2×250 mL) and brine. The organic layer is dried over MgSO$_4$, filtered and evaporated to obtain the title compound as a brown oil (11.78 g, 93%). MS (m/e): 367 (M+1)

Alternate Procedure: Step 6 and 7 combined to form 5-Cyclopropyl-3-(2,6-dichlorophenyl)-4-((piperidin-4-yloxy)methyl)isoxazole hydrochloride

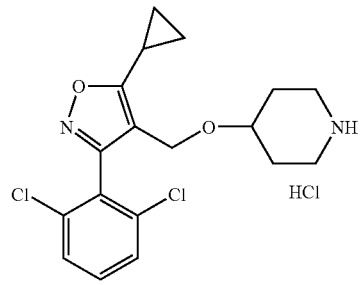

Cool a solution of 4-hydroxy-piperidine-1-carboxylic acid tert-butyl ester (352 g, 1.75 mol) and 18-crown-6 (463 g, 1.75 mol) in THF to between 0° C. and 5° C. Add potassium tert-butoxide (268 g, 2.39 mol) while maintaining the temperature between 0° C. and 10° C. Cool the resulting mixture to −10° C. to −5° C. Add a 40 wt % solution of 4-bromomethyl-5-cyclopropyl-3-(2,6-dichloro-phenyl)-isoxazole in THF (1.38 kg, 1.59 mol) while maintaining the temperature between −5° C. and 0° C. Allow the mixture to warm to 15° C. to 25° C. and stir for 2 h. Cool to 0° C. to 5° C., and add water dropwise while maintaining the temperature between 0° C. and 10° C. Add ethyl acetate (3.5 L) and brine (5.5 L). Separate the phases and extract the aqueous phase with ethyl acetate (2×2.5 L). Wash the combined organic phases with brine (3×5.5 L). Concentrate the organic phase under vacuum to approximately 1.5 L total volume to afford a solution of crude 4-[5-cyclopropyl-3-(2,6-dichloro-phenyl)-isoxazol-4-ylmethoxy]-piperidine-1-carboxylic acid tert-butyl ester. Add additional ethyl acetate (3.0 L). Cool the solution to 0° C. to 5° C. Add HCl (gaseous) (319 g, 8.75 mol) while maintaining the temperature between 0° C. and 5° C. Allow to warm to 15° C. to 25° C. and stir for 4 h. Concentrate the mixture under vacuum to approximately 1.2 L total volume. Filter the resulting solid and wash with cold ethyl acetate (2×0.6 L). Dry to afford 506 g (79%) of the title compound as an off-white solid. mp 200-202° C. (by differential scanning calorimetry).

Step 8

6-bromo-indole-3-carboxylic acid

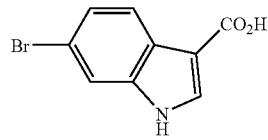

Bromine (49.58 g, 3100 mmol) is added slowly to a white suspension of Indole-3-carboxylic acid (50 g, 310 mmol) in 500 mL of acetic acid at room temperature, and the mixture is stirred at room temperature overnight. The solid formed is filtered and dried under vacuum for 3 hours to afford 45 g of the title compound as a grey solid (60%). MS (m/e): 240 (M+1)

Step 9

6-Bromo-1H-indole-3-carboxylic acid methyl ester

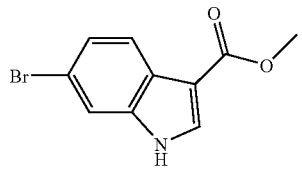

Acetyl chloride (29.43 g, 374 mmol) is added slowly at room temperature to a solution of 6-bromo-indole-3-carboxylic acid (45 g, 187.46 mmol) in 500 mL of methanol and the resulting solution is stirred at 65° C. overnight. The reaction is cooled to room temperature. A white precipitates appears when cooling. After stirring 2 h at room temperature, the solid is filtered off and dried under vacuum. 34.4 g (72%) of the title compound is obtained as a light brown solid. MS (m/e): 254 (M+1)

Step 10

6-Bromo-1-methyl-1H-indole-3-carboxylic acid methyl ester

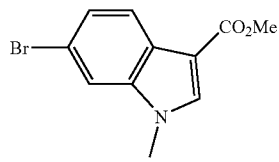

To a mixture of 25 g (98.39 mmol) of 6-bromo-1H-indole-3-carboxylic acid methyl ester and 27.20 g (196 mmol) of potassium carbonate in 300 mL of acetonitrile is added at room temperature Methyl Iodide (20.95 g, 147.6 mmol). The reaction mixture is stirred at room temperature for 3 days. The solvent is evaporated, 500 ml of water is added, and the organic layer is extracted with (3×300 ml) ethyl acetate. The organics are combined, dried over magnesium sulfate and evaporated. The crude is purified by silica gel chromatography eluting with hex/EtOAc 8:2. The title compound (23.3 g (88%)) is obtained as a brown solid. MS (m/e): 268 (M+1).

Alternate procedure: Add dimethyl carbonate (1.3 L, 12.4 mol) to a mixture of 6-bromo-1H-indole-3-carboxylic acid methyl ester (1.3 kg, 5.1 mol) and potassium carbonate (1.41 kg, 10.2 mol) in DMF (6.0 L) at room temperature. Heat the mixture to 130° C. and stir overnight. Cool the reaction mixture to ~3° C. and add ice-cold water (6 L). Filter the resulting solid, wash with methanol (2 L) and dry in a vacuum oven to afford 1.1 kg (82%) of the title compound.

Step 11

6-{4-[5-Cyclopropyl-3-(2,6-dichloro-phenyl)-isoxazol-4-ylmethoxy]-piperidin-1-yl}-1-methyl-1H-indole-3-carboxylic acid methyl ester

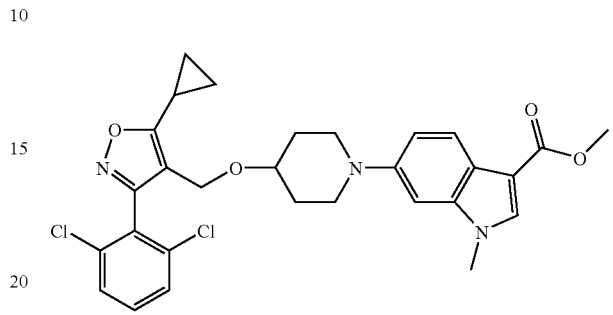

A 250 mL sealed round bottom flask under nitrogen is charged with 4-[5-cyclopropyl-3-(2,6-dichloro-phenyl)-isoxazol-4-ylmethoxy]-piperidine (15 g, 40.84 mmol), 6-bromo-1-methyl-1H-indole-3-carboxylic acid methyl ester (15.33 g, 57.18 mmol); potassium carbonate (11.29 g, 81.68 mmol), copper(I) iodide (3.11 g, 16.34 mmol), and proline (1.88 g, 16.34 mmol) in 80 mL of dimethyl sulfoxide. The reaction mixture is heated at 120° C. for 16 h. Then, it is cooled down to room temperature, quenched with water (200 mL) and extracted with EtOAc (3×150 mL). The organics are washed with water and brine, dried over MgSO4, filtered and evaporated. The crude is purified by flash silica gel chromatography using hex/EtOAc 8:2 to 1:1 as eluent system, to obtain 9.8 g of the title compound as a white solid (43%). MS (m/e): 554 (M+1)

Step 12

6-{4-[5-Cyclopropyl-3-(2,6-dichloro-phenyl)-isoxazol-4-ylmethoxy]-piperidin-1-yl}-1-methyl-1H-indole-3-carboxylic acid

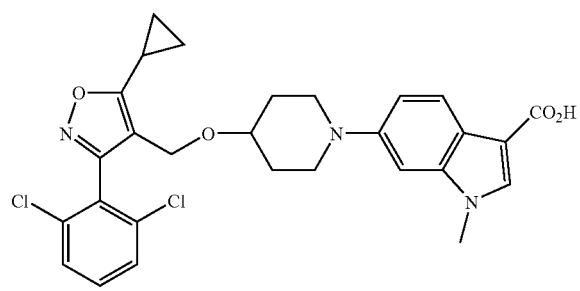

In a 500 mL round bottom flask under nitrogen, containing a solution of 9 g (16.23 mmol) of 6-{4-[5-cyclopropyl-3-(2,6-dichloro-phenyl)-isoxazol-4-ylmethoxy]-piperidin-1-yl}-1-methyl-1H-indole-3-carboxylic acid methyl ester in 80 mL of methanol, 80 mL of THF and 30 mL dioxane, is added 2N KOH (40 mL, 81.16 mmol). The reaction mixture is stirred at 70° C. overnight. The reaction mixture is then cooled to room temperature, and the solvent removed under vacuum. The residue is diluted with 100 mL of water, and washed with MTBE. The aqueous layer is acidified (pH 5) by addition of 2N HCl, then, it is extracted with $CH_2Cl_2$ (3×150 mL). The organics are dried over $MgSO_4$, filtered, and evaporated to yield a light green solid that is recrystallized from MeOH/$CH_3CN$ (6.05 g (70%)). MS (m/e): 540 (M+1).

Alternate Procedures

Step 10A tert-Butyl 6-bromo-1-methyl-1H-indole-3-carboxylate

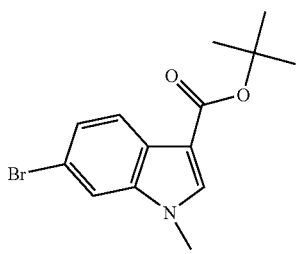

Dissolve 6-bromo-1-methyl-1H-indole-3-carboxylic acid methyl ester (17.16 Kg, 63.98 mol) in toluene (134.5 Kg) under nitrogen atmosphere. Stir at least 15 minutes. Add magnesium sulfate to dry and charcoal to de-colorize the solution and stir at least 30 minutes. Filter the mixture. Dissolve sodium tert-butoxide (21.5 Kg, 223.70 mol) in toluene (43.7 kg) under a nitrogen atmosphere. Add the starting material solution mixture to the sodium tert-butoxide solution and heat the reaction mixture slowly over approximately 2-3 hours to a temperature of 105-108° C. and maintain temperature for 30-60 minutes. Follow by TLC until no starting material is observed. Cool the reaction to room temperature and quench the mixture into water (177.2 Kg) cooled to 0-10° C. Stir the reaction mixture for at least 30 minutes and separate the aqueous layer and emulsion. Wash the organic mixture with brine (2×47.7 Kg) maintaining the emulsion with the aqueous brine wash. Extract the combined aqueous layer with toluene (2×29.9 Kg). Filter organic layer and any emulsion through diatomaceous earth. Wash the filter cake with toluene (6.1 Kg). Wash the combined organic layers with brine (2×47.7 Kg). Add magnesium sulfate (7 Kg) and charcoal (850 g) and stir for 30 minutes. Filter the mixture and concentrate the filtrate at 50-55° C. to the lowest stirrable volume. Discontinue heating and add heptane (47.3 Kg) to the mixture. Cool the suspension to 0-5° C. for at least 2 hours and collect the solids by filtration. Rinse the solids with heptane cooled to 0-5° C. Dry solids at 30-35° C. for 12-72 hours under vacuum to give 13.110 Kg (66%) of the title compound.

Step 10B tert-Butyl 6-iodo-1-methyl-1H-indole-3-carboxylate

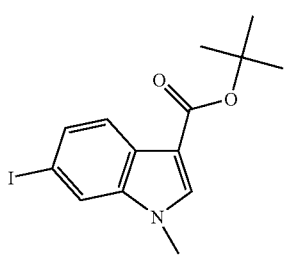

Add tert-butyl 6-bromo-1-methyl-1H-indole-3-carboxylate (25.87 Kg, 83.4 mol) to 1,4-dioxane (187.3 Kg) under a nitrogen atmosphere. Add sodium iodide (25 Kg, 166.79 mol), copper iodide (3.2 Kg, 16.80 mol), N,N'-dimethylethylenediamine (2.9 Kg 32.90 mol) to the reaction mixture and heat to reflux (~102°) for 36-48 hours. Cool the mixture to room temperature, filter through 2 in-line filters in series, (1 μm and 0.45 μm respectively) into an appropriate sized dry reactor, and rinse with dioxane (2×5.4 Kg). Add sodium iodide (12.5 Kg, 83.39 mol), copper iodide (1.6 Kg, 8.4 mol), and N,N'-dimethylethylenediamine (1.5 Kg, 17.02 mol) and heat the mixture to reflux for 36-48 hours. Cool to 15-30° C., add water (417 Kg) to the reaction mixture, and stir at least 1 hour at room temperature. Collect the solids by filtration and wash with water. Add the solids to ethyl acetate (188.1 Kg) and stir for 30 minutes. Filter off undissolved solids through a plate filter with a polypropylene filter pad and filter the filtrate through 2 in-line filters in series (1 μm and 0.45 μm respectively). Wash the solids with ethyl acetate (2×11.3 Kg) and filter the filtrate through 2 in-line filters in series (1 μm and 0.45 μm respectively) into the original filtrate. Wash the organic layer with aqueous ammonia/water solution (2×81.7 Kg, stir for at least 30 minutes, and separate. Repeat if aqueous ammonia layer is not colorless. Wash with brine (57.8 Kg), stir for at least 15 minutes, and separate. Add magnesium sulfate (6 Kg) and charcoal (500 g) and stir for 20 minutes. Filter the mixture through 2 in-line filters in series (1 μm and 0.45 μm respectively) into an appropriate-sized, dry reactor and rinse reactor with ethyl acetate (2×11.7 Kg) with subsequent filtering through the 2 in-line filters. Concentrate the combined filtrates at a temperature of 35-40° C. to lowest stirrable volume. Add methanol (26.4 Kg) and concentrate to lowest stirrable volume. Add methanol (66 Kg) and cool to 0-10° C. and collect the solid by filtration. Add the solid to methanol (197.9 Kg) and heat to reflux until a clear solution is obtained. Cool to 0-5° C. over 2-3 hours and stir for at least 2 hours. Collect the solids by filtration, rinse reactor with methanol (2×13.2 Kg), cool methanol to 0-5° C. and use to rinse the filtered solids. Dry solids at 35-40° C. for 12-72 hours under vacuum to give 16.412 Kg (55%) of the title compound.

Step 11A tert-Butyl 6-(4-{[3-(2,6-dichlorophenyl)-5-cyclopropylisoxazol-4-yl]methoxy}piperidyl)-1-methylindole-3-carboxylate

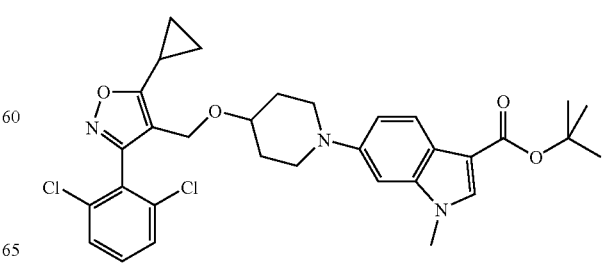

Add 5-cyclopropyl-3-(2,6-dichlorophenyl)-4-[(piperidin-4-yloxy)methyl] isoxazole hydrochloride (15.609 Kg, 38.66 mol) to toluene (229.5 Kg) under a nitrogen atmosphere. Add tert-butyl 6-iodo-1-methylindole-3-carboxylate (18.0 Kg, 50.39 mol) and sodium tert-butoxide (9.3 Kg, 96.76 mol) and heat to 55-60° C. for at least 1 hour. Add 2-dicyclohexylphosphino-2'-(N,N-dimethylamino)biphenyl (304 g, 0.77 mol) and tris(dibenzylidene acetone)dipalladium, $Pd_2\,dba_3$, (354 g, 0.39 mol) and heat the mixture to 55-60° C. Do not allow temperature to go above 65° C. Follow by TLC until no starting material (5-cyclopropyl-3-(2,6-dichlorophenyl)-4-[(piperidin-4-yloxy)methyl] isoxazole hydrochloride is observed). Discontinue heating, add water (31.2 Kg) and cool mixture to 15-30° C. Separate the layers and filter the aqueous layer and emulsion through diatomaceous earth. Wash the filter cake with toluene (2×5.4 Kg) and combine the washes with the aqueous filtrate. Stir for 10 minutes and separate the layers. Combine the organic layer with the original organic layer. Re-extract the aqueous layer with toluene (13.5 Kg). Combine organics and wash with brine (2×30.3 Kg) and separate the layers. Add magnesium sulfate (5.0 Kg) and charcoal (800 g) to the organic layer and stir for 20 minutes. Filter the mixture. Rinse filter cake with toluene (5.4 Kg) and combine the organics. Add silica gel (7.0 Kg), and stir for 20-30 minutes. Add thiol derivatized silica gel (6.2 Kg) and stir for at least 15 hours. Filter solids. Wash the filter cake with toluene (2×10.8 Kg) and combine washes with filtrate. Concentrate washes at 50-55° C. to lowest stirrable volume. Cool to 15-30° C. and add heptane (22.3 Kg) in a thin stream. Stir for 30-60 minutes. Add heptane (21.3 Kg) in a thin stream and stir for at least 1 hour. Cool to 0-5° C. and stir for 1-2 hours. Collect solids by filtration. Wash the filter cake with heptane (2×4.2 kg) cooled to 0-5° C. Dry the solids at 50-55° C. for 12-72 hours under vacuum. Add the dry solids to toluene (45.7 Kg) and heat until a clear solution is obtained. Cool to 15-30° C. and add heptane (36.2 Kg). Stir for 30-90 minutes at room temperature. Add heptane (18.1 Kg) and stir 30-90 minutes. Repeat the addition of heptane (18.1 Kg) and stir for 1-2 hours. Cool the suspension to 0-5° C. and stir for 30-90 minutes. Collect the solids by filtration. Wash the filter cake with heptane (2×9.0 kg) cooled to 0-5° C. Dry the solids at 50-55° C. for 12-72 hours under vacuum. Add the dry solids to methanol (118.6 Kg) and heat the suspension to reflux for 30-60 minutes. Cool the suspension to 0-5° C. and stir for 30-60 minutes. Collect the solids by filtration. Wash the filter cake with methanol (16.9 kg) cooled to 0-5° C. Dry the solids at 45-50° C. for 12-72 hours under vacuum to give 19.102 Kg (89%) of the title compound.

Step 12A

6-{4-[5-Cyclopropyl-3-(2,6-dichloro-phenyl)-isoxazol-4-ylmethoxy]-piperidin-1-yl}-1-methyl-1H-indole-3-carboxylic acid

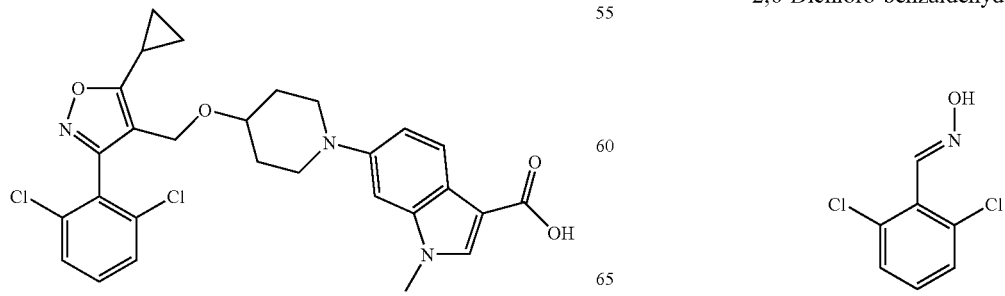

To formic acid (116.5 Kg), add tert-butyl 6-(4-{[3-(2,6-dichlorophenyl)-5-cyclopropylisoxazol-4-yl]methoxy}piperidyl)-1-methylindole-3-carboxylate (19.102 Kg, 34.45 mol) under a nitrogen atmosphere. Stir the mixture at 20-30° C. for 24-72 hours. Follow by HPLC until no starting material is observed. Add water (286.5 Kg) and stir for at least 1 hour. Add water (133.7 Kg) and stir for at least 30 minutes, repeat with a further addition of water (133.7 Kg) with stirring for at least 30 minutes. Collect the solids by filtration and rinse the filter cake with water (3×30 Kg). Add the wet solids to methanol (75.5 Kg) and stir the suspension for at least 12 hours. Cool the suspension to 0-5° C. and stir for at least 1 hour. Collect the solids by filtration. Wash the solids with a solution of methanol (9.1 Kg) and water (1.1 Kg) cooled to 0-5° C. and repeat. Dry solids at 50-55° C. for 12-72 hours under vacuum. Add the solids to formic acid (28.5 Kg) and water (2.3 Kg) and stir for 10-20 minutes. Filter the mixture. Add water (49.7 Kg) and stir for 30-60 minutes. Add water (2×36.6 Kg) and stir for at least 30 minutes. Collect solids by filtration and rinse with water (3×15.9 Kg). Add collected solids to methanol (58.2 Kg). Stir for at least 12 hours, cool to 0-5° C. and stir for at least 1 hour. Collect solids by filtration. Wash solids with a solution of methanol (8.1 Kg) and water (1.1 Kg) cooled to 0-5° C., repeat once. Add the collected solids to a solution of methanol (115.6 Kg) and water (14.6 Kg). Heat the suspension to reflux for 2-3 hours, cool to 0-5° C. and stir 1 hour. Collect the solids by filtration. Wash the solids with a solution of methanol (17.3 Kg) and water (2.2 Kg) cooled to 0-5° C., repeat once. Dry collected solids at 60-65° C. for 12-72 hours under vacuum to give 13.584 Kg (73%) of the title compound.

Example 33

4-{4-[5-Cyclopropyl-3-(2,6-dichloro-phenyl)-isoxazol-4-ylmethoxy]-azepan-1-yl}-benzoic acid

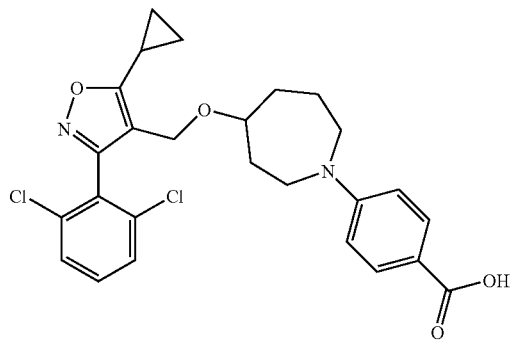

Step 1

2,6-Dichloro-benzaldehyde oxime

Sodium hydroxide 3N (3.14 L, 9.43 mol) is added dropwise to a stirred suspension of hydroxylamine hydrochloride (675.55 g, 9.43 mol) in 0.5 L of water at 0° C. To this mixture is added dropwise a suspension of 2,6-dichlorobenzaldehyde (1500 g, 8.57 mol) in 7.5 L of ethanol and the reaction is heated at 90° C. overnight. The mixture is cooled to room temperature and then, concentrated to dryness. The solid is triturated in a mixture of $H_2O$/EtOH, 10:1 (4.4 L), filtered and dried under high vacuum at 45° C. overnight. 1621.78 g of title compound (99%) is obtained as a white solid. MS (m/e): 190 (M+1)

Step 2

2,6-Dichloro-benzaldehyde chloro-oxime

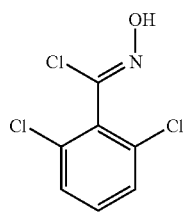

N-Chlorosuccinimide (1162 g, 8.53 mol) in DMF (4.5 L) is added dropwise over a solution of 2,6-dichloro-benzaldehyde oxime (1621.78 g, 8.53 mol) in DMF (5.3 L) heated at 40° C. (addition is complete in about 6 hours). The mixture is stirred for 1 h at that temperature. The reaction is cooled at room temperature, poured onto $H_2O$ (30 L) at 0° C., and extracted with MTBE (36 L). The organic layer is washed with brine, dried over $Na_2SO_4$, filtered and evaporated to dryness (at 30° C.). The crude, as a solid-oil, is triturated in 1 L of hexane and the solid formed is filtered and dried under vacuum to obtain the desired compound (1440.9 g, 75% yield). MS (m/e): 224 (M+1)

Step 3

5-Cyclopropyl-3-(2,6-dichloro-phenyl)-isoxazole-4-carboxylic acid methyl ester

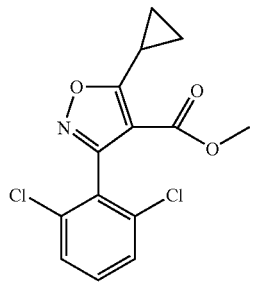

Triethylamine (1.82 L, 12.84 mol) is added to 3-cyclopropyl-3-oxo-propionic acid methyl ester (913 g, 6.42 mol) and the mixture is stirred at room temperature for 30 minutes. Then, the mixture is cooled to about 10° C. and a suspension of 2,6-dichloro-benzaldehyde chloro-oxime (1440.9 g, 6.42 mol) in EtOH (3.2 L) is added slowly (the internal temperature does not exceed 24° C.). After the addition, the reaction is stirred overnight at room temperature. The reaction is diluted with EtOAc (5.3 L) and washed with water (1.7 L).

The layers are separated and the aqueous layer is extracted with EtOAc (3 L). The combined organics are washed with brine, dried over $Na_2SO_4$ (anhyd), filtered and concentrated to about 10% of its total volume. The precipitate formed is filtered, triturated with ether (2 L) and dried under vacuum to obtain title compound (1275.36 g, 64% yield) as a white solid. MS (m/e): 312 (M+1).

Step 4

[5-Cyclopropyl-3-(2,6-dichloro-phenyl)-isoxazol-4-yl]-methanol

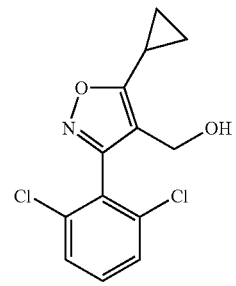

Diisobutylaluminium hydride 1M/toluene (4.62 L, 4.62 mol) is added dropwise to a stirred solution of 5-Cyclopropyl-3-(2,6-dichloro-phenyl)-isoxazole-4-carboxylic acid methyl ester (687.14 g, 2.20 mol) in THF (4.4 L) at 0° C. The reaction is stirred at room temperature for 2 hours. Methanol (150 mL) is added over the mixture at 0° C. and stirred for 10 min. Then, water (2.2 L) and EtOAc (4.3 L) is added. The precipitate formed is filtered through celite and all the solvents are removed in vacuum. The solid is triturated in 1 L of hexane and dried under vacuum filtration to obtain title compound (534.7 g, 85% yield) as a white solid. MS (m/e): 312 (M+1)

Step 5

4-Bromomethyl-5-cyclopropyl-3-(2,6-dichloro-phenyl)-isoxazole

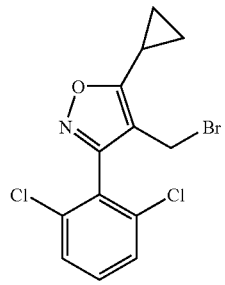

To a solution of 30 g (105.58 mmol) of [5-Cyclopropyl-3-(2,6-dichloro-phenyl)-isoxazol-4-yl]-methanol in 210 mL of dichloromethane is added 41.96 g (158 mmol) of triphenylphosphine. The resulting mixture is cooled in an ice bath (about 0-10° C.) and added in portions to carbon tetrabromide (53 g, 158.37 mmol). The reaction is stirred at room temperature for 2 h. The Solvent is evaporated to obtain an orange oil which is purified on silica gel column chromatography using Hexanes to hex/EtOAc 8:2 as eluent, to obtain 33 g of the title compound as a white solid (90%). MS (m/e): 346 (M+1).

Step 6

4-Oxo-azepane-1-carboxylic acid tert-butyl ester

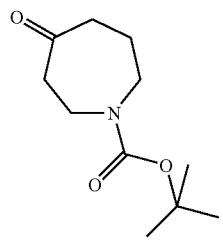

To a solution of hexahydro-4H-azepin-4-one monohydrochloride (4.87 g, 32.55 mmol), in 40 mL of 1,4-dioxane is added 8.06 g (35.80 mmol) of di-t-butyldicarbonate. The resulting suspension is stirred at room temperature for 10 minutes followed by addition of slurry of sodium carbonate 2.07 g (19.53 mmol) in water. The resulting mixture is stirred at 80° C. for 2 hours. The reaction mixture is cooled to room temperature and the solvent removed under reduced pressure. The residue is diluted and extracted with EtOAc (100 mL×3). The combined organic layers are dried (Na$_2$SO$_4$), filtered and concentrated to obtained an orange oil which is purified on silica gel column chromatography (eluting with Hexanes/EtOAc 7:3) to afford 6.51 g of the title compound as a colorless oil (93%). MS (m/e): 214 (M+1).

Step 7

4-Hydroxy-azepane-1-carboxylic acid tert-butyl ester

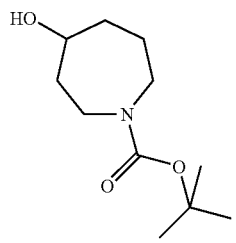

To a solution of 1 g (4.69 mmol) of 4-oxo-azepane-1-carboxylic acid tert-butyl ester), in 2 mL of Methanol and 8 mL of THF, is added at 0° C. (ice bath) sodium tetrahydroborate (0.18 g, 4.69 mmol). The resulting mixture is stirred at 0° C. for 1 h. To the reaction mixture is added at 0° C. (ice bath), a solution of HCl (1N) (2 mL), then solvent is removed and the resulting slurry is diluted with water and extracted with EtOAc (250 mL). The organic layers are combined, dried (Na$_2$SO$_4$), filtered and concentrated to afford the title compound as a colorless oil (0.95 g, 94%). MS (m/e): 216 (M+1).

Step 8

4-[5-Cyclopropyl-3-(2,6-dichloro-phenyl)-isoxazol-4-ylmethoxy]-azepane-1-carboxylic acid tert-butyl ester

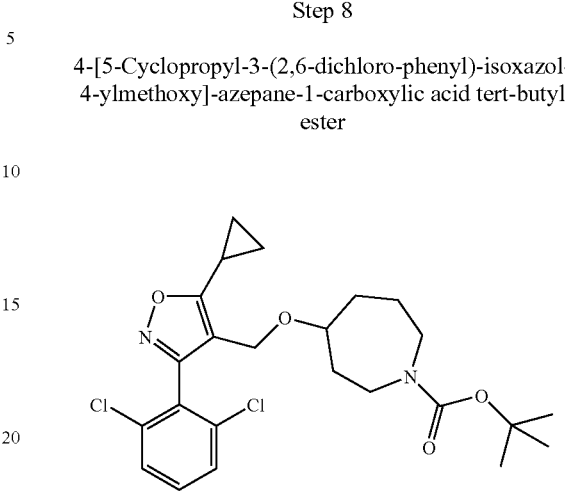

To a solution of 36.11 g (167.7 mmol) of 4-hydroxy-azepane-1-carboxylic acid tert-butyl ester in 300 mL of tetrahydrofuran at 0° C. (ice bath), 18-crown-6 (63.43 g, 237.58 mmol) and potassium tert-butoxide (28.06 g, 250.04 mmol) are added. The resulting mixture is stirred for 20 min at room temperature under nitrogen, followed by addition of a solution of 48.5 g (139.75 mmol) of 4-Bromomethyl-5-cyclopropyl-3-(2,6-dichloro-phenyl)-isoxazole in 100 mL tetrahydrofuran over a 1 hour period. The resulting mixture is stirred at room temperature under nitrogen atmosphere for 12 hours. Water (200 mL) is added to the reaction mixture and the solvent is removed under reduced pressure. The resulting brown oil is diluted with EtOAc (2×250 mL), and washed with brine (2×150 mL). The organic layer is dried (Na$_2$SO$_4$), filtered and concentrated to afford a crude which is purified on silica gel column chromatography (Eluting with Hexanes/EtOAc 8:2) to obtain 56 g of the title compound as a white/yellow oil. (83%). MS (m/e): 481 (M+1).

Step 9

4-[5-Cyclopropyl-3-(2,6-dichloro-phenyl)-isoxazol-4-ylmethoxy]-azepane

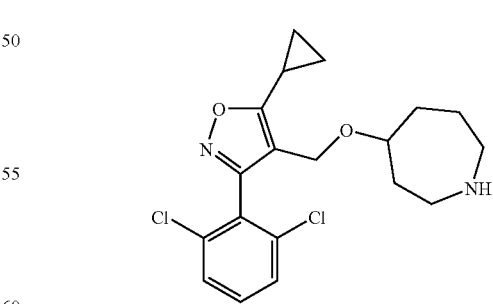

A solution of 56 g (116.32 mmol) of 4-[5-cyclopropyl-3-(2,6-dichloro-phenyl)-isoxazol-4-ylmethoxy]-azepane-1-carboxylic acid tert-butyl ester in 150 mL of dichloromethane at 0° C. (ice bath) is treated with trifluoroacetic acid (150 mL, 1.98 mol). The mixture is stirred at room temperature under nitrogen for 2 hours. The reaction mixture is concentrated.

The crude product is dissolved with EtOAc (300 mL), washed with a solution 2N—NaOH (2×100 mL) and washed with brine (1×100 mL). The organics are dried (Na₂SO₄), filtered and concentrated to afford 38 g of the desired compound as a yellow oil (86%). MS (m/e): 381 (M+1).

Step 10

4-{4-[5-Cyclopropyl-3-(2,6-dichloro-phenyl)-isoxazol-4-ylmethoxy]-azepan-1-yl}-benzoic acid ethyl ester

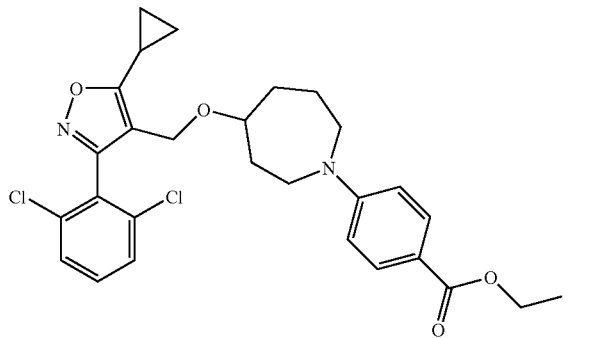

To a solution of 16 g (42 mmol) of 4-[5-cyclopropyl-3-(2,6-dichloro-phenyl)-isoxazol-4-ylmethoxy]-azepane in 40 mL of dimethyl sulfoxide, is added ethyl 4-iodobenzoate (21 g, 67 mmol), proline (2 g, 16.7 mmol) and copper(I) iodide (3.2 g, 16.7 mmol.). The resulting mixture is degassed with nitrogen followed by addition of potassium carbonate (11.6 g, 84 mmol). The reaction mixture is stirred at 100° C. for 14 hours. The mixture is cooled to room temperature and quenched with water. The mixture is extracted with EtOAc, the organics are dried over MgSO4, filtered and concentrated to afford a crude which is purified on silica gel column chromatography (Eluting with Hexanes/EtOAc 8:2), to obtained 17 g of the title racemic compound.
The racemic material is subjected to chiral purification (Chiralpak™ column, hex-DMEA (0.2%)/IPA 6:4 as eluent) to afford 8.28 g of the desired chiral isomer (isomer B). MS (m/e): 529 (M+1).

Step 11

4-{4-[5-Cyclopropyl-3-(2,6-dichloro-phenyl)-isoxazol-4-ylmethoxy]-azepan-1-yl}-benzoic acid

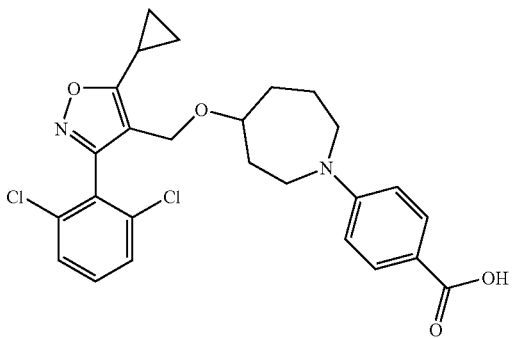

To a solution of 8.28 g (15.64 mmol) of 4-{4-[5-Cyclopropyl-3-(2,6-dichloro-phenyl)-isoxazol-4-ylmethoxy]-azepan-1-yl}-benzoic acid ethyl ester (Isomer B) in 50 mL of Ethanol and 150 mL of tetrahydrofuran, is added potassium hydroxide (55.16 g, 78.19 mmol). The resulting mixture is stirred at 60° C. for 14 hours. The mixture is cooled to room temperature and acidified with 2N HCl to pH 5-6. The solvent is removed under vacuum, the resulting slurry is diluted with CH₂Cl₂ (150 mL) and washed with water (2×80 mL). The organic layer is dried (MgSO₄), filtered and concentrated to afford 7.76 g of the title compound as a white solid (98%). MS (m/e): 501 (M+1).

Example 34

6-(4-((5-Cyclopropyl-3-(2,6-dichlorophenyl)isoxazol-4-yl)methoxy)azepan-1-yl)benzo[d]isothiazole-3-carboxylic acid

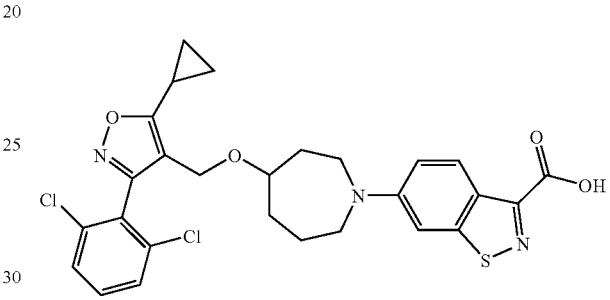

Step 1

Intermediate Preparation 34A

Methyl 6-(4-((5-cyclopropyl-3-(2,6-dichlorophenyl)isoxazol-4-yl)methoxy)azepan-1-yl)benzo[d]isothiazole-3-carboxylate

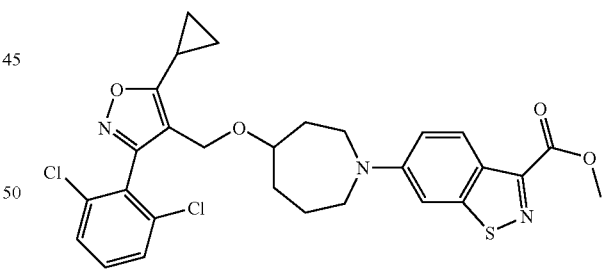

To an oven dried flask purged with argon, add 4-((azepan-4-yloxy)methyl)-5-cyclopropyl-3-(2,6-dichlorophenyl)isoxazol (0.51 g, 1.34 mmol), methyl 6-bromobenzo[d]isothiazole-3-carboxylate (0.30 g, 1.10 mmol), cesium carbonate (0.51 g, 1.56 mmol), X-Phos (0.04 g, 0.084 mmol), xylene (10 ml) and Pd₂(dba)₃ (0.025 g, 0.028 mmol). Purge the mixture with argon and heat to 130° C. until the starting materials are consumed as confirmed by TLC. Cool the reaction mixture to room temperature, filter through celite and concentrate in vacuo. The crude product is purified by flash chromatography on silica gel eluting with 6:4 hexane/ethyl acetate to give 0.30 g (47.0%) of the title compound as an off white solid. ES/MS m/z 571.11 (M+1).

The compounds listed in TABLE 4 are prepared essentially as described in Example 34, Step 1 using the appropriate amine and bromide intermediates (reagents). Preparations 1 and 2 use S-Phos (0.075 eq) and BINAP (0.075 eq) instead of X-Phos (0.075 eq)—which was used in all other preparations in Table 4.

TABLE 4

| Prep No | Name | Data |
|---|---|---|
| 35A | Methyl 4-(4-((5-cyclopropyl-3-(2,6-dichlorophenyl)isoxazol-4-yl)methoxy)azepan-1-yl)-2-methylbenzoate | ES/MS (M + 1) 529.16 |
| 36A | Methyl 3-(4-((5-cyclopropyl-3-(2,6-dichlorophenyl)isoxazol-4-yl)methoxy)azepan-1-yl)benzoate | ES/MS (M + 1) 515.12 |
| 37A | Methyl 6-(4-((5-cyclopropyl-3-(2,6-dichlorophenyl)isoxazol-4-yl)methoxy)azepan-1-yl)-1-methyl-1H-indazole-3-carboxylate | ES/MS (M + 1) 571.13 |
| 38A | Methyl 5-(4-((5-cyclopropyl-3-(2,6-dichlorophenyl)isoxazol-4-yl)methoxy)azepan-1-yl)benzo[b]thiophene-2-carboxylate | ES/MS (M + 1) 571.09 |
| 39A | Methyl 5-(4-((5-cyclopropyl-3-(2,6-dichlorophenyl)isoxazol-4-yl)methoxy)azepan-1-yl)-1-methyl-1H-indole-2-carboxylate | ES/MS (M + 1) 568.26 |
| 40A | Methyl 6-(4-((5-cyclopropyl-3-(2,6-dichlorophenyl)isoxazol-4-yl)methoxy)azepan-1-yl)benzo[b]thiophene-2-carboxylate | ES/MS (M + 1) 571.12 |
| 41A | Methyl 6-(4-((5-cyclopropyl-3-(2,6-dichlorophenyl)isoxazol-4-yl)methoxy)azepan-1-yl)-1-methyl-1H-indole-2-carboxylate | ES/MS (M + 1) 568.25 |
| 42A | Methyl 4-(4-((1-(2,6-dichlorophenyl)-4-isopropyl-1H-pyrazol-5-yl)methoxy)azepan-1-yl)benzoate | ES/MS (M + 1) 516.15 |
| 43A | Methyl 4-(4-((1-(2,6-dichlorophenyl)-4-isopropyl-1H-1,2,3-triazol-5-yl)methoxy)azepan-1-yl)benzoate | ES/MS (M + 1) 517.15 |
| 44A | Methyl 4-(4-((5-cyclopropyl-3-(2-(trifluoromethoxy)phenyl)isoxazol-4-yl)methoxy)azepan-1-yl)benzoate | ES/MS (M + 1) 522.10 |
| 45A | Methyl 6-(4-((5-cyclopropyl-3-(2-(trifluoromethoxy)phenyl)isoxazol-4-yl)methoxy)azepan-1-yl)-1-methyl-1H-indole-3-carboxylate | ES/MS (M + 1) 584.30 |
| 46A | Ethyl 6-(4-((5-cyclopropyl-3-(2-(trifluoromethoxy)phenyl)isoxazol-4-yl)methoxy)azepan-1-yl)benzo[b]thiophene-3-carboxylate | ES/MS (M + 1) 601.26 |

Step 2

6-(4-((5-Cyclopropyl-3-(2,6-dichlorophenyl)isoxazol-4-yl)methoxy)azepan-1-yl)benzo[d]isothiazole-3-carboxylic acid Potassium hydroxide (0.118 g, 2.10 mmol) is added to a solution of methyl 6-(4-((5-cyclopropyl-3-(2,6-dichlorophenyl)isoxazol-4-yl)methoxy)azepan-1-yl)benzo[d]isothiazole-3-carboxylate (0.30 g, 0.52 mmol) in ethanol (2 ml) and tetrahydrofuran (6 mL). The mixture is stirred at 60° C. for 24 h and concentrated in vacuo. The residue is dissolved in water (8 ml), acidified to pH~5 with 1 N HCl and extracted with dichloromethane (2×10 ml). The organic extracts are dried over sodium sulfate and the solvent is evaporated in vacuo to give 0.15 g (51.0%) of the title compound as an off white solid. ES/MS m/z 558.06 (M+1).

The compounds listed in TABLE 5 are prepared essentially as described in the preparation of Example 34, Step 2, using the esters from preparations 35A-46A.

TABLE 5

| Ex No | Name | Data |
|---|---|---|
| 35 | 4-(4-((5-Cyclopropyl-3-(2,6-dichlorophenyl)isoxazol-4-yl)methoxy)azepan-1-yl)-2-methylbenzoic acid | ES/MS (M + 1) 514.14 |
| 36 | 3-(4-((5-Cyclopropyl-3-(2,6-dichlorophenyl)isoxazol-4-yl)methoxy)azepan-1-yl)benzoic acid | ES/MS (M + 1) 501.14 |
| 37 | 6-(4-((5-Cyclopropyl-3-(2,6-dichlorophenyl)isoxazol-4-yl)methoxy)azepan-1-yl)-1-methyl-1H-indazole-3-carboxylic acid | ES/MS (M + 1) 555.22 |
| 38 | 5-(4-((5-Cyclopropyl-3-(2,6-dichlorophenyl)isoxazol-4-yl)methoxy)azepan-1-yl)benzo[b]thiophene-2-carboxylic acid | ES/MS (M + 1) 557.11 |
| 39 | 5-(4-((5-Cyclopropyl-3-(2,6-dicrilorophenyl)isoxazol-4-yl)methoxy)azepan-1-yl)-1-methyl-1H-indole-2-carboxylic acid | ES/MS (M + 1) 554.25 |
| 40 | 6-(4-((5-Cyclopropyl-3-(2,6-dichlorophenyl)isoxazol-4-yl)methoxy)azepan-1-yl)benzo[b]thiophene-2-carboxylic acid | ES/MS (M + 1) 557.07 |
| 41 | 6-(4-((5-Cyclopropyl-3-(2,6-dichlorophenyl)isoxazol-4-yl)methoxy)azepan-1-yl)-1-methyl-1H-indole-2-carboxylic acid | ES/MS (M + 1) 554.17 |
| 42 | 4-(4-((1-(2,6-Dichlorophenyl)-4-isopropyl-1H-pyrazol-5-yl)methoxy)azepan-1-yl)benzoic acid | ES/MS (M + 1) 502.19 |
| 43 | 4-(4-((1-(2,6-Dichlorophenyl)-4-isopropyl-1H-1,2,3-triazol-5-yl)methoxy)azepan-1-yl)benzoic acid | ES/MS (M + 1) 503.16 |
| 44 | 4-(4-((5-Cyclopropyl-3-(2-(trifluoromethoxy)phenyl)isoxazol-4-yl)methoxy)azepan-1-yl)benzoic acid | ES/MS (M + 1) 517.18 |
| 45 | 6-(4-((5-Cyclopropyl-3-(2-(trifluoromethoxy)phenyl)isoxazol-4-yl)methoxy)azepan-1-yl)-1-methyl-1H-indole-3-carboxylic acid | ES/MS (M + 1) 570.27 |
| 46 | 6-(4-((5-Cyclopropyl-3-(2-(trifluoromethoxy)phenyl)isoxazol-4-yl)methoxy)azepan-1-yl)benzo[b]thiophene-3-carboxylic acid | ES/MS (M + 1) 573.07 |

We claim:
1. A compound of formula

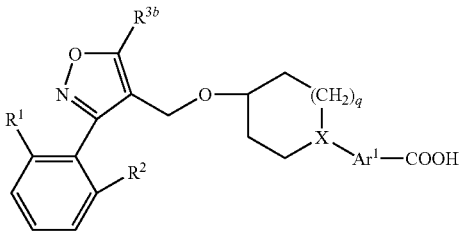

wherein:
q is 1 or 2;
$R^1$ is chloro, fluoro, or trifluoromethoxy;
$R^2$ is hydrogen chloro, fluoro, or trifluoromethoxy;
$R^{3b}$ is trifluoromethyl, cyclopropyl or isopropyl;
X is C or N, provided that when X is C, q is 1;
$Ar^1$ is selected from the group consisting of benzoisothiazolyl, benzothienyl, indazolyl, indolyl, naphthyl, phenyl and pyridinyl, each optionally substituted methyl or phenyl; or a pharmaceutically acceptable salt or enantiomer thereof.

2. A compound according to claim 1 wherein $R^1$ is chloro or trifluoromethoxy and $R^2$ is hydrogen or chloro; or a pharmaceutically acceptable salt or enantiomer thereof.

3. A compound according to claim 1 wherein $R^1$ and $R^2$ are both Chloro or wherein $R^1$ is trifluoromethoxy and $R^2$ is hydrogen; or a pharmaceutically acceptable salt or enantiomer thereof.

4. A compound according to claim 1 wherein $R^{3b}$ is cyclopropyl or isopropyl; or a pharmaceutically acceptable salt or enantiomer thereof.

5. A compound according to claim 1 wherein $R^{3b}$ is cyclopropyl; or a pharmaceutically acceptable salt or enantiomer thereof.

6. A compound according to claim 1 wherein $Ar^1$ is 6-benzoisothiazolyl, 5-benzothienyl, 6-benzothienyl, 6-indazolyl, 5-indolyl, 6-indolyl, 4-phenyl or 2-pyridinyl, each optionally substituted with methyl or phenyl; or a pharmaceutically acceptable salt or enantiomer thereof.

7. A compound according to claim 1 wherein $Ar^1$ is 6-benzoisothiazolyl, 5-benzothienyl, 6-benzothienyl, 6-indazolyl, 5-indolyl, 6-indolyl, or 4-phenyl, each optionally substituted with methyl; or a pharmaceutically acceptable salt or enantiomer thereof.

8. A compound according to claim 1 wherein $Ar^1$ group is 5-benzothienyl, 6-benzothienyl, 5-indolyl, 6-indolyl or 4-phenyl, each optionally substituted with methyl; or a pharmaceutically acceptable salt or enantiomer thereof.

9. A compound according to claim 1 wherein q is 1 and X is N; or a pharmaceutically acceptable salt or enantiomer thereof.

10. A compound according to claim 1 wherein q is 1 and X is C; or a pharmaceutically acceptable salt or enantiomer thereof.

11. A compound according to claim 1 wherein q is 2 and X is N; or a pharmaceutically acceptable salt or enantiomer thereof.

12. A compound according to claim 1 wherein $R^1$ is chloro or trifluoromethoxy; $R^2$ is hydrogen or chloro; $R^{3b}$ is cyclopropyl; X is C or N and $Ar^1$ group is 4-phenyl, 2-pyridinyl, 6-indolyl or 6-benzothienyl each optionally substituted with methyl.

13. A compound according to claim 1 selected from the group consisting of:
5-{4-[5-Cyclopropyl-3-(2,6-dichloro-phenyl)-isoxazol-4-ylmethoxy]-piperidin-1-yl}-biphenyl-2-carboxylic acid,
5-{4-[5-Cyclopropyl-3-(2-trifluoromethoxy-phenyl)-isoxazol-4-ylmethoxy]-piperidin-1-yl}-biphenyl-2-carboxylic acid,
5-{4-[3-(2,6-Dichloro-phenyl)-5-isopropyl-isoxazol-4-ylmethoxy]-piperidin-1-yl}-biphenyl-2-carboxylic acid,
4-{-4-[3-(2,6-Dichloro-phenyl)-5-isopropyl-isoxazol-4-ylmethoxy]-piperidin-1-yl}-naphthalene-1-carboxylic acid,
4-{4-[5-Cyclopropyl-3-(2,6-dichloro-phenyl)-isoxazol-4-ylmethoxy]-piperidin-1-yl}-3-methyl-benzoic acid,
4-{4-[5-Isopropyl-3-(2-trifluoromethoxy-phenyl)-isoxazol-4-ylmethoxy]-piperidin-1-yl}-benzoic acid,
4-{4-[5-Cyclopropyl-3-(2,6-dichloro-phenyl)-isoxazol-4-ylmethoxy]-piperidin-1-yl}-benzoic acid,
4-{4-[5-Cyclopropyl-3-(2-trifluoromethoxy-phenyl)-isoxazol-4-ylmethoxy]-piperidin-1-yl}-2-methyl-benzoic acid,
4-{4-[5-Cyclopropyl-3-(2,6-dichloro-phenyl)-isoxazol-4-ylmethoxy]-piperidin-1-yl}-2-methyl-benzoic acid,
4-{4-[3-(2,6-Dichloro-phenyl)-5-isopropyl-isoxazol-4-ylmethoxy]-piperidin-1-yl}-2-methyl-benzoic acid,
4-{4-[3-(2,6-Dichloro-phenyl)-5-isopropyl-isoxazol-4-ylmethoxy]-piperidin-1-yl}-benzoic acid,
6-{4-[3-(2,6-Dichloro-phenyl)-5-isopropyl-isoxazol-4-ylmethoxy]-piperidin-1-yl}-1-methyl-1H-indole-3-carboxylic acid,
6-{4-[3-(2,6-Dichloro-phenyl)-5-isopropyl-isoxazol-4-ylmethoxy]-piperidin-1-yl}-benzo[b]thiophene-3-carboxylic acid,
6-{4-[5-Cyclopropyl-3-(2-trifluoromethoxy-phenyl)-isoxazol-4-ylmethoxy]-piperidin-1-yl}-1-methyl-1H-indole-3-carboxylic acid,
6-{4-[5-Cyclopropyl-3-(2,6-dichloro-phenyl)-isoxazol-4-ylmethoxy]-piperidin-1-yl}-1-methyl-1H-indole-3-carboxylic acid,
6-{4-[5-Cyclopropyl-3-(2,6-dichloro-phenyl)-isoxazol-4-ylmethoxy]-piperidin-1-yl}-benzo[b]thiophene-3-carboxylic acid,
4-[5-Cyclopropyl-3-(2,6-dichloro-phenyl)-isoxazol-4-ylmethoxy]-3,4,5,6-tetrahydro-2H-[1,2]bipyridinyl-5'-carboxylic acid,
4-{4-[3-(2,6-Dichloro-phenyl)-5-isopropyl-isoxazol-4-ylmethoxy]-piperidin-1-yl}-3-methyl-benzoic acid,
4-{4-[5-Cyclopropyl-3-(2,6-dichloro-phenyl)-isoxazol-4-ylmethoxy]-azepan-1-yl}-benzoic acid,
6-{4-[5-Cyclopropyl-3-(2,6-dichloro-phenyl)-isoxazol-4-ylmethoxy]-azepan-1-yl}-1-methyl-1H-indole-3-carboxylic acid,
6-{4-[5-Cyclopropyl-3-(2,6-dichloro-phenyl)-isoxazol-4-ylmethoxy]-azepan-1-yl}-benzo[b]thiophene-3-carboxylic acid,
Trans-4-{4-[5-Cyclopropyl-3-(2,6-dichloro-phenyl)-isoxazol-4-ylmethoxy]-cyclohexyl}-benzoic acid,
Trans-4-{4-[5-Cyclopropyl-3-(2-trifluoromethoxy-phenyl)-isoxazol-4-ylmethoxy]-cyclohexyl}-benzoic acid,
Trans-6-{4-[5-Cyclopropyl-3-(2-trifluoromethoxy-phenyl)-isoxazol-4-ylmethoxy]-cyclohexyl}-1-methyl-1H-indole-3-carboxylic acid, and
Cis-6-{4-[5-Cyclopropyl-3-(2-trifluoromethoxy-phenyl)-isoxazol-4-ylmethoxy]-cyclohexyl}-1-methyl-1H-indole-3-carboxylic acid;
or a pharmaceutically acceptable salt or enantiomer thereof.

14. The compound 4-{4-[5-Cyclopropyl-3-(2,6-dichloro-phenyl)-isoxazol-4-ylmethoxy]-azepan-1-yl}-benzoic acid

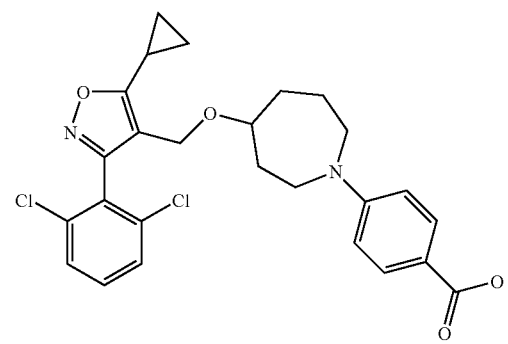

or a pharmaceutically acceptable salt or enantiomer thereof.

15. The compound trans-4-{4-[5-Cyclopropyl-3-(2,6-dichloro-phenyl)-isoxazol-4-ylmethoxy]-cyclohexyl}-benzoic acid

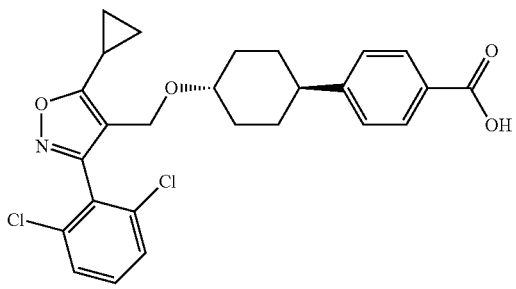

or a pharmaceutically acceptable salt or enantiomer thereof.

16. The compound 6-{4-[5-Cyclopropyl-3-(2,6-dichloro-phenyl)-isoxazol-4-ylmethoxy]-piperidin-1-yl}-1-methyl-1H-indole-3-carboxylic acid

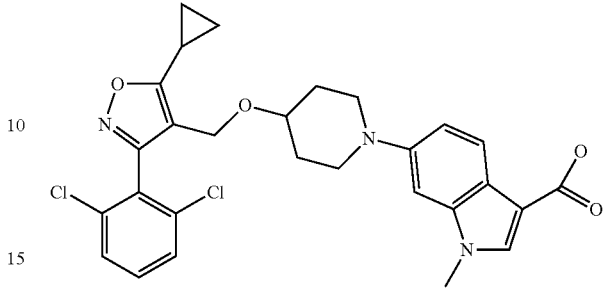

or a pharmaceutically acceptable salt or enantiomer thereof.

17. A method for treating dyslipidemia and related diseases comprising administering a therapeutically effective amount of a compound according to claim 1 to a patient in need thereof.

18. A pharmaceutical composition comprising a compound according to claim 1 and a carrier, diluent, or excipient.

* * * * *

UNITED STATES PATENT AND TRADEMARK OFFICE
CERTIFICATE OF CORRECTION

| | | |
|---|---|---|
| PATENT NO. | : 8,153,624 B2 | Page 1 of 1 |
| APPLICATION NO. | : 12/600879 | |
| DATED | : April 10, 2012 | |
| INVENTOR(S) | : Michael James Genin et al. | |

It is certified that error appears in the above-identified patent and that said Letters Patent is hereby corrected as shown below:

In column 60, line 65, in Claim 1, delete "substituted" and insert --substituted with--, therefor.

In column 61, line 54, in Claim 13, delete "4-{-4-" and insert --4-{4- --, therefor.

In column 62, line 22 (approximate), in Claim 13, delete "[1,2]" and insert --[1,2']--, therefor.

Signed and Sealed this
Twenty-ninth Day of May, 2012

David J. Kappos
*Director of the United States Patent and Trademark Office*